(12) United States Patent
Allison et al.

(10) Patent No.: US 7,449,184 B2
(45) Date of Patent: Nov. 11, 2008

(54) FIXED DOSING OF HER ANTIBODIES

(75) Inventors: David E. Allison, San Mateo, CA (US); Rene Bruno, Marseilles (FR); Jian-Feng Lu, Foster City, CA (US); Chee M. Ng, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 121 days.

(21) Appl. No.: 11/154,091

(22) Filed: Jun. 15, 2005

(65) Prior Publication Data

US 2006/0165702 A1  Jul. 27, 2006

Related U.S. Application Data

(60) Provisional application No. 60/645,697, filed on Jan. 21, 2005.

(51) Int. Cl.
*A61K 39/365* (2006.01)
*C07K 16/30* (2006.01)

(52) U.S. Cl. ............... 424/138.1; 424/130.1; 424/141.1; 424/143.1; 530/387.1; 530/388.1; 530/388.8; 530/388.85; 514/2

(58) Field of Classification Search ............ None
See application file for complete search history.

(56) References Cited

U.S. PATENT DOCUMENTS

| | | | |
|---|---|---|---|
| 4,935,341 A | 6/1990 | Bargmann et al. |
| 4,968,603 A | 11/1990 | Slamon et al. |
| 5,183,884 A | 2/1993 | Kraus et al. |
| 5,288,477 A | 2/1994 | Bacus |
| 5,401,638 A | 3/1995 | Carney et al. |
| 5,480,968 A | 1/1996 | Kraus et al. |
| 5,514,554 A | 5/1996 | Bacus |
| 5,571,894 A | 11/1996 | Wels et al. |
| 5,587,458 A | 12/1996 | King et al. |
| 5,604,107 A | 2/1997 | Carney et al. |
| 5,641,869 A | 6/1997 | Vandlen et al. |
| 5,648,237 A | 7/1997 | Carter |
| 5,677,171 A | 10/1997 | Hudziak et al. |
| 5,705,157 A | 1/1998 | Greene |
| 5,720,937 A | 2/1998 | Hudziak et al. |
| 5,720,954 A | 2/1998 | Hudziak et al. |
| 5,725,856 A | 3/1998 | Hudziak et al. |
| 5,747,261 A | 5/1998 | King et al. |
| 5,770,195 A | 6/1998 | Hudziak et al. |
| 5,772,997 A | 6/1998 | Hudziak et al. |
| 5,783,186 A | 7/1998 | Arakawa et al. |
| 5,783,404 A | 7/1998 | Koski |
| 5,804,396 A | 9/1998 | Plowman |
| 5,821,337 A | 10/1998 | Carter et al. |
| 5,824,311 A | 10/1998 | Greene et al. |
| 5,837,243 A | 11/1998 | Deo et al. |
| 5,846,749 A | 12/1998 | Slamon et al. |
| 5,856,089 A | 1/1999 | Wang et al. |
| 5,877,305 A | 3/1999 | Huston et al. |
| 5,910,486 A | 6/1999 | Curiel et al. |
| 5,922,845 A | 7/1999 | Deo et al. |
| 5,925,519 A | 7/1999 | Jensen et al. |
| 5,939,531 A | 8/1999 | Wels et al. |
| 5,977,322 A | 11/1999 | Marks et al. |
| 5,985,553 A | 11/1999 | King et al. |
| 5,994,071 A | 11/1999 | Ross et al. |
| 6,015,567 A | 1/2000 | Hudziak et al. |
| 6,028,059 A | 2/2000 | Curiel et al. |
| 6,054,297 A | 4/2000 | Carter et al. |
| 6,123,939 A | 9/2000 | Shawver et al. |
| 6,127,526 A | 10/2000 | Blank |
| 6,165,464 A | 12/2000 | Hudziak et al. |
| 6,214,388 B1 | 4/2001 | Benz et al. |
| 6,267,958 B1 | 7/2001 | Andya et al. |
| 6,270,765 B1 | 8/2001 | Deo et al. |
| 6,333,169 B1 | 12/2001 | Hudziak et al. |
| 6,333,348 B1 | 12/2001 | Vogel et al. |
| 6,333,398 B1 | 12/2001 | Blank |
| 6,339,142 B1 | 1/2002 | Basey et al. |
| 6,358,682 B1 | 3/2002 | Jaffee et al. |
| 6,387,371 B1 | 5/2002 | Hudziak et al. |
| 6,395,272 B1 | 5/2002 | Deo et al. |
| 6,399,063 B1 | 6/2002 | Hudziak et al. |
| 6,403,630 B1 | 6/2002 | Dannenberg et al. |
| 6,407,213 B1 | 6/2002 | Carter et al. |
| 6,417,335 B1 | 7/2002 | Basey et al. |
| 6,458,356 B1 | 10/2002 | Arakawa et al. |
| 6,489,447 B1 | 12/2002 | Basey et al. |

(Continued)

FOREIGN PATENT DOCUMENTS

| | | |
|---|---|---|
| EP | 0 599 274 A1 | 6/1994 |
| EP | 0 616 812 B1 | 9/1994 |
| EP | 0 656 367 A1 | 6/1995 |
| EP | 0 412 116 B1 | 11/1995 |
| EP | 0 494 135 B1 | 4/1996 |
| EP | 0 502 812 B1 | 8/1996 |
| EP | 0 711 565 B1 | 8/1998 |
| EP | 0 554 441 B1 | 1/1999 |
| EP | 1 006 194 A2 | 6/2000 |
| EP | 0 444 181 B1 | 10/2001 |
| EP | 1 357 132 A2 | 10/2003 |

(Continued)

OTHER PUBLICATIONS

Animal Dosage "Dose Calculator", p. 1.*

(Continued)

*Primary Examiner*—Larry R. Helms
*Assistant Examiner*—Laura B Goddard
(74) *Attorney, Agent, or Firm*—Wendy M. Lee

(57) ABSTRACT

The present invention concerns fixed dosing of HER antibodies, such as Pertuzumab.

32 Claims, 18 Drawing Sheets

U.S. PATENT DOCUMENTS

| | | |
|---|---|---|
| 6,512,097 B1 | 1/2003 | Marks et al. |
| 6,573,043 B1 | 6/2003 | Cohen et al. |
| 6,582,919 B2 | 6/2003 | Danenberg |
| 6,602,670 B2 | 8/2003 | Danenberg |
| 6,627,196 B1 | 9/2003 | Baughman et al. |
| 6,632,979 B2 | 10/2003 | Erickson et al. |
| 6,639,055 B1 | 10/2003 | Carter et al. |
| 6,685,940 B2 | 2/2004 | Andya et al. |
| 6,719,971 B1 | 4/2004 | Carter et al. |
| 6,767,541 B2 | 7/2004 | Slamon et al. |
| 6,797,814 B2 | 9/2004 | Blank |
| 6,800,738 B1 | 10/2004 | Carter et al. |
| 6,821,515 B1 | 11/2004 | Cleland et al. |
| 7,041,292 B1 | 5/2006 | Sliwkowski |
| 7,097,840 B2 | 8/2006 | Erickson et al. |
| 2001/0014326 A1 | 8/2001 | Andya et al. |
| 2002/0001587 A1 | 1/2002 | Erickson et al. |
| 2002/0031515 A1 | 3/2002 | Caligiuri et al. |
| 2002/0051785 A1 | 5/2002 | Slamon et al. |
| 2002/0064785 A1 | 5/2002 | Mass |
| 2002/0076408 A1 | 6/2002 | Buchsbaum |
| 2002/0076695 A1 | 6/2002 | Ross |
| 2002/0090662 A1 | 7/2002 | Ralph |
| 2002/0141993 A1 | 10/2002 | Ashkenazi et al. |
| 2002/0142328 A1 | 10/2002 | Danenberg |
| 2002/0155527 A1 | 10/2002 | Stuart et al. |
| 2002/0192211 A1 | 12/2002 | Hudziak et al. |
| 2002/0192652 A1 | 12/2002 | Danenberg |
| 2003/0022918 A1 | 1/2003 | Horak et al. |
| 2003/0059790 A1 | 3/2003 | Jaffee et al. |
| 2003/0068318 A1 | 4/2003 | O'Brien et al. |
| 2003/0086924 A1* | 5/2003 | Sliwkowski .............. 424/143.1 |
| 2003/0103973 A1 | 6/2003 | Rockwell et al. |
| 2003/0108545 A1 | 6/2003 | Rockwell et al. |
| 2003/0134344 A1 | 7/2003 | Mass |
| 2003/0144252 A1 | 7/2003 | Furr |
| 2003/0147884 A1 | 8/2003 | Paton et al. |
| 2003/0152572 A1 | 8/2003 | Homma et al. |
| 2003/0152987 A1 | 8/2003 | Cohen et al. |
| 2003/0157097 A1 | 8/2003 | Noguchi et al. |
| 2003/0165840 A1 | 9/2003 | Danenberg |
| 2003/0170234 A1 | 9/2003 | Hellmann |
| 2003/0175845 A1 | 9/2003 | Kalbag et al. |
| 2003/0202972 A1 | 10/2003 | Andya et al. |
| 2003/0202973 A1 | 10/2003 | Pieczenik |
| 2003/0211530 A1 | 11/2003 | Danenberg |
| 2003/0228663 A1 | 12/2003 | Lowman et al. |
| 2004/0013297 A1 | 1/2004 | Lo |
| 2004/0013667 A1 | 1/2004 | Kelsey et al. |
| 2004/0037823 A9 | 2/2004 | Paton et al. |
| 2004/0037824 A1 | 2/2004 | Baughman et al. |
| 2004/0082047 A1 | 4/2004 | Jefferson et al. |
| 2004/0106161 A1 | 6/2004 | Bossenmaier et al. |
| 2004/0138160 A1 | 7/2004 | Nato et al. |
| 2004/0209290 A1 | 10/2004 | Cobleigh et al. |
| 2004/0236078 A1 | 11/2004 | Carter et al. |
| 2004/0258685 A1 | 12/2004 | Brunetta et al. |
| 2005/0002928 A1 | 1/2005 | Hellmann |
| 2005/0208043 A1 | 9/2005 | Adams et al. |
| 2005/0238640 A1 | 10/2005 | Sliwkowski |
| 2005/0244417 A1 | 11/2005 | Ashkenazi et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya et al. |
| 2006/0121044 A1 | 6/2006 | Amler et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0216285 A1 | 9/2006 | Adams et al. |
| 2006/0228745 A1 | 10/2006 | Mass |
| 2006/0275305 A1 | 12/2006 | Bryant |
| 2006/0275306 A1 | 12/2006 | Andya et al. |
| 2007/0020261 A1 | 1/2007 | Sliwkowski et al. |
| 2007/0026001 A1 | 2/2007 | Ashkenazi et al. |
| 2007/0037228 A1 | 2/2007 | Moecks et al. |
| 2007/0077243 A1 | 4/2007 | Carter et al. |
| 2007/0166753 A1 | 7/2007 | Mass |
| 2007/0184055 A1 | 8/2007 | Sliwkowski |
| 2007/0202516 A1 | 8/2007 | Mass |
| 2007/0224203 A1 | 9/2007 | Friess et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen |
| 2008/0050385 A1 | 2/2008 | Friess et al. |

FOREIGN PATENT DOCUMENTS

| | | |
|---|---|---|
| WO | WO 87/07646 A2 | 12/1987 |
| WO | WO 89/10412 A1 | 11/1989 |
| WO | WO 91/02062 A2 | 2/1991 |
| WO | WO 91/05264 A1 | 4/1991 |
| WO | WO 93/03741 A1 | 3/1993 |
| WO | WO 93/12220 A1 | 6/1993 |
| WO | WO 93/16185 A2 | 8/1993 |
| WO | WO 93/21232 A1 | 10/1993 |
| WO | WO 93/21319 A1 | 10/1993 |
| WO | WO 94/00136 A1 | 1/1994 |
| WO | WO 94/22478 A1 | 10/1994 |
| WO | WO 96/07321 A1 | 3/1996 |
| WO | WO 96/16673 A1 | 6/1996 |
| WO | WO 96/40789 A1 | 12/1996 |
| WO | WO 97/00271 A1 | 1/1997 |
| WO | WO 97/20858 A1 | 6/1997 |
| WO | WO 97/38731 A1 | 10/1997 |
| WO | WO 98/02463 A1 | 1/1998 |
| WO | WO 98/17797 A1 | 4/1998 |
| WO | WO 98/18489 A1 | 5/1998 |
| WO | WO 98/33914 A1 | 8/1998 |
| WO | WO 98/45479 A1 | 10/1998 |
| WO | WO 99/31140 A1 | 6/1999 |
| WO | WO 99/48527 A1 | 9/1999 |
| WO | WO 99/55367 A1 | 11/1999 |
| WO | WO 00/09160 A1 | 2/2000 |
| WO | WO 00/61145 A1 | 10/2000 |
| WO | WO 00/61185 A1 | 10/2000 |
| WO | WO 00/69460 A1 | 11/2000 |
| WO | WO 00/78347 A1 | 12/2000 |
| WO | WO 01/00238 A1 | 1/2001 |
| WO | WO 01/00244 A2 | 1/2001 |
| WO | WO 01/00245 A2 | 1/2001 |
| WO | WO 01/09187 A2 | 2/2001 |
| WO | WO 01/15730 A1 | 3/2001 |
| WO | WO 01/20033 A1 | 3/2001 |
| WO | WO 01/32155 A2 | 5/2001 |
| WO | WO 01/53354 A2 | 7/2001 |
| WO | WO 01/56604 A1 | 8/2001 |
| WO | WO 01/64246 A2 | 9/2001 |
| WO | WO 01/76586 A1 | 10/2001 |
| WO | WO 01/76630 A1 | 10/2001 |
| WO | WO 01/87334 A1 | 11/2001 |
| WO | WO 01/87336 A1 | 11/2001 |
| WO | WO 01/89566 A1 | 11/2001 |
| WO | WO 02/05791 A2 | 1/2002 |
| WO | WO 02/11677 A2 | 2/2002 |
| WO | WO 02/44413 A2 | 6/2002 |
| WO | WO 02/45653 A2 | 6/2002 |
| WO | WO 02/009754 A1 | 7/2002 |

| | | | |
|---|---|---|---|
| WO | WO 02/055106 A2 | 7/2002 |
| WO | WO 02/070008 A1 | 9/2002 |
| WO | WO 02/087619 A1 | 11/2002 |
| WO | WO 02/089842 A1 | 11/2002 |
| WO | WO 03/006509 A2 | 1/2003 |
| WO | WO 03/012072 A2 | 2/2003 |
| WO | WO 03/028638 A2 | 4/2003 |
| WO | WO 03/041736 A2 | 5/2003 |
| WO | WO 03/086467 A1 | 10/2003 |
| WO | WO 03/087131 A2 | 10/2003 |
| WO | WO 04/000094 A2 | 12/2003 |
| WO | WO 2004/008099 A2 | 1/2004 |
| WO | WO 2004/024866 A2 | 3/2004 |
| WO | WO 2004/048525 A2 | 6/2004 |
| WO | WO 2004/053497 A2 | 6/2004 |
| WO | WO 2004/063709 A2 | 7/2004 |
| WO | WO 2005/099756 A2 | 10/2005 |
| WO | WO 2006/007398 A1 | 1/2006 |
| WO | WO 2006/033700 A2 | 3/2006 |
| WO | WO 2006/044908 A2 | 4/2006 |
| WO | WO 2006/063042 A2 | 6/2006 |
| WO | WO 2006/091693 A2 | 8/2006 |
| WO | WO 2006/096861 A2 | 9/2006 |
| WO | WO 2007/013950 A2 | 2/2007 |
| WO | WO 2007/019899 A2 | 2/2007 |
| WO | WO 2008/031531 A1 | 3/2008 |

OTHER PUBLICATIONS

White et al. (2001, Ann. Rev. Med., 2001, 52:125-145).*
Agus et al., "Clinical Activity in a Phase I Trial of HER2-Targeted rhuMAb 2C4 (pertuzumab) in Patients with Advanced Solid Malignancies" (Slides presented at the 2003 ASCO Annual Meeting) pp. 1-32 (2003).
Agus et al., "Efficacy and safety of single agent pertuzumab (rhuMAb 2C4), a HER dimerization inhibitor, in hormone refractory prostate cancer after failure of taxane-based therapy" Journal of Clinical Oncology (Abstract 4624 from the 41st Annual Meeting of ASCO) 23 (16S):408s (Jun. 1, 2005).
Agus, D. et al., "Efficacy and safety of single agent pertuzumab (rhuMAb 2C4), a HER dimerization inhibitor, in hormone refractory prostate cancer after failure of taxane-based therapy" (Poster 4624 from the 41st Annual Meeting of the American Society of Clinical Oncology) (May 15, 2005).
Allison et al., "Pharmacokinetics (PK) of pertuzumab (rhuMAb 2C4) in Phase II Studies of Ovarian, Breast, Prostate, and Lung Cancers" (Poster 2532 presented at the 2005 ASCO Meeting) (May 2005).
Allison et al., "Pharmacokinetics of HER2-Targeted rhuMAb 2C4 (OMNITARG) in Patients with Advanced Solid Malignancies: Phase Ia Results" (Poster 790 from the 2003 ASCO Annual Meeting) (2003).
Amler et al., "Identification of a predictive expression pattern for phosphorylated HER2 as a potential diagnostic marker for pertuzumab (OMNITARG) activity in ovarian cancer" (Poster 4497 presented at the Apr. 2006 American Association for Cancer Research Meeting) (Apr. 2006).
Bossenmaier et al., "Presence of HER2/HER3 heterodimers predicts antitumor effects of pertuzumab (OMNITARG) in different human xenograft models" Proc AM Assoc Cancer Res (Abstract 5342) 45:1232 (Mar. 2004).
Cortes et al., "Open label, randomized, phase II study of pertuzumab (OMNITARG) in patients with metastatic breast cancer (MBC) with low expression of HER2" (Poster 3068 from the 41st Annual Meeting of the American Society of Clinical Oncology (ASCO) ) (May 15, 2005).
Cortes et al., "Open label, randomized, phase II study of pertuzumab (P) in patients (pts) with metastatic breast cancer (MBC) with low expression of HER2" Journal of Clinical Oncology (Abstract 3068 from the 41st Annual Meeting of ASCO) 23 (16s):208s (Jun. 1, 2005).
de Bono et al., "An open label, phase II, multicancer study to evaluate the efficacy and safety of pertuzumab in chemotherapy-naive patients with Hormone-Refractory Prostate Cancer (HRPC)" (Poster 4609 from the 41st Annual Meeting of the American Society of Clinical Oncology (ASCO)) (May 15, 2005).
de Bono et al., "An open label, phase II, multicenter, study to evaluate the efficacy and safety of pertuzumab (P) in chemotherapy naive patients (pts) with Hormone Refractory Prostate Cancer (HRPC)" Journal of Clinical Oncology (Abstract 4609; 41st Annual Meeting of ASCO) 23(16S):405a (Jun. 1, 2005).
ERBITUX (CETUXIMAB) (product information) (Jun. 2004).
Friess et al., "Combination treatment with erlotinib and pertuzumab against human tumor xenografts is superior to monotherapy" Clinical Cancer Research 11(14) :5300-5309 (Jul. 15, 2005).
Friess et al., "In vivo activity of recombinant humanized monoclonal antibody 2C4 in xenografts is independent of tumor type and degree of HER2 overexpression" European Journal of Cancer (Abstract 496 from the EORTC-NCI-AACR conference in Frankfurt, Germany Nov. 19-22, 2002.) 38 (Suppl. 7) :S149 (2002).
Gelman et al., "Model checking and improvement" Bayesian Data Analysis, Boca Raton:Chapman & Hall/CRC, Chapter 6, pp. 157-196 (2004).
Gelman et al., "Model checking and model improvement" Markov Chain Monte Carlo in Practice, W. R. Gilks, S. Richardson, and D.J. Spiegelhalter, Boca Raton:Chapman & Hall/CRC, Chapter 11, pp. 189-201 (1996).
Gordon et al., "Clinical activity of pertuzumab (rhuMab 2C4) in advanced, refractory or recurrent ovarian cancer (OC), and the role of HER2 activation status" Journal of Clinical Oncology (Abstract #5051 from the 41st Annual Meeting of ASCO) 23(16S) :467s (Jun. 1, 2005).
Gordon et al., "Clinical activity of pertuzumab (rhuMab 2C4) in advanced, refractory or recurrent ovarian cancer and the role of HER2 activation status" (Poster #5051 from the 41st Annual Meeting of the American Society of Clinical Oncology (ASCO) ) (May 15, 2005).
Harris et al., "A population pharmacokinetic (PK) model for HERCEPTIN(H) and implications for clinical dosing" (Poster presented at the 2002 ASCO Annual Meeting) (2002).
Hasmann et al., "Pertuzumab (Omnitarg) Potentiates Antitumor Effects on NSCLS Xenografts without Increasing Toxicity when Combined with Cytotoxic Chemotherapeutic Agents" American Association for Cancer Research (Abstract #B213; supplement to Clinical Cancer Research) 9(16) (Dec. 1, 2003).
HERCEPTIN (Trastuzumab) (product information) (2004).
Lu et al., "When should dose be adjusted to body size? A population pharmacokinetic (PPK) simulation" Clinical Pharmacology & Therapeutics (Abstract PIII-89. Poster is attached.) pp. P86 (Feb. 2003).
Malik et al., "Dose-Response Studies of Recombinant Humanized Monoclonal Antibody 2C4 (Pertuzumab) in Tumor Xenograft Models" (Poster No. 773 presented at the American Association for Cancer Research meeting) (2003).
Agus et al., "Phase I clinical study of pertuzumab, a novel HER dimerization inhibitor, in patients with advanced cancer" Journal of Clinical Oncology 23(11) :2534-2543 (Apr. 10, 2005).
Baselga, J., "Phase I and II clinical trials of trastuzumab" Annals of Oncology 12 (Suppl 1) :S49-S55 (2001).
Franklin et al., "Insights into ErbB signaling from the structure of the ErbB2-pertuzumab complex" Cancer Cell 5(4) :317-328 (Apr. 2004).
Leyland-Jones, B., "Dose scheduling—Herceptin" Oncology 61 (Suppl 2) :31-36 (2001).
Malik et al., "Dose-Response Studies of Recombinant Humanized Monoclonal Antibody 2C4 in Tumor Xenograft Models" Proceedings of the American Association for Cancer Research (Abstract No. 773) 44:150 (Jul. 2003).
Ng et al., "Rationale for fixed dosing of pertuzumab by population pharmacokinetic (POP PK) modeling" Clinical Pharmacology & Therapeutics (Abstract PI-97) 77(2) :P33 (2005).
Aasland et al., "Expression of Oncogenes in Thyroid Tumours: Coexpression of c-erbB2/neu and c-erbB" British Journal of Cancer 57(4) :358-363 (Apr. 1988).
Agus et al., "Clinical Activity in a Phase I Trial of HER-2-Targeted rhuMAb 2C4 (pertuzumab) in Patients with Advanced Solid Malignancies (AST)" *Proceedings of the American Association for Cancer Research* (Abstract No. 771) 22:192 (2003).

Agus et al., "Targeting ligand-activated ErbB2 signaling inhibits breast and prostate tumor growth" *Cancer Cell* 2(2):127-137 (Aug. 2002).

Allison et al., "Pharmacokinetics (PK) of pertuzumab (rhuMAb 2C4) in Phase II Studies of Ovarian, Breast, Prostate, and Lung Cancers" *Journal of Clinical Oncology* (Jun. 1 Supplement) 23(16S):2532 (2005).

Allison et al., "Pharmacokinetics of HER2-Targeted rhuMAb 2C4 (pertuzumab) in Patients with Advanced Solid Malignancies: Phase Ia Results" *Meeting Proceedings of the American Society of Clinical Oncology* (Abstract No. 790) 22:197 (2003).

Artega et al., "p185$^{c\text{-}erbB\text{-}2}$ Signaling Enhances Cisplatin-induced Cytotoxicity in Human Breast Carcinoma Cells: Association Between an Oncogenic Receptor Tyrosine Kinase and Drug-induced DNA Repair" *Cancer Research* 54(14):3758-3765 (Jul. 15, 1994).

Bacus et al., "Differentiation of Cultured Human Breast Cancer Cells (AU-565 and MCF-7) Associated With Loss of Cell Surface HER-2/neu Antigen" *Molecular Carcinogenesis* 3 (6):350-362 (1990).

Bacus et al., "Tumor-inhibitory Monoclonal Antibodies to the HER-2/Neu Receptor Induce Differentiation of Human Breast Cancer Cells" *Cancer Research* 52(9):2580-2589 (May 1, 1992).

Baker et al., "Role of body surface area in dosing of investigational anticancer agents in adults, 1991-2001" *J. Natl. Cancer Institute* 94(24):1883-1888 (Dec. 18, 2002).

Baselga and Mendelsohn, "Receptor Blockade With Monoclonal Antibodies As Anti-Cancer Therapy" *Pharmac. Ther.* 64:127-154 (1994).

Baselga et al., "Phase II Study of Weekly Intravenous Recombinant Humanized Anti-p185$^{HER2}$ Monoclonal Antibody in Patients With HER2/neu-Overexpressing Metastatic Breast Cancer" *J. Clin. Oncol.* 14(3):737-744 (Mar. 1996).

Borst et al., "Oncogene Alterations in Endometrial Carcinoma" *Gynecologic Oncology* 38(3):364-366 (Sep. 1990).

Carraway and Cantley, "A Neu Acquaintance for ErbB3 and ErbB4: A Role for Receptor Heterodimerization in Growth Signaling" *Cell* 78:5-8 (Jul. 15, 1994).

Carraway et al., "Neuregulin-2, A New Ligand of ErbB3/ErbB4-Receptor Tyrosine Kinases" *Nature* 387:512-516 (May 1997).

Chang et al., "Ligands For ErbB-Family Receptors Encoded By a Neuregulin-Like Gene" *Nature* 387:509-512 (May 29, 1977).

Cho et al., "Structure of the extracellular region of HER2 alone and in complex with the Herceptin Fab" *Nature* 421(6924):756-760 (Feb. 13, ).

Cohen et al., "Expression Pattern of the neu (NGL) Gene-Encoded Growth Factor Receptor Protein (p185$^{neu}$) in Normal and Transformed Epithelial Tissues of the Digestive Tract" *Oncogene* 4(1):81-88 (Jan. 1989).

Cronin et al., "Measurement of gene expression in archival paraffin-embedded tissues: development and performance of a 92-gene reverse transcriptase-polymerase chain reaction assay" *Am. J. Path.* 164(1):35-42.

D'Souza and Taylor-Papadimitriou., "Overexpression of ERBB2 in Human Mammary Epithelial Cells Signals Inhibition of Transcription of the E-Cadherin Gene" *Proc. Natl. Acad. Sci. USA* 91(15):7202-7206 (Jul. 19, 1994).

de Jong et al., "Flat-fixed dosing of irinotecan: influence on pharmacokinetic and pharmacodynamic variability" *Clinical Cancer Research* (Part 1) 10(12):4068-4071 (Jun. 15, 2004).

de Jongh et al., "Body-surface area-based dosing does not increase accuracy of predicting cisplatin exposure" *J. Clin. Oncol.* 19(17):3733-3739 (Sep. 1, 2001).

Drebin et al., "Down-Modulation of an Oncogene Protein Product and Reversion of the Transformed Phenotype by Monoclonal Antibodies" *Cell* 41(3):695-706 (Jul. 1985).

Drebin et al., "Monoclonal Antibodies Reactive With Distinct Domains of the neu Oncogene-Encoded p185 Molecule Exert Synergistic Anti-Tumor Effects In Vivo" *Oncogene* 2:273-277 (1988).

Earp et al., "Heterodimerization and Functional Interaction Between EGF Receptor Family Members: A New Signaling Paradigm With Implications For Breast Cancer Research" *Breast Cancer Res and Treatment* 35:115-132 (1995).

Egorin, M., "Horseshoes, hand grenades, and body-surface area-based dosing: aiming for a target" *Journal of Clinical Oncology* 21(2):182-183 (Jan. 15, 2003).

Felici et al., "Dosing strategies for anticancer drugs: the good, the bad and body-surface area" *European Journal of Cancer* 38(13):1677-1684 (Sep. 2002).

Fendly, B.M. et al., "Characterization of Murine Monoclonal Antibodies Reactive to Either the Human Epidermal Growth Factor Receptor or HER2/neu Gene Product" *Cancer Research* 50:1550-1558 (Mar. 1, 1990).

Fukushige et al., "Localization of a Novel v-erbB-Related Gene, c-erbB-2, on Human Chromosome 17 and Its Amplification in a Gastric Cancer Cell Line." *Molecular & Cellular Biology* 6(3):955-958 (Mar. 1986).

Gelman et al. *Bayesian Data Analysis*, Boca Raton:Chapman & Hall/CRC (2004).

Gelman et al. *Model Checking and Model Improvement*, W. R. Gilks, S. Richardson, and D.J. Spiegelhalter, Boca Raton:Chapman & Hall/CRC pp. 189-192 (1996).

Groenen et al., "Structure-Function Relationships for the EGF/TGF-α Family of Mitogens" *Growth Factors* 11:235-257 (1994).

Gu et al., "Overexpression of her-2/neu in Human Prostate Cancer and Benign Hyperplasia" *Cancer Letters* 99:185-189 (1996).

Guerin et al., "Overexpression of Either c-myc or c-erbB-2/neu Proto-Oncogenes in Human Breast Carcinomas: Correlation with Poor Prognosis" *Oncogene Res* 3:21-31 (1988).

Hancock et al., "A Monoclonal Antibody Against the c-erbB-2 Protein Enhances the Cytotoxicity of cis-Diamminedichloroplatinum Against Human Breast and Ovarian Tumor Cell Lines" *Cancer Research* 51:4575-4580 (Sep. 1, 1991).

Harari et al., "Molecular mechanisms underlying ErbB2/HER2 action in breast cancer" *Oncogene* 19(53):6102-6114 (Dec. 11, 2000).

Harari et al., "Neuregulin-4: A Novel Growth Factor That Acts Through the ErbB-4 Receptor Tyrosine Kinase" *Oncogene* 18:2681-2689 (1999).

Harris et al., "A population pharmacokinetic (PK) model for trastuzumab (Herceptin) and implications for clinical dosing" *Proc Am Soc Clin Oncol* (Abstract #488) 21:123a (2002).

Harwerth et al., "Monoclonal Antibodies Against the Extracellular Domain of the erbB-2 Receptor Function as Partial Ligand Agonists" *Journal of Biological Chemistry* 267(21):15160-15167 (Jul. 25, 1992).

Holmes et al., "Identification of Heregulin, A Specific Activator of P185$^{erbB2}$" *Science* 256:1205-1210 (May 22, 1992).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165-1172 (Mar. 1989).

Kasprzyk et al., "Therapy of an Animal Model of Human Gastric Cancer Using a Combination of Anti-erbB-2 Monoclonal Antibodies" *Cancer Research* 52(10):2771-2776 (May 15, 1992).

Kern et al., "p185$^{neu}$ Expression in Human Lung Adenocarcinomas Predicts Shortened Survival" *Cancer Research* 50(16):5184-5191 (Aug. 15, 1990).

King et al., "Amplification of a Novel v-erbB-Related Gene in a Human Mammary Carcinoma" *Science* 229:974-976 (Sep. 1985).

Klapper et al., "A Subclass of Tumor-Inhibitory Monoclonal Antibodies to ErbB-2/HER2 Blocks Crosstalk With Growth Factor Receptors" *Oncogene* 14:2099-2109 (1997).

Kotts et al., "Differential Growth Inhibition of Human Carcinoma Cells Exposed to Monoclonal Antibodies Directed against the Extracellular Domain of the HER2/ERBB2 Protooncogene" In Vitro (Abstract #176) 26 (3):59A (1990).

Kraus et al., "Isolation and Characterization of ERBB3, A Third Member of the ERBB/Epidermal Growth Factor Receptor Family: Evidence for Overexpression in a Subset of Human Mammary Tumors" *Proc. Natl. Acad. Sci. USA* 86:9193-9197 (Dec. 1989).

Kumar et al., "Regulation of Phosphorylation of the c-erbB-2/HER2 Gene Product by a Monoclonal Antibody and Serum Growth Factor(s) in Human Mammary Carcinoma Cells" *Molecular & Cellular Biology* 11(2):979-986 (Feb. 1991).

Lee et al., "Transforming Growth Factor α: Expression, Regulation, and Biological Activities" *Pharmacological Reviews* 47(1) :51-85 (Mar. 1995).

Lemke, G., "Neuregulins in Development" *Molecular and Cellular Neuroscience* 7:247-262 (1996).

Levi et al., "The Influence of Heregulins on Human Schwann Cell Proliferation" *J. Neuroscience* 15(2) :1329-1340 (Feb. 1995).

Lewis et al., "Differential Responses of Human Tumor Cell Lines to Anti-p185$^{HER2}$ Monoclonal Antibodies" *Cancer Immunol. Immunother.* 37:255-263 (1993).

Lewis et al., "Growth Regulation of Human Breast and Ovarian Tumor Cells by Heregulin: Evidence for the Requirement of ErbB2 as a Critical Component in Mediating Heregulin Responsiveness" *Cancer Research* 56:1457-1465 (Mar. 15, 1996).

Leyland-Jones et al., "Pharmacokinetics, safety, and efficacy of trastuzumab administered every three weeks in combination with paclitaxel" *J. Clin. Oncol.* 21(21) :3965-3971 (Nov. 1, 2003).

Loos et al., "Inter- and intrapatient variability in oral topotecan pharmacokinetics: implications for body-surface area dosage regimens" *Clin. Cancer Res.* 6(7) :2685-2689 (Jul. 2000).

Lu et al., "A Population Pharmacokinetic Model for Bevacizumab" *Clinical Pharmacology & Therapeutics* (Abstract PII-149) 75(2) :91 (2004).

Ma et al., "A two-gene expression ratio predicts clinical outcome in breast cancer patients treated with tamoxifen" *Cancer Cell* 5(6) :607-616 (Jun. 2004).

Maier et al., "Requirements for the Internalization of a Murine Monoclonal Antibody Directed against the HER-2/neu Gene Product c-erbB-2" *Cancer Research* 51(19) :5361-5369 (Oct. 1, 1991).

Malik et al., "Dose-Response Studies of Recombinant Humanized Monoclonal Antibody 2C4 in Tumor Xenograft Models" *Proceedings of the AACR* (Abstract No. 773) 44:176-177 (Mar. 2003).

Masui et al., "Growth Inhibition of Human Tumor Cells in Athymic Mice by Anti-Epidermal Growth Factor Receptor Monoclonal Antibodies" *Cancer Research* 44(3) :1002-1007 (Mar. 1984).

Mathijssen et al., "Impact of body-size measures on irinotecan clearance: alternative dosing recommendations" *Journal of Clinical Oncology* 20(1) :81-87 (Jan. 1, 2002).

McCann et al., "c-erbB-2 Oncoprotein Expression in Primary Human Tumors" *Cancer* 65(1) :88-92 (Jan. 1, 1990).

McKensie et al., "Generation and Characterization of Monoclonal Antibodies Specific for the Human neu Oncogene Product, p185" *Oncogene* 4 :543-548 (1989).

Morrissey et al., "Axon-Induced Mitogenesis of Human Schwann Cells Involves Heregulin and p185$^{erbB2}$" *Proc. Natl. Acad. Sci. USA* 92:1431-1435 (Feb. 1995).

Myers et al., "Biological Effects of Monoclonal Antireceptor Antibodies Reactive with neu Oncogene Product, p185neu" *Methods in Enzymology* 198:277-290 (1991).

Park et al., "Amplification, Overexpression, and Rearrangement of the erbB-2 Protooncogene in Primary Human Stomach Carcinomas" *Cancer Research* 49(23) :6605-6609 (Dec. 1, 1989).

Pietras et al., "Antibody to HER-2/neu Receptor Blocks DNA Repair After Cisplatin in Human Breast and Ovarian Cancer Cells" *Oncogene* 9:1829-1838 (1994).

Plowman et al., "Heregulin Induces Tyrosine Phosphorylation of HER4/p180$^{erbB4}$" *Nature* (Letters to Nature) 366:473-475 (Dec. 2, 1993).

Plowman et al., "Ligand-Specific Activation of HER4/p180$^{erbB4}$, A Fourth Member of the Epidermal Growth Factor Receptor Family" *Proc. Natl. Acad. Sci. USA* 90:1746-1750 (Mar. 1993).

Ross et al., "HER-2/neu Gene Amplification Status in Prostate Cancer by Fluorescence in Situ Hybridization" *Hum. Pathol.* 28(7) :827-833 (Jul. 1997).

Ross et al., "Prognostic Significance of HER-2/neu Gene Amplification Status by Fluorescence In Situ Hybridization of Prostate Carcinoma" *Cancer* 79(11) :2162-2170 (Jun. 1, 1997).

Sadasivan et al., "Overexpression of Her-2/Neu May Be An Indicator of Poor Prognosis in Prostate Cancer" *J. Urol.* 150:126-131 (Jul. 1993).

Sarup et al., "Characterization of an Anti-P185$^{HER2}$ Monoclonal Antibody that Stimulates Receptor Function and Inhibits Tumor Cell Growth" *Growth Regulation* 1:72-82 (1991).

Schaefer et al., "γ-Heregulin: A Novel Heregulin Isoform That is an Autocrine Growth Factor for the Human Breast Cancer Cell Line, MDA-MB-175" *Oncogene* 15:1385-1394 (1997).

Scott et al., "p185$^{HER2}$ Signal Transduction in Breast Cancer Cells" *Journal of Biological Chemistry* 266(22):14300-14305 (Aug. 5, 1991).

Shawver et al., "Ligand-Like Effects Induced by Anti-c-erbB-2 Antibodies Do Not Correlate with and Are Not Required for Growth Inhibition of Human Carcinoma Cells" *Cancer Research* 54(5): 1367-1373 (Mar. 1, 1994).

Shepard et al., "Monoclonal Antibody Therapy of Human Cancer: Taking the HER2 Protooncogene to the Clinic" *J. Clin. Immunol.* 11(3):117-127 (1991).

Slamon et al., "Human Breast Cancer: Correlation of Relapse and Survival with Amplification of the HER-2/neu Oncogene" *Science* 235:177-182 (Jan. 9, 1987).

Slamon et al., "Studies of the HER-2/neu Proto-Oncogene in Human Breast and Ovarian Cancer" *Science* 244:707-712 (May 12, 1989).

Sliwkowski et al., "Coexpression of erbB2 and erbB3 Proteins Reconstitutes a High Affinity Receptor for Heregulin" *Journal of Biological Chemistry* 269(20) :14661-14665 (May 20, 1994).

Sliwkowski et al., "Ready to partner" *Nat. Struct. Biol.* 10(3) :158-159 (Mar. 2003).

Stancovski et al., "Mechanistic Aspects of the Opposing Effects of Monoclonal Antibodies to the ERBB2 Receptor on Tumor Growth" *Proc. Natl. Acad. Sci. USA* 88(19) :8691-8695 (Oct. 1, 1991).

Tagliabue et al., "Selection of Monoclonal Antibodies Which Induce Internalization and Phosphorylation of p185$^{HER2}$ and Growth Inhibition of Cells With HER2/NEU Gene Amplification" *International Journal of Cancer* 47(6) :933-937 (Apr. 1, 1991).

Vitetta and Uhr, "Monoclonal Antibodies as Agonists: An Expanded Role for Their Use in Cancer Therapy" *Cancer Research* 54 (20): 5301-5309 (Oct. 15, 1994).

Weiner et al., "Expression of the neu Gene-encoded Protein (P185$^{neu}$) in Human Non-Small Cell Carcinomas of the Lung" *Cancer Research* 50(2) :421-425 (Jan. 15, 1990).

Williams et al., "Expression of c-erbB-2 in Human Pancreatic Adenocarcinomas" *Pathobiology* 59(1) :46-52 (1991).

Wu et al., "Apoptosis Induced By an Anti-Epidermal Growth Factor Receptor Monoclonal Antibody in a Human Colorectal Carcinoma Cell Line and Its Delay By Insulin" *Journal of Clinical Investigation* 95(4) :1897-1905 (Apr. 1995).

Xu et al., "Antibody-Induced Growth Inhibition is Mediated Through Immunochemically and Functionally Distinct Epitopes on the Extracellular Domain of the c-erbB-2 (HER-2/neu) Gene Product p185" *International Journal of Cancer* 53(3) :401-408 (Feb. 1, 1993).

Yano et al., "Evaluating Pharmacokinetic/Pharmacodynamic Models Using the Posterior Predictive Check" *Journal of Pharmacokinetics and Pharmacodynamics* 28(2) :171-192 (2001).

Yarden et al., "Untangling the erbB signalling network" *Nat. Rev. Mol. Cell. Biol.* 2(2) :127-137 (Feb. 2001).

Yokota et al., "Amplification of c-erbB-2 Oncogene in Human Adenocarcinomas in Vivo" *Lancet* 1 (8484) :765-767 (Apr. 5, 1986).

Yonemura et al., "Evaluation of Immunoreactivity for erbB-2 Protein as a Marker of Poor Short Term Prognosis in Gastric Cancer" *Cancer Research* 51(3) :1034-1038 (Feb. 1, 1991).

Zhang et al., "Neuregulin-3 (NRG3): A novel neural tissue-enriched protein that binds and activates ErbB4" *Proc. Natl. Acad. Sci. USA* 94:9562-9567 (Sep. 22, 1997).

Zhau et al., "Amplification and Expression of the c-erb B-2/neu Proto-Oncogene in Human Bladder Cancer" *Molecular Carcinogenesis* 3(5) :254-257 (1990).

\* cited by examiner

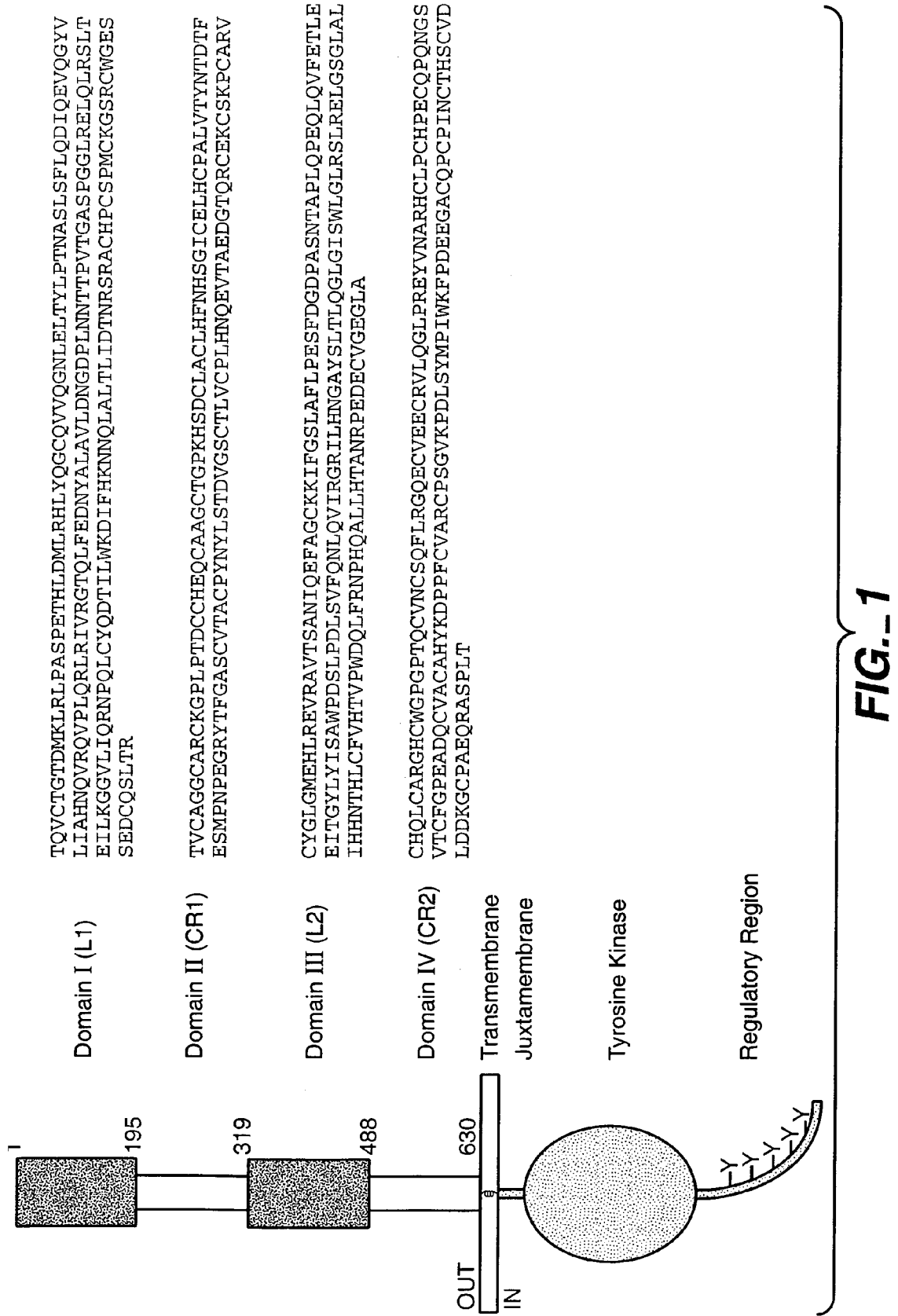
FIG._1

VARIABLE LIGHT

```
              10              20              30              40
2C4    DTVMTQSHKIMSTSVGDRVSITC  [KASQDVSIGVA]  WYQQRP
         **    ****  *           *                    *
574    DIQMTQSPSSLSASVGDRVTITC  [KASQDVSIGVA]  WYQQKP
                                   *   * hum κI DIQMTQSPSSLSASVGDRVTITC  [RASQSISNYLA]  WYQQKP 50              60              70              80
2C4    GQSPKLLIY  [SASYRYT]  GVPDRFTGSGSGTDFTFTISSVQA
         **                      *      *         *  * *
574    GKAPKLLIY  [SASYRYT]  GVPSRFSGSGSGTDFTLTISSLQP
         * ***** hum κI GKAPKLLIY  [AASSLES]  GVPSRFSGSGSGTDFTLTISSLQP 90             100
2C4    EDLAVYYC  [QQYYIYPYT]  FGGGTKLEIK   (SEQ ID NO:1)
        * *                    *    *
574    EDFATYYC  [QQYYIYPYT]  FGQGTKVEIK   (SEQ ID NO:3)
                  *** * hum κI EDFATYYC  [QQYNSLPWT]  FGQGTKVEIK   (SEQ ID NO:5)
```

FIG._2A

VARIABLE HEAVY

```
              10              20              30              40
2C4    EVQLQQSGPELVKPGTSVKISCKAS  [GFTFTDYTMD]  WVKQS
         **   **    *  *  ***  *                 * *
574    EVQLVESGGGLVQPGGSLRLSCAAS  [GFTFTDYTMD]  WVRQA
                                     ** * * hum III EVQLVESGGGLVQPGGSLRLSCAAS [GFTFSSYAMS]  WVRQA 50    a         60              70              80
2C4    HGKSLEWIG  [DVNPNSGGSIYNQRFKG]  KASLTVDRSSRIVYM
         *  *   **                      *** *    **** *
574    PGKGLEWVA  [DVNPNSGGSIYNQRFKG]  RFTLSVDRSKNTLYL
                    **** * ****      *  * hum III PGKGLEWVA [VISGDGGSTYYADSVKG]  RFTISRDNSKNTLYL abc    90           100ab          110
2C4    ELRSLTFEDTAVYYCAR  [NLGPSFYFDY]  WGQGTTLTVSS   (SEQ ID NO:2)
        ***  **                          **
574    QMNSLRAEDTAVYYCAR  [NLGPSFYFDY]  WGQGTLVTVSS   (SEQ ID NO:4)
                            ******** hum III QMNSLRAEDTAVYYCAR [GRVGYSLYDY]  WGQGTLVTVSS   (SEQ ID NO:6)
```

FIG._2B

Amino Acid Sequence for Pertuzumab Light Chain

```
  1         10        20        30        40        50        60
  |          |         |         |         |         |         |
DIQMTQSPSSLSASVGDRVTITCKASQDVSIGVAWYQQKPGKAPKLLIYSASYRYTGVPS 70        80        90       100       110       120
             |         |         |         |         |         |
RFSGSGSGTDFTLTISSLQPEDFATYYCQQYYIYPYTFGQGTKVEIKRTVAAPSVFIFPP 130       140       150       160       170       180
             |         |         |         |         |         |
SDEQLKSGTASVVCLLNNFYPREAKVQWKVDNALQSGNSQESVTEQDSKDSTYSLSSTLT 190       200       210
             |         |         |
LSKADYEKHKVYACEVTHQGLSSPVTKSFNRGEC
```

*FIG._3A*

Amino Acid Sequence for Pertuzumab Heavy Chain

```
  1         10        20        30        40        50        60
  |          |         |         |         |         |         |
EVQLVESGGGLVQPGGSLRLSCAASGFTFTDYTMDWVRQAPGKGLEWVADVNPNSGGSIY

70        80        90       100       110       120
             |         |         |         |         |         |
NQRFKGRFTLSVDRSKNTLYLQMNSLRAEDTAVYYCARNLGPSFYFDYWGQGTLVTVSSA 130       140       150       160       170       180
             |         |         |         |         |         |
STKGPSVFPLAPSSKSTSGGTAALGCLVKDYFPEPVTVSWNSGALTSGVHTFPAVLQSSG 190       200       210       220       230       240
             |         |         |         |         |         |
LYSLSSVVTVPSSSLGTQTYICNVNHKPSNTKVDKKVEPKSCDKTHTCPPCPAPELLGGP 250       260       270       280       290       300
             |         |         |         |         |        *|
SVFLFPPKPKDTLMISRTPEVTCVVVDVSHEDPEVKFNWYVDGVEVHNAKTKPREEQYNS 310       320       330       340       350       360
             |         |         |         |         |         |
TYRVVSVLTVLHQDWLNGKEYKCKVSNKALPAPIEKTISKAKGQPREPQVYTLPPSREEM 370       380       390       400       410       420
             |         |         |         |         |         |
TKNQVSLTCLVKGFYPSDIAVEWESNGQPENNYKTTPPVLDSDGSFFLYSKLTVDKSRWQ 430       440      448
             |         |        |
QGNVFSCSVMHEALHNHYTQKSLSLSPG
```

*FIG._3B*

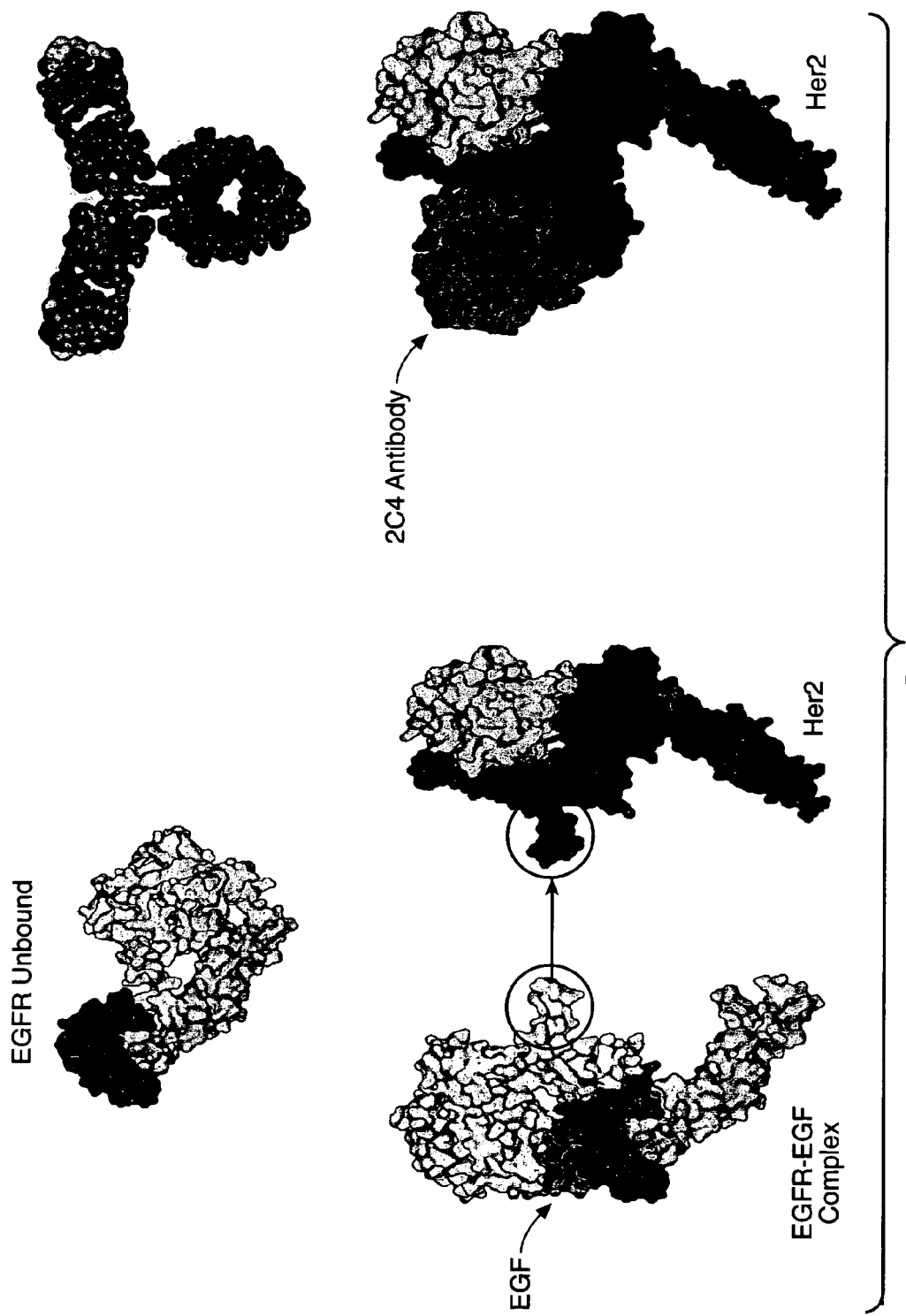
FIG._4

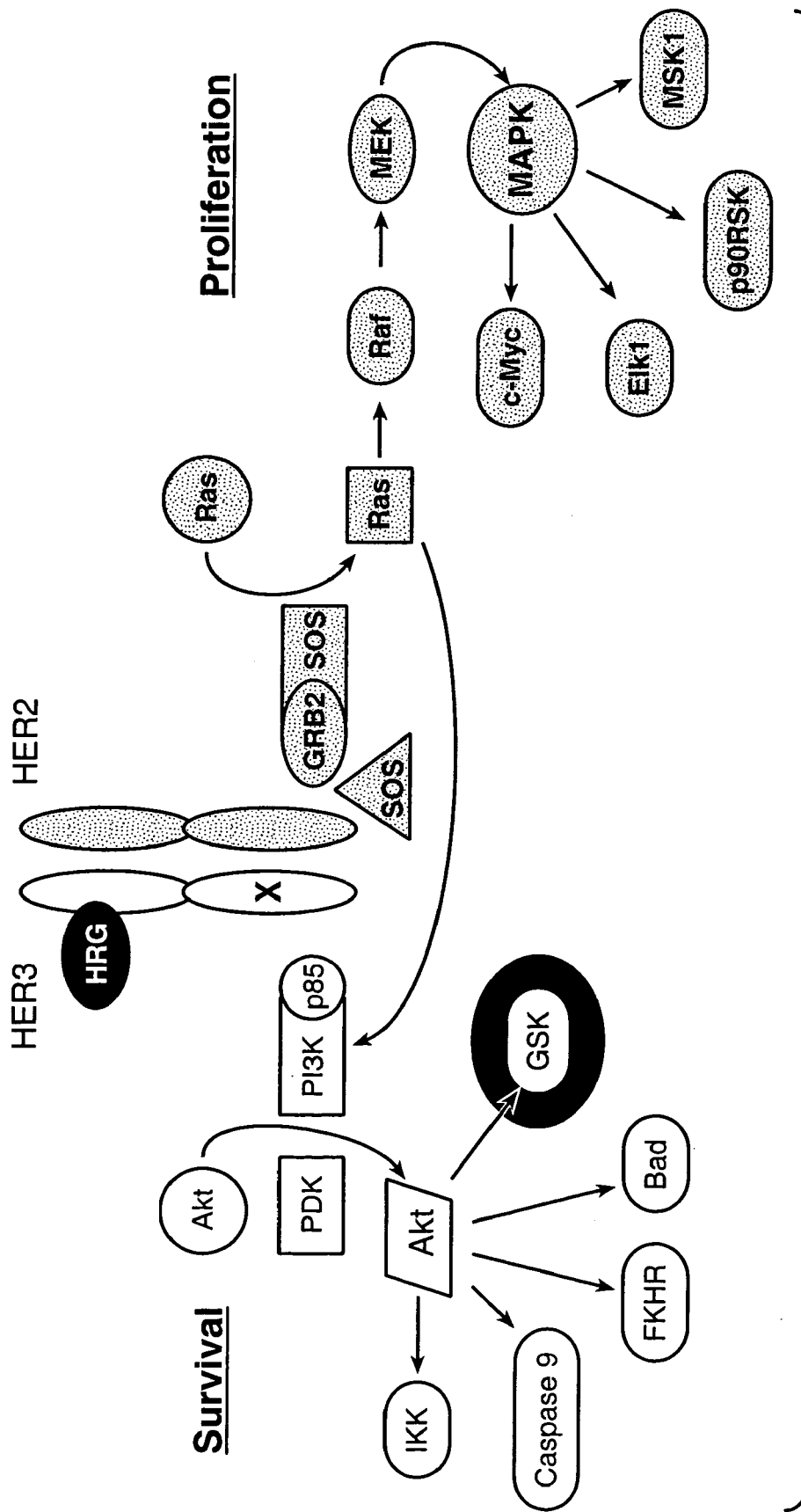
FIG._5

Trastuzumab
Herceptin
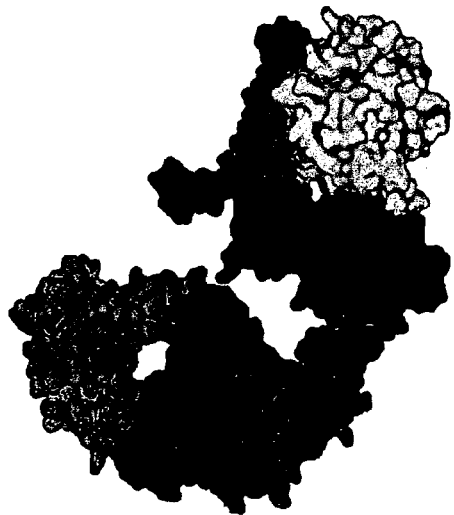
- Binds in IV near JM.
- Protects against receptor shedding
- Moderately affects receptor down-modulation
- Slight effect on HER2's role as a coreceptor
Pertuzumab
Omnitarg
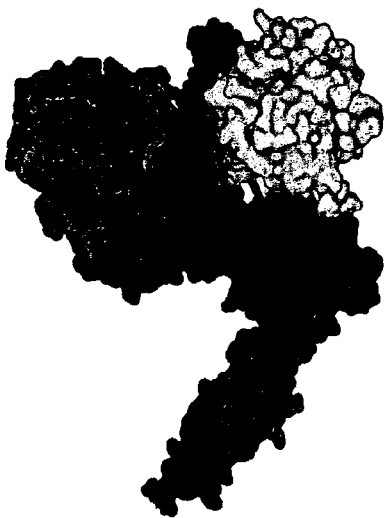
- Binds in II at dimerization interface
- Does not prevent receptor shedding
- Moderately affects receptor down-modulation
- Major effect on HER2's role as a coreceptor
FIG._6

LIGHT CHAIN

```
1                15               30                45
DIQMTQSPSSLSASVGDRVTITCRASQDVNTAVAWYQQKPGKAPK
46               60               75               90
LLIYSASFLYSGVPSRFSGSRSGTDFTLTISSLQPEDFATYYCQQ
91              105              120              135
HYTTPPTFGQGTKVEIKRTVAAPSVFIFPPSDEQLKSGTASVVCL
136             150              165              180
LNNFYPREAKVQWKVDNALQSGNSQESVTEQDSKDSTYSLSSTLT
181             195              210  214
LSKADYEKHKVYACEVTHQGLSSPVTKSFNRGEC
```

FIG._7A

HEAVY CHAIN

```
1                15               30                45
EVQLVESGGGLVQPGGSLRLSCAASGFNIKDTYIHWVRQAPGKGL
46               60               75                90
EWVARIYPTNGYTRYADSVKGRFTISADTSKNTAYLQMNSLRAED
91              105              120               135
TAVYYCSRWGGDGFYAMDYWGQGTLVTVSSASTKGPSVFPLAPSS
136             150              165               180
KSTSGGTAALGCLVKDYFPEPVTVSWNSGALTSGVHTFPAVLQSS
181             195              210               225
GLYSLSSVVTVPSSSLGTQTYICNVNHKPSNTKVDKKVEPKSCDK
226             240              255               270
THTCPPCPAPELLGGPSVFLFPPKPKDTLMISRTPEVTCVVVDVS
271             285              300               315
HEDPEVKFNWYVDGVEVHNAKTKPREEQYNSTYRVVSVLTVLHQD
316             330              345               360
WLNGKEYKCKVSNKALPAPIEKTISKAKGQPREPQVYTLPPSREE
361             375              390               405
MTKNQVSLTCLVKGFYPSDIAVEWESNGQPENNYKTTPPVLDSDG
406             420              435               449
SFFLYSKLTVDKSRWQQGNVFSCSVMHEALHNHYTQKSLSLSPG
```

```
  1 EVQLVESGGGLVQPGGSLRLSCAASGFTFTDYTMDWVRQAPGKGL                45
 46 EWVADVNPNSGGSIYNQRFKGRFTLSVDRSKNTLYLQMNSLRAED                90
 91 TAVYYCARNLGPSFYFDYWGQGTLVTVSSASTKGPSVFPLAPSSK               135
136 STSGGTAALGCLVKDYFPEPVTVSWNSGALTSGVHTFPAVLQSSG               180
181 LYSLSSVVTVPSSSLGTQTYICNVNHKPSNTKVDKKVEPKSCDKT               225
226 HTCPPCPAPELLGGPSVFLFPPKPKDTLMISRTPEVTCVVVDVSH               270
271 EDPEVKFNWYVDGVEVHNAKTKPREEQYNSTYRVVSVLTVLHQDW               315
316 LNGKEYKCKVSNKALPAPIEKTISKAKGQPREPQVYTLPPSREEM               360
361 TKNQVSLTCLVKGFYPSDIAVEWESNGQPENNYKTTPPVLDSDGS               405
406 FFLYSKLTVDKSRWQQGNVFSCSVMHEALHNHYTQKSLSLSPGK                449
```

FIG._8B

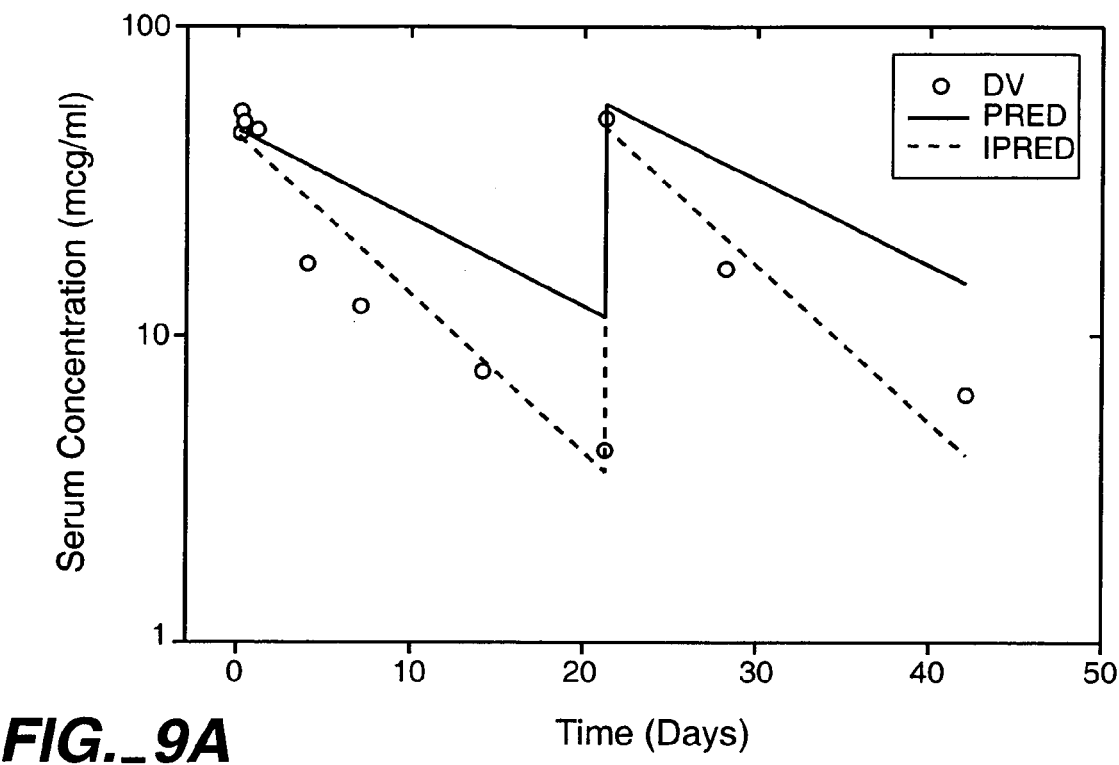
FIG._9A
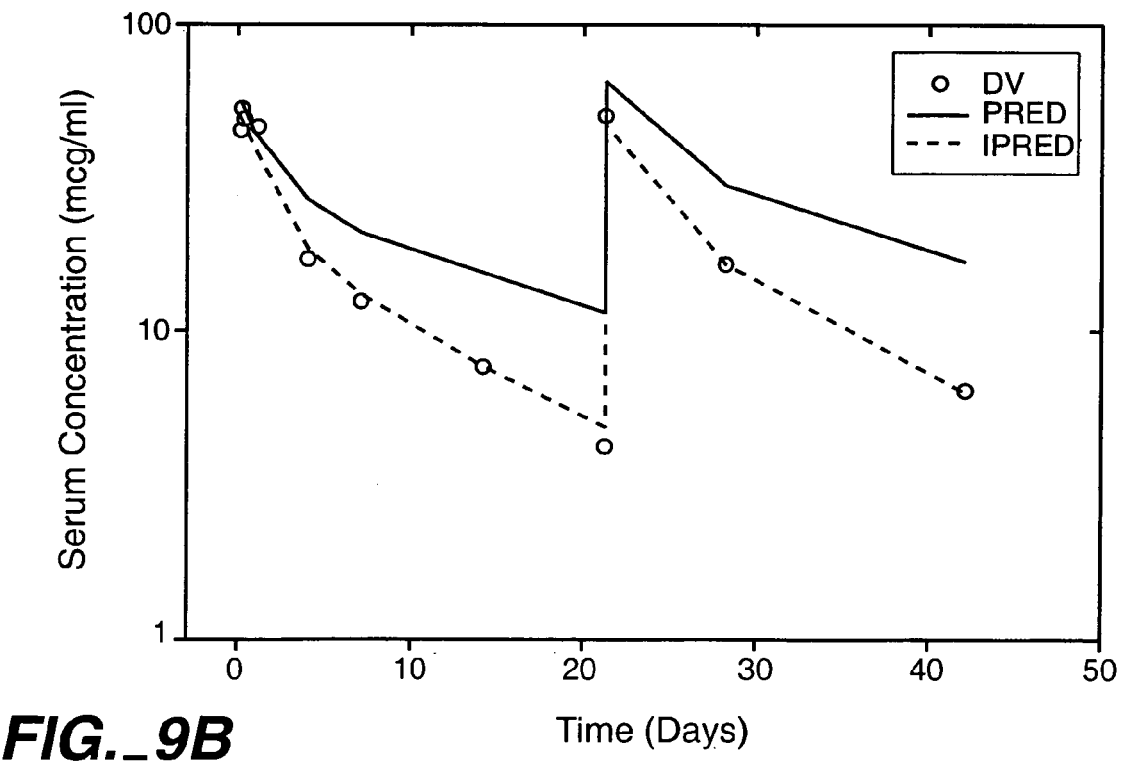
FIG._9B

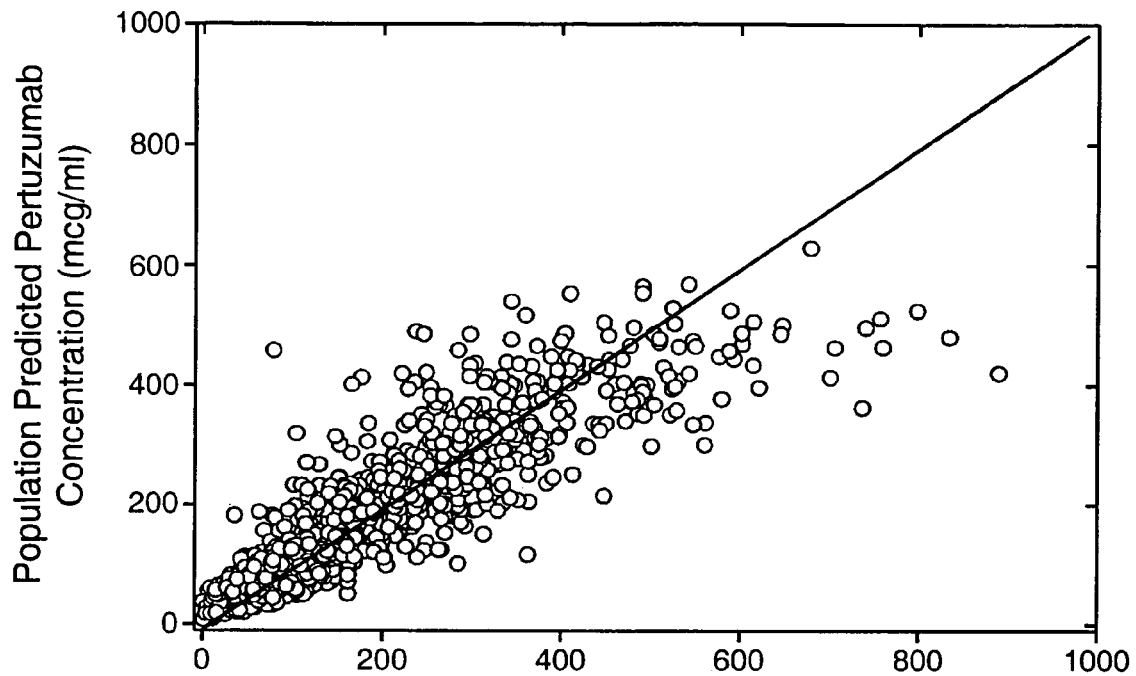
FIG._10A
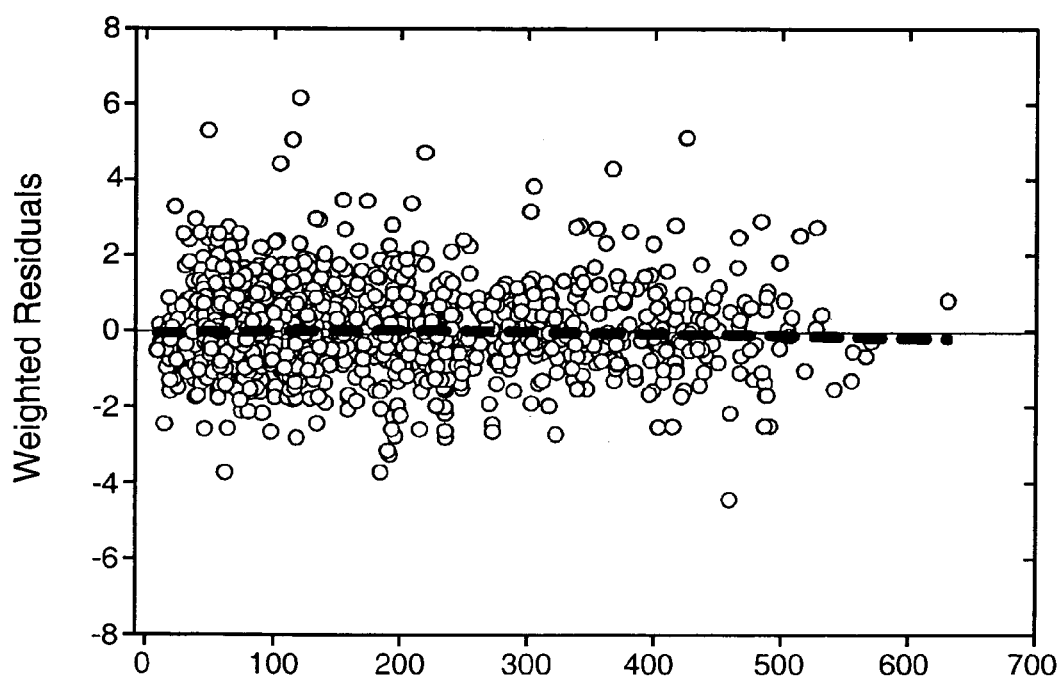
FIG._10B

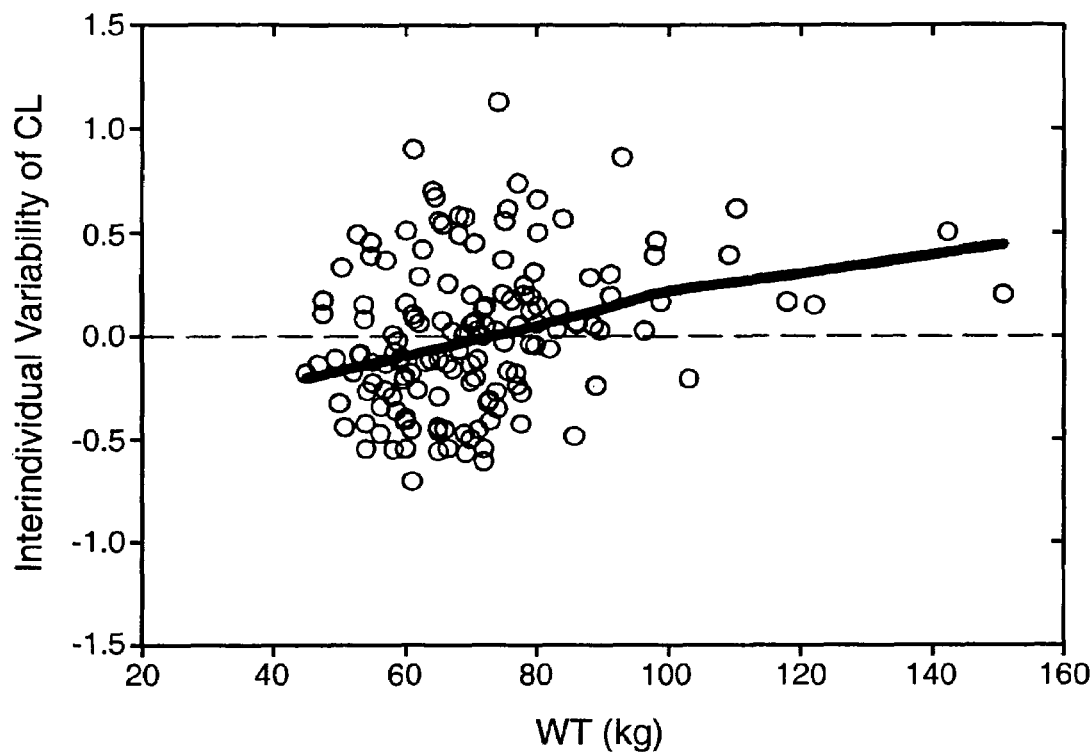
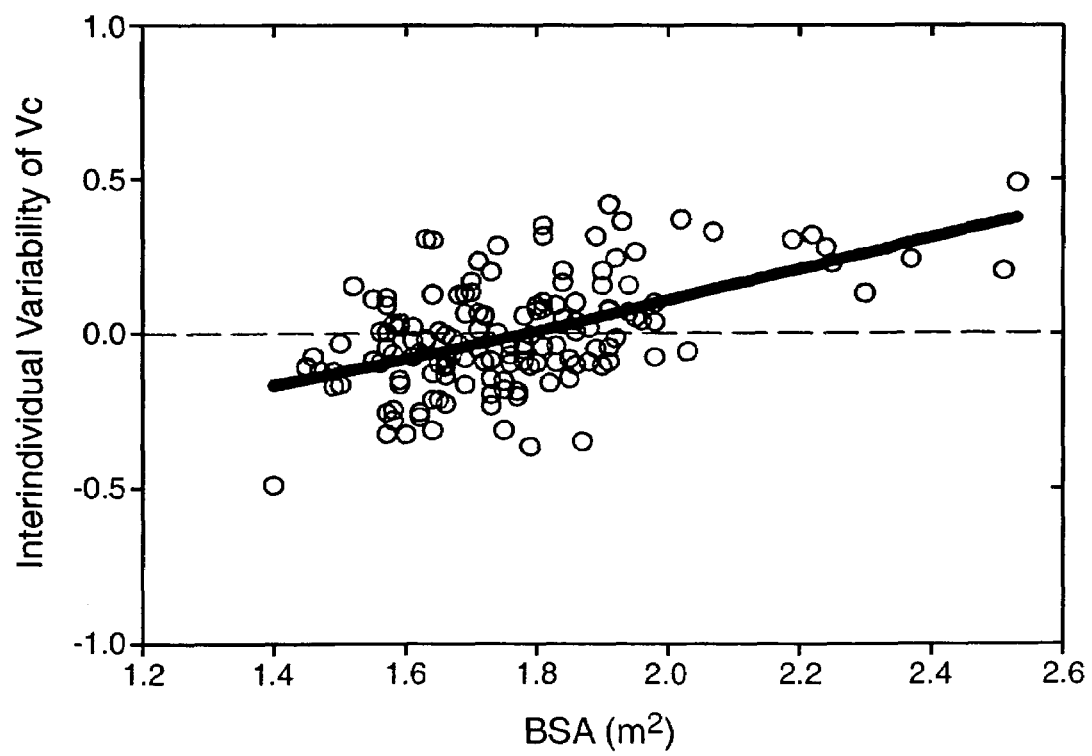
FIG._11A

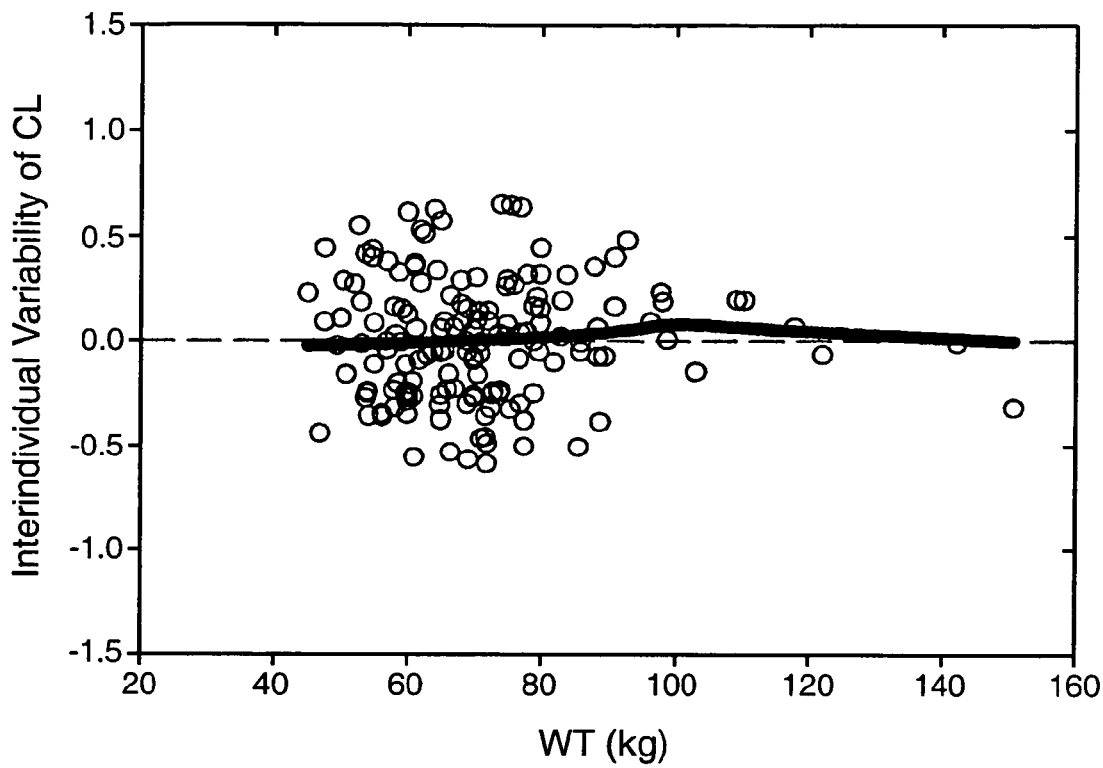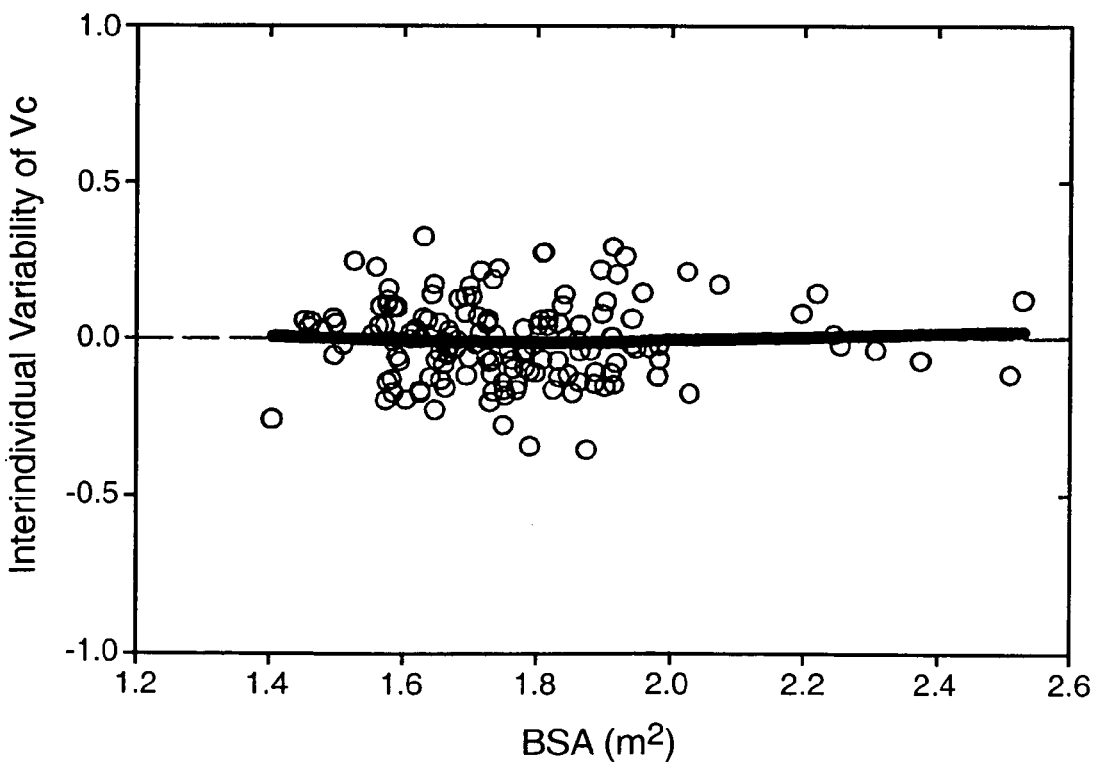
FIG._11B

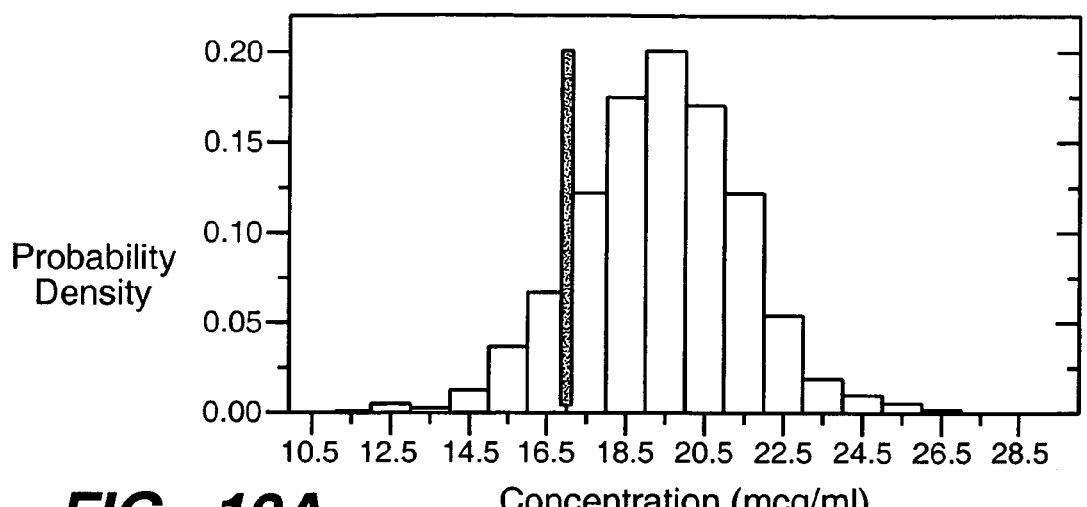
FIG._12A
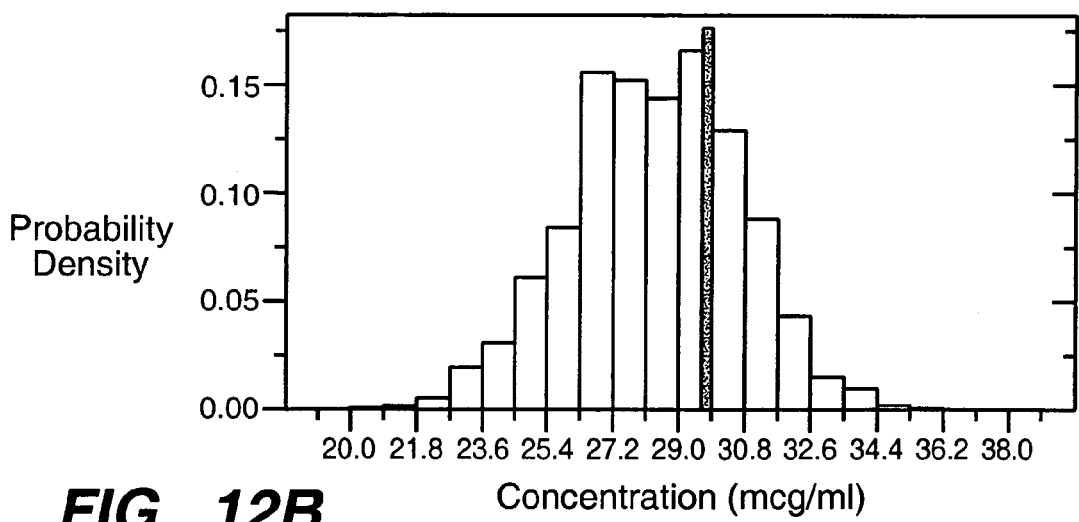
FIG._12B
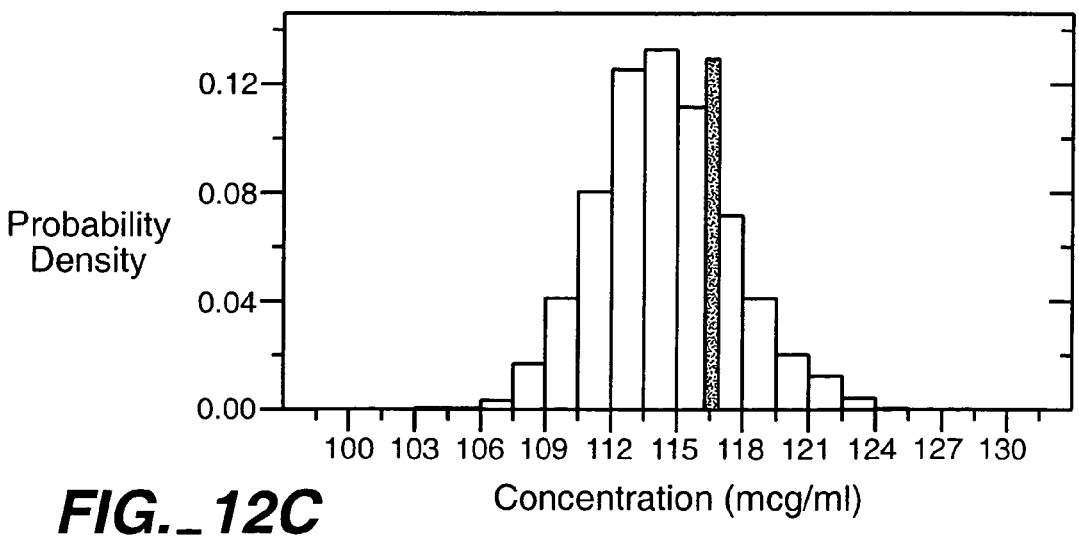
FIG._12C

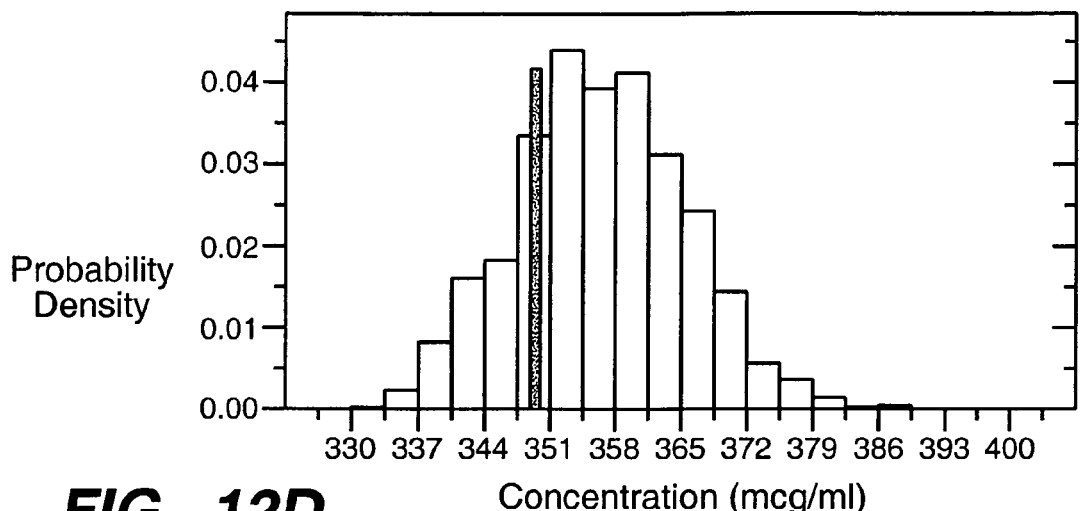
FIG._12D
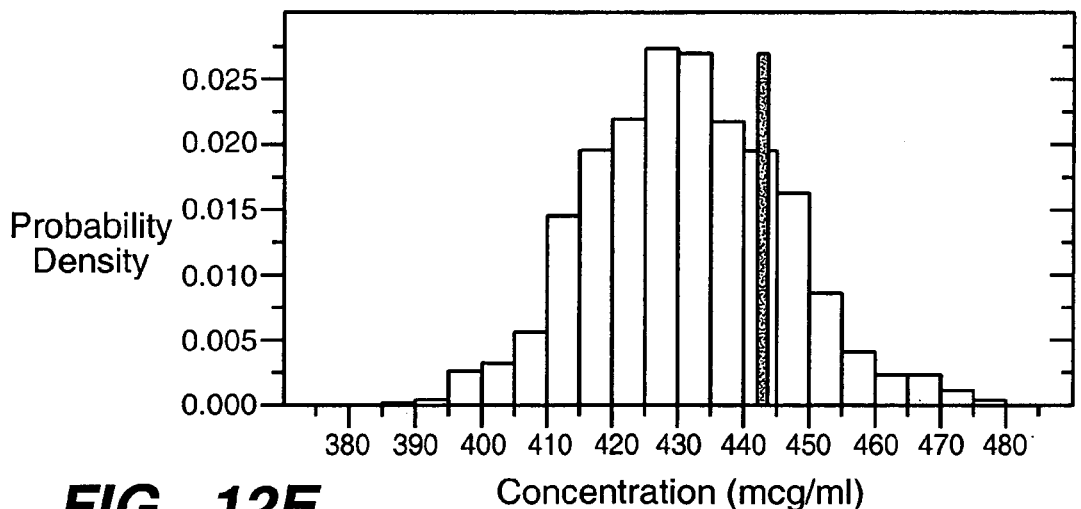
FIG._12E
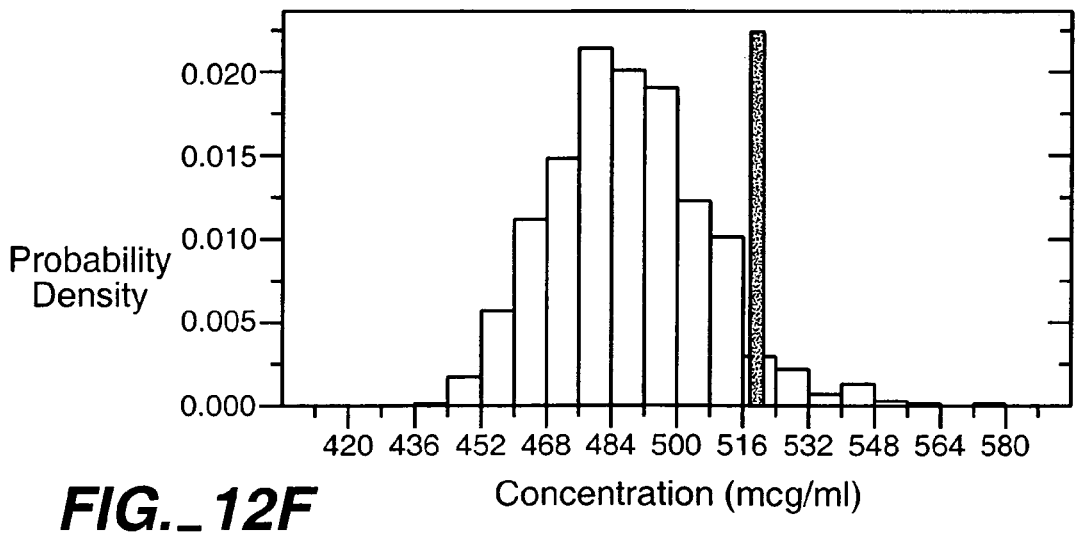
FIG._12F

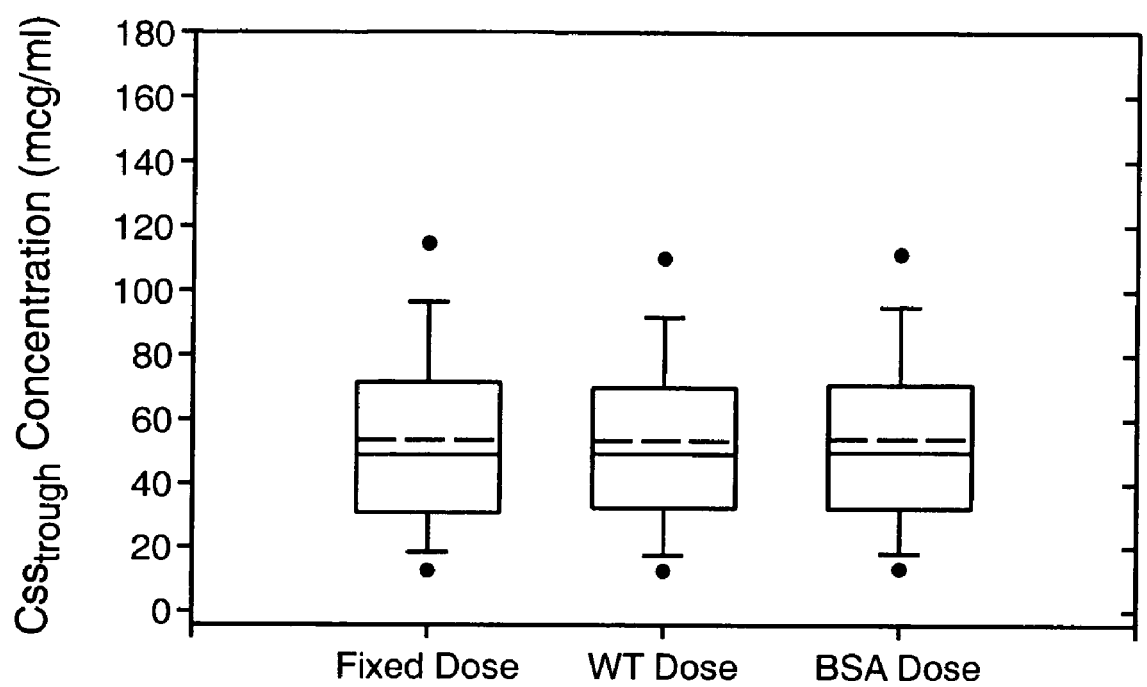
FIG._13

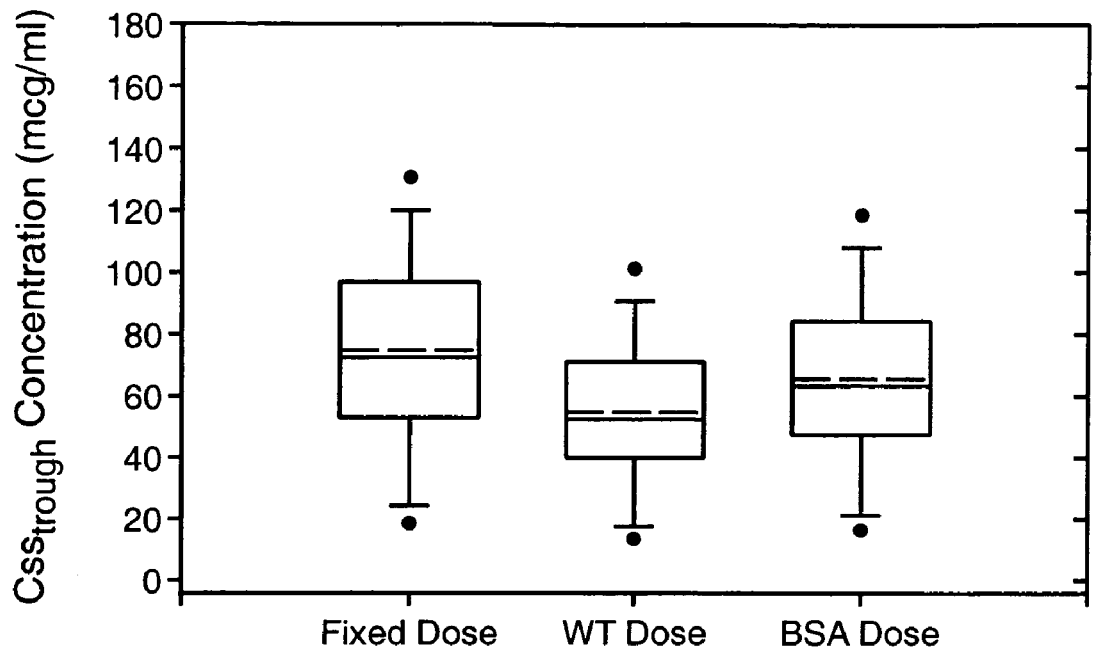
FIG._14A
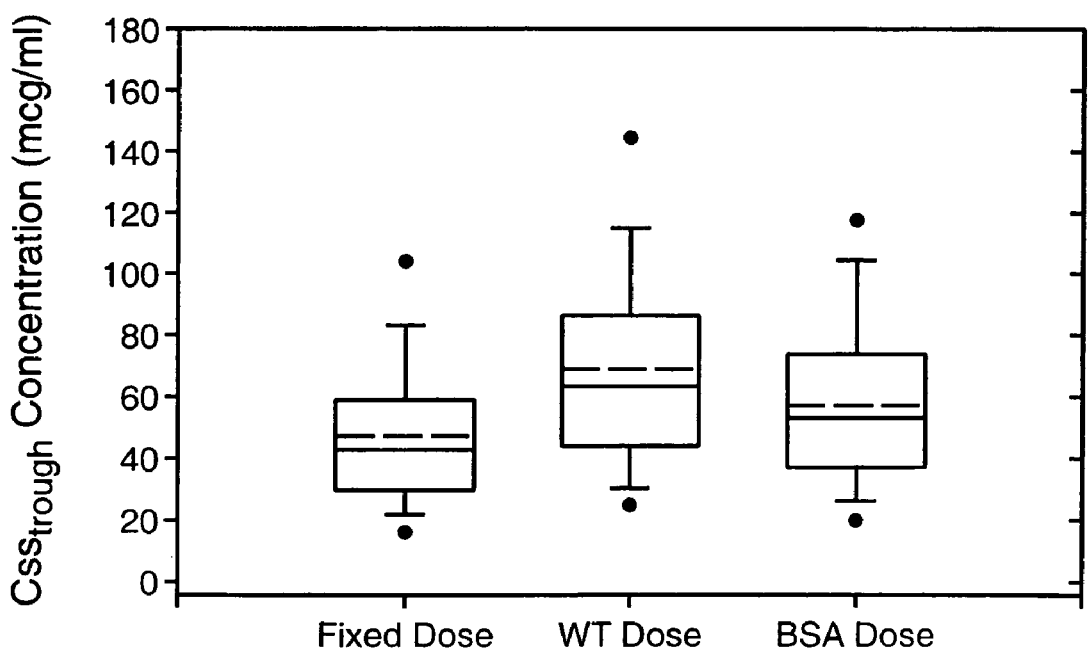
FIG._14B

FIXED DOSING OF HER ANTIBODIES

This is a non-provisional application filed under 37 CFR 1.53(b) claiming priority to provisional application 60/645,697 filed Jan. 21, 2005, the contents of which are incorporated herein by reference.

FIELD OF THE INVENTION

The present invention concerns fixed dosing of HER antibodies, such as pertuzumab.

BACKGROUND OF THE INVENTION

HER Receptors and Antibodies Thereagainst

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn, *Pharmac. Ther.* 64:127-154 (1994). Monoclonal antibodies directed against the EGFR or its ligands, TGF-α and EGF, have been evaluated as therapeutic agents in the treatment of such malignancies. See, e.g., Baselga and Mendelsohn, supra; Masui et al. *Cancer Research* 44:1002-1007 (1984); and Wu et al. *J. Clin. Invest.* 95:1897-1905 (1995).

The second member of the HER family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science*, 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet:* 1:765-767 (1986); Fukushige et al., *Mol Cell Biol.*, 6:955-958 (1986); Guerin et al., *Oncogene Res.*, 3:21-31 (1988); Cohen et al., *Oncogene*, 4:81-88 (1989); Yonemura et al., *Cancer Res.*, 51:1034 (1991); Borst et al., *Gynecol. Oncol.*, 38:364 (1990); Weiner et al., *Cancer Res.*, 50:421-425 (1990); Kern et al., *Cancer Res.*, 50:5184 (1990); Park et al., *Cancer Res.*, 49:6605 (1989); Zhau et al., *Mol. Carcinog.*, 3:254-257 (1990); Aasland et al. *Br. J. Cancer* 57:358-363 (1988); Williams et al., Pathobiology 59:46-52 (1991); and McCann et al., *Cancer*, 65:88-92 (1990). HER2 may be overexpressed in prostate cancer (Gu et al., *Cancer Lett.* 99:185-9 (1996); Ross et al., *Hum. Pathol.* 28:827-33 (1997); Ross et al., *Cancer* 79:2162-70 (1997); and Sadasivan et al., *J. Urol.* 150:126-31 (1993)).

Antibodies directed against the rat p185$^{neu}$ and human HER2 protein products have been described.

Drebin and colleagues have raised antibodies against the rat neu gene product, p185$^{neu}$ See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11 (3):117-127 (1991); Kumar et al. *Mol. Cell. Biol.* 1(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein.

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS* (USA) 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other HER receptor family members; HER3 (U.S. Pat. Nos. 5,183,884 and 5,480,968 as well as Kraus et al., *PNAS* (USA) 86:9193-9197 (1989)) and HER4 (EP Pat Appln No 599,274; Plowman et al., *Proc. Natl. Acad. Sci. USA*, 90:1746-1750 (1993); and Plowman et al., *Nature*, 366:473-

475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science*, 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional HER ligands were identified; neuregulin-2 (NRG-2) which is reported to bind either HER3 or HER4 (Chang et al. *Nature* 387 509-512 (1997); and Carraway et al *Nature* 387:512-516 (1997)); neuregulin-3 which binds HER4 (Zhang et al. *PNAS* (USA) 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.*, 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340(1995); Morrissey et al., *Proc. Natl. Acad. Sci. USA* 92: 1431-1435 (1995); and Lewis et al., *Cancer Res.*, 56:1457-1465 (1996) with respect to the HER2-HER3 protein complex. HER4, like HER3, forms an active signaling complex with HER2 (Carraway and Cantley, *Cell* 78:5-8 (1994)).

Patent publications related to HER antibodies include: U.S. Pat. No. 5,677,171, U.S. Pat. No. 5,720,937, U.S. Pat. No. 5,720,954, U.S. Pat. No. 5,725,856, U.S. Pat. No. 5,770,195, U.S. Pat. No. 5,772,997, U.S. Pat. No. 6,165,464, U.S. Pat. No. 6,387,371, U.S. Pat. No. 6,399,063, US2002/0192211A1, U.S. Pat. No. 6,015,567, U.S. Pat. No. 6,333,169, U.S. Pat. No. 4,968,603, U.S. Pat. No. 5,821,337, U.S. Pat. No. 6,054,297, U.S. Pat. No. 6,407,213, U.S. Pat. No. 6,719,971, U.S. Pat. No. 6,800,738, US2004/0236078A1, U.S. Pat. No. 5,648,237, U.S. Pat. No. 6,267,958, U.S. Pat. No. 6,685,940, U.S. Pat. No. 6,821,515, WO98/17797, U.S. Pat. No. 6,127,526, U.S. Pat. No. 6,333,398, U.S. Pat. No. 6,797,814, U.S. Pat. No. 6,339,142, U.S. Pat. No. 6,417,335, U.S. Pat. No. 6,489,447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. No. 6,627,196B 1, U.S. Pat. No. 6,632,979B 1, WO01/00244, US2002/0090662A1, WO01/89566, US2002/ 0064785, US2003/0134344, WO 04/24866, US2004/0082047, US2003/0175845A1, WO03/087131, US2003/0228663, WO2004/008099A2, US2004/0106161, WO2004/048525, US2005/0258685A1, U.S. Pat. No. 5,985,553, U.S. Pat. No. 5,747,261, U.S. Pat. No. 4,935,341, U.S. Pat. No. 5,401,638, U.S. Pat. No. 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. No. 5,571,894, U.S. Pat. No. 5,939,531, EP 502,812 B1, WO 93/03741, EP 554,441 B1, EP 656,367 A1, U.S. Pat. No. 5,288,477, U.S. Pat. No. 5,514,554, U.S. Pat. No. 5,587,458, WO 93/12220, WO 93/16185, U.S. Pat. No. 5,877,305, WO 93/21319, WO 93/21232, U.S. Pat. No. 5,856,089, WO 94/22478, U.S. Pat. No. 5,910,486, U.S. Pat. No. 6,028,059, WO 96/07321, U.S. Pat. No. 5,804,396, U.S. Pat. No. 5,846,749, EP 711,565, WO 96/16673, U.S. Pat. No. 5,783,404, U.S. Pat. No. 5,977,322, U.S. Pat. No. 6,512,097, WO 97/00271, U.S. Pat. No. 6,270,765, U.S. Pat. No. 6,395,272, U.S. Pat. No. 5,837,243, WO 96/40789, U.S. Pat. No. 5,783,186, U.S. Pat. No. 6,458,356, WO 97/20858, WO 97/38731, U.S. Pat. No. 6,214,388, U.S. Pat. No. 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. No. 5,705,157, U.S. Pat. No. 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842 and WO 03/86467.

Diagnostics

Patients treated with the HER2 antibody trastuzumab are selected for therapy based on HER2 overexpression/amplification. See, for example, WO99/31140 (Paton et al.), US2003/0170234A1 (Hellmann, S.), and US2003/0147884 (Paton et al.); as well as WO01/89566, US2002/0064785, and US2003/0134344 (Mass et al.). See, also, US2003/0152987, Cohen et al., concerning immunohistochemistry (IHC) and fluorescence in situ hybridization (FISH) for detecting HER2 overexpression and amplification.

WO2004/053497 (Bacus et al.) refers to determining or predicting response to HERCEPTIN® therapy. US2004/013297A1 (Bacus et al.) concerns determining or predicting response to ABX0303 EGFR antibody therapy. WO2004/000094 (Bacus et al.) is directed to determining response to GW572016, a small molecule, EGFR-HER2 tyrosine kinase inhibitor. WO2004/063709, Amler et al., refers to biomarkers and methods for determining sensitivity to EGFR inhibitor, erlotinib HCl. US2004/0209290, Cobleigh et al., concerns gene expression markers for breast cancer prognosis.

Patients treated with pertuzumab can be selected for therapy based on HER activation or dimerization. Patent publications concerning pertuzumab and selection of patients for therapy therewith include: WO01/00245 (Adams et al.); US2003/0086924 (Sliwkowski, M.); US2004/0013667A1 (Sliwkowski, M.); as well as WO2004/008099A2, and US2004/0106161 (Bossenmaier et al.).

Cronin et al., *Am. J. Path.* 164(1): 35-42 (2004) describes measurement of gene expression in archival paraffin-embedded tissues. Ma et al. *Cancer Cell* 5:607-616 (2004) describes gene profiling by gene oliogonucleotide microarray using isolated RNA from tumor-tissue sections taken from archived primary biopsies.

Dosing of Anticancer Drugs and HER Antibodies

Papers discussing dosing of anticancer drugs include: Egorin, M. *J Clin Oncol* 2003; 21:182-3 (2003); Baker et al. *J Natl Cancer Inst* 94:1883-8 (2002); Felici et al. *Eur J Cancer* 38:1677-84 (2002); Loos et al. *Clin. Cancer Res.* 6:2685-9(2000); de Jongh et al. *J. Clin Oncol.* 19:3733-9 (2001); Mathijssen et al. *J. Clin Oncol.* 20:81-7 (2002); and de Jong et al. *Clin Cancer Res* 10:4068-71 (2004).

Typically, commercially available humanized IgG monoclonal antibodies (i.e. trastuzumab, and bevacizumab, Genentech Inc., South San Francisco and gemtuzumab ozogomicin, Wyeth Pharmaceuticals, Philadelphia) and cytotoxic small molecule drugs in oncology have been administered on a weight -based (mg/kg) or body surface area-based (BSA) dosing method.

Cetuximab (ERBITUX®) is an antibody that binds EGF receptor and is approved for therapy of colorectal cancer. In colorectal cancer, cetuximab 400 mg/m2 is given as a loading dose by intravenous infusion over 2 hours. This is followed by once weekly maintenance doses of 250 mg/m2 given over 1 hour. See cetuximab prescribing information.

Trastuzumab (HERCEPTIN®) is administered to patients with metastatic breast cancer as a 4 mg/kg loading dose, followed by weekly 2 mg/kg doses. See trastuzumab prescribing information.

See, also, WO99/31140; US2003/0147884A1; US2003/0170234A1; US2005/0002928A1; WO00/69460; WO01/15730 and U.S. Pat. No. 6,627,196B1 concerning trastuzumab dosing.

Pertuzumab (also known as recombinant human monoclonal antibody 2C4; OMNITARG™, Genentech, mc, South San Francisco) represents the first in a new class of agents known as HER dimerization inhibitors (HDI) and functions to inhibit the ability of HER2 to form active heterodimers with other HER receptors (such as EGFR/HER1, HER3 and HER4) and is active irrespective of HER2 expression levelsEN.REFLIST. See, for example, Harari and Yarden Oncogene 19:6102-14 (2000); Yarden and Sliwkowski. *Nat Rev Mol Cell Biol* 2:127-37 (2001); Sliwkowski *Nat Struct Biol* 10:158-9 (2003); Cho etal. *Nature* 421:756-60 (2003); and Malik et al. *Pro Am Soc Cancer Res* 44:176-7 (2003).

Pertuzumab blockade of the formation of HER2-HER3 heterodimers in tumor cells has been demonstrated to inhibit critical cell signaling, which results in reduced tumor proliferation and survival (Agus et al. *Cancer Cell* 2:127-37 (2002)).

Pertuzumab has undergone testing as a single agent in the clinic with a phase Ia trial in patients with advanced cancers and phase II trials in patients with ovarian cancer and breast cancer as well as lung and prostate cancer. In a Phase I study, patients with incurable, locally advanced, recurrent or metastatic solid tumors that had progressed during or after standard therapy were treated with pertuzumab given intravenously every 3 weeks. Pertuzumab was generally well tolerated. Tumor regression was achieved in 3 of 20 patients evaluable for response. Two patients had confirmed partial responses. Stable disease lasting for more than 2.5 months was observed in 6 of 21 patients (Agus et al. *Pro Am Soc Clin Oncol* 22:192 (2003)). At doses of 2.0-15 mg/kg, the pharmacokinetic of pertuzumab was linear, and mean clearance ranged from 2.69 to 3.74 mL/day/kg and the mean terminal elimination half-life ranged from 15.3 to 27.6 days. Antibodies to pertuzumab were not detected (Allison et al. *Pro Am Soc Clin Oncol* 22:197 (2003)). Pertuzumab was dosed on a weight-basis (mg/kg) in the Phase I trial. Phase II trials have been initiated using a fixed-dose.

SUMMARY OF THE INVENTION

The present invention provides the first critical assessment of the impact and utility of fixed dosing of a humanized IgG1 monoclonal antibody on pharmacokinetics and target drug concentrations. The primary objectives of this analysis of the HER antibody pertuzumab were to: 1) evaluate the population pharmacokinetic and predictive covariates for pertuzumab in cancer patients, and 2) examine the variability of steady-state trough concentrations and exposures after fixed, or body weight-, and body surface area (BSA)-based dosing.

Accordingly, in a first aspect, the invention provides a method for treating cancer comprising administering one or more fixed dose(s) of a HER antibody to a human patient in an amount effective to treat the cancer.

In another aspect, the invention provides a method of treating cancer in a human patient comprising administering at least one fixed dose of pertuzumab to the patient, wherein the fixed dose is selected from the group consisting of approximately 420 mg, approximately 525 mg, approximately 840 mg, and approximately 1050 mg of pertuzumab.

The invention also concerns an article of manufacture comprising a vial containing a fixed dose of a HER antibody, wherein the fixed dose is selected from the group consisting of approximately 420 mg, approximately 525 mg, approximately 840 mg, and approximately 1050 mg of the HER antibody.

BRIEF DESCRIPTION OF THE DRAWINGS

FIG. 1 provides a schematic of the HER2 protein structure, and amino acid sequences for Domains I-IV (SEQ ID Nos.19-22, respectively) of the extracellular domain thereof.

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 1 and 2, respectively); $V_L$ and $V_H$ domains of humanized 2C4 version 574 (SEQ ID Nos. 3 and 4, respectively), and human $V_L$ and $V_H$ consensus frameworks (hum κ1, light kappa subgroup I; humIII, heavy subgroup III) (SEQ ID Nos. 5 and 6, respectively). Asterisks identify differences between humanized 2C4 version 574 and murine monoclonal antibody 2C4 or between humanized 2C4 version 574 and the human framework. Complementarity Determining Regions (CDRs) are in brackets.

FIGS. 3A and 3B show the amino acid sequences of pertuzumab light chain and heavy chain (SEQ ID Nos. 13 and 14, respectively). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIG. 4 depicts, schematically, binding of 2C4 at the heterodimeric binding site of HER2, thereby preventing heterodimerization with activated EGFR or HER3. FIG. 5 depicts coupling of HER2/HER3 to the MAPK and Akt pathways.

FIG. 6 compares various activities of trastuzumab and pertuzumab.

FIGS. 7A and 7B show the amino acid sequences of trastuzumab light chain (FIG. 7A; SEQ ID No. 15) and heavy chain (FIG. 7B; SEQ ID No. 16), respectively.

FIGS. 8A and 8B depict a variant pertuzumab light chain sequence (FIG. 8A; SEQ ID No. 17) and a variant pertuzumab heavy chain sequence (FIG. 8B; SEQ ID No. 18), respectively.

FIGS. 9A and 9B are representative profiles of a single subject's PK data fitted by a one-(FIG. 9A) or two-(FIG. 9B) compartmental model. Open circles indicate observed concentration. Solid and dotted lines indicate population predicted and individual predicted concentration, respectively.

FIGS. 10A and 10B represent model diagnostic plots. FIG. 10A depicts observed versus predicted pertuzumab concentrations. The solid line is the line of unity. FIG. 10B depicts weighted residuals versus predicted pertuzumab concentrations. The dashed line is a LOESS smooth of data.

FIGS. 11A and 11B depict random effect ($\eta$) for clearance (CL) by weight (WT) and volume at the central compartment (Vc) by body surface area (BSA) for the base model (FIG. 11A) and final model (FIG. 11B).

FIGS. 12A-F show model evaluation of pertuzumab final population pharmacokinetic model using a posterior model check. Posterior predictive distribution and observed values for the test statistics: FIG. 12A-$2.5^{th}$; FIG. 12B-$5^{th}$; FIG. 12C-$50^{th}$, FIG. 12D-$90^{th}$, FIG. 12E-$95^{th}$, FIG. 12F-$97.5^{th}$. The vertical line on each histogram represents the observed value of the test statistic.

FIG. 13 illustrates the predicted pertuzumab steady state trough concentration (Day 84) after a fixed, weight (WT) or BSA-based dose for 1000 simulated subjects bootstrapped from original pharmacokinetic (PK) dataset according to the final model.

FIGS. 14A and 14B show the predicted pertuzumab steady state trough concentration (day 84) after a fixed, weight (WT) or BSA-based dose for patient populations with $\leq 10^{th}$ (50.4 kg) (FIG. 14A) or $\geq 90^{th}$ (88.5 kg) (FIG. 14B)WT values.

DETAILED DESCRIPTION OF THE PREFERRED EMBODIMENTS

I. Definitions

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m$^2$ dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks.

A "HER receptor" is a receptor protein tyrosine kinase which belongs to the HER receptor family and includes EGFR, HER2, HER3 and HER4 receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is native sequence human HER receptor.

The terms "ErbB1," "HER1", "epidermal growth factor receptor" and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Humphrey et al. *PNAS (USA)* 87:4207-4211 (1990)). erbB1 refers to the gene encoding the EGFR protein product.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred HER2 is native sequence human HER2.

The extracellular domain of HER2 comprises four domains: "Domain I" (amino acid residues from about 1-195; SEQ ID NO:19), "Domain II" (amino acid residues from about 196-319; SEQ ID NO:20), "Domain III" (amino acid residues from about 320-488: SEQ ID NO:21), and "Domain IV" (amino acid residues from about 489-630; SEQ ID NO:22) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), and Plowman et al. *Proc. Natl. Acad. Sci.* 90:1746-1750 (1993), as well as FIG. 1 herein.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989).

The terms "ErbB4" and "HER4" herein refer to the receptor polypeptide as disclosed, for example, in EP Pat Appln No 599,274; Plowman et al., *Proc. Natl. Acad. Sci. USA*, 90:1746-1750 (1993); and Plowman et al., *Nature*, 366:473-475 (1993), including isoforms thereof, e.g., as disclosed in WO99/19488, published Apr. 22, 1999.

By "HER ligand" is meant a polypeptide which binds to and/or activates a HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)); and cripto (CR-1) (Kannan et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4, and heregulins.

"Heregulin" (HRG) when used herein refers to a polypeptide encoded by the heregulin gene product as disclosed in U.S. Pat. No. 5,641,869, or Marchionni et al., *Nature,* 362: 312-318 (1993). Examples of heregulins include heregulin-α, heregulin-β1, heregulin-β2 and heregulin-β3 (Holmes et al., *Science,* 256:1205-1210 (1992); and U.S. Pat. No. 5,641, 869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)).

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.,* 269(20):14661-14665 (1994), for example. Examples of such HER dimers include EGFR-HER2, HER2-HER3 and HER3-HER4 heterodimers. Moreover, the HER dimer may comprise two or more HER2 receptors combined with a different HER receptor, such as HER3, HER4 or EGFR. Other proteins, such as a cytokine receptor subunit (e.g. gp130) may be associated with the dimer.

A "HER inhibitor" is an agent which interferes with HER activation or function. Examples of HER inhibitors include HER antibodies (e.g. EGFR, HER2, HER3, or HER4 antibodies); EGFR-targeted drugs; small molecule HER antagonists; HER tyrosine kinase inhibitors; HER2 and EGFR dual tyrosine kinase inhibitors such as lapatinib/GW572016; antisense molecules (see, for example, WO2004/87207); and/or agents that bind to, or interfere with function of, downstream signaling molecules, such as MAPK or Akt (see FIG. 5). Preferably, the HER inhibitor is an antibody or small molecule which binds to a HER receptor.

A "HER antibody" is an antibody that binds to a HER receptor. Optionally, the HER antibody further interferes with HER activation or function. Preferably, the HER antibody binds to the HER2 receptor. A HER2 antibody of particular interest herein is pertuzumab. Another example of a HER2 antibody is trastuzumab. Examples of EGFR antibodies include cetuximab and ABX0303.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases. See, FIG. 5, for example.

"Phosphorylation" refers to the addition of one or more phosphate group(s) to a protein, such as a HER receptor, or substrate thereof.

An antibody which "inhibits HER dimerization" is an antibody which inhibits, or interferes with, formation of a HER dimer. Preferably, such an antibody binds to HER2 at the heterodimeric binding site thereof. The most preferred dimerization inhibiting antibody herein is pertuzumab or MAb 2C4. Binding of 2C4 to the heterodimeric binding site of HER2 is illustrated in FIG. 4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; and antibodies which bind to HER4 and inhibit dimerization thereof with one or more other HER receptors.

An antibody which "inhibits HER dimerization more effectively than trastuzumab" is one which reduces or eliminates HER dimers more effectively (for example at least about 2-fold more effectively) than trastuzumab. Preferably, such an antibody inhibits HER2 dimerization at least about as effectively as an antibody selected from the group consisting of murine monoclonal antibody 2C4, a Fab fragment of murine monoclonal antibody 2C4, pertuzumab, and a Fab fragment of pertuzumab. One can evaluate HER dimerization inhibition by studying HER dimers directly, or by evaluating HER activation, or downstream signaling, which results from HER dimerization, and/or by evaluating the antibody-HER2 binding site, etc. Assays for screening for antibodies with the ability to inhibit HER dimerization more effectively than trastuzumab are described in Agus et al. *Cancer Cell* 2: 127-137 (2002) and WO01/00245 (Adams et al.). By way of example only, one may assay for inhibition of HER dimerization by assessing, for example, inhibition of HER dimer formation (see, e.g., FIG. 1A-B of Agus et al. *Cancer Cell* 2: 127-137 (2002); and WO01/00245); reduction in HER ligand activation of cells which express HER dimers (WO01/00245 and FIG. 2A-B of Agus et al. *Cancer Cell* 2: 127-137 (2002), for example); blocking of HER ligand binding to cells which express HER dimers (WO01/00245, and FIG. 2E of Agus et al. *Cancer Cell* 2: 127-137 (2002), for example); cell growth inhibition of cancer cells (e.g. MCF7, MDA-MD-134, ZR-75-1, MD-MB-175, T47D cells) which express HER dimers in the presence (or absence) of HER ligand (WO01/00245 and FIGS. 3A-D of Agus et al. *Cancer Cell* 2: 127-137 (2002), for instance); inhibition of downstream signaling (for instance, inhibition of HRG-dependent AKT phosphorylation or inhibition of HRG- or TGFα-dependent MAPK phosphorylation) (see, WO01/00245, and FIG. 2C-D of Agus et al. *Cancer Cell* 2: 127-137 (2002), for example). One may also assess whether the antibody inhibits HER dimerization by studying the antibody-HER2 binding site, for instance, by evaluating a structure or model, such as a crystal structure, of the antibody bound to HER2 (See, for example, Franklin et al. *Cancer Cell* 5:317-328 (2004)).

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2. Franklin et al. *Cancer Cell* 5:317-328 (2004).

The HER2 antibody may "inhibit HRG-dependent AKT phosphorylation" and/or inhibit "HRG- or TGFα-dependent MAPK phosphorylation" more effectively (for instance at least 2-fold more effectively) than trastuzumab (see Agus et al. *Cancer Cell* 2: 127-137 (2002) and WO01/00245, by way of example).

The HER2 antibody may be one which does "not inhibit HER2 ectodomain cleavage" (Molina et al. *Cancer Res.* 61:4744-4749(2001)).

A HER2 antibody that "binds to a heterodimeric binding site" of HER2, binds to residues in domain II (and optionally also binds to residues in other of the domains of the HER2 extracellular domain, such as domains I and III), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II and optionally residues in other domain(s) of HER2, such as domains I and III. Preferably the antibody that binds to domain II binds to the junction between domains I, II and III of HER2.

A "native sequence" polypeptide is one which has the same amino acid sequence as a polypeptide (e.g., HER receptor or HER ligand) derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256:495 (1975); Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681, (Elsevier, N.Y., 1981)), recombinant DNA methods (see, e.g., U.S. Pat. No. 4,816,567), phage display technologies (see, e.g., Clackson et al., *Nature*, 352:624-628 (1991); Marks et al., *J. Mol. Biol.*, 222: 581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); and Lonberg and Huszar, *Intern. Rev. Immunol.*, 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact antibody" herein is one which comprises two antigen binding regions, and an Fc region. Preferably, the intact antibody has one or more effector functions.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Antibody "effector functions" refer to those biological activities attributable to an Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)), and regulates homeostasis of immunoglobulins.

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, Curr. Op. Struct. Biol. 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or trastuzumab (HERCEPTIN®) as described in Table 3 of U.S. Pat. No. 5,821,337 expressly incorporated herein by reference; humanized 520C9 (WO93/21319); and humanized 2C4 antibodies as described herein.

For the purposes herein, "trastuzumab," "HERCEPTIN®," and "huMAb4D5-8" refer to an antibody comprising the light and heavy chain amino acid sequences in SEQ ID NOS. 15 and 16, respectively.

Herein, "pertuzumab" and "OMNITARG™" refer to an antibody comprising the light and heavy chain amino acid sequences in SEQ ID NOS. 13 and 14, respectively.

Differences between trastuzumab and pertuzumab functions are illustrated in FIG. 6.

A "naked antibody" is an antibody that is not conjugated to a heterologous molecule, such as a cytotoxic moiety or radiolabel.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by $V_H$ and $V_L$ domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al., *J. Mol. Biol.* 226:889-896 (1992).

The term "main species antibody" herein refers to the antibody structure in a composition which is the quantitatively predominant antibody molecule in the composition. In one embodiment, the main species antibody is a HER2 antibody, such as an antibody that binds to Domain II of HER2, antibody that inhibits HER dimerization more effectively than trastuzumab, and/or an antibody which binds to a heterodimeric binding site of HER2. The preferred embodiment herein of the main species antibody is one comprising the variable light and variable heavy amino acid sequences in SEQ ID Nos. 3 and 4, and most preferably comprising the light chain and heavy chain amino acid sequences in SEQ ID Nos. 13 and 14 (pertuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include acidic variant (e.g. deamidated antibody variant), basic variant, the antibody with an amino-terminal leader extension (e.g. VHS–) on one or two light chains thereof, antibody with a C-terminal lysine residue on one or two heavy chains thereof, etc, and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moeities attached thereto which differ from one or more carbohydate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Where the antibody has an Fc region, an oligosaccharide structure such as that shown in FIG. 9 herein may be attached to one or two heavy chains of the antibody, e.g. at residue 299 (298, Eu numbering of residues). For pertuzumab, G0 was the predominant oligosaccharide structure, with other oligosaccharide structures such as G0-F, G-1, Man5, Man6, G1-1, G1(1-6), G1(1-3) and G2 being found in lesser amounts in the pertuzumab composition.

Unless indicated otherwise, a "G1 oligosaccharide structure" herein includes G-1, G1-1, G1(1-6) and G1(1-3) structures.

An "amino-terminal leader extension" herein refers to one or more amino acid residues of the amino-terminal leader sequence that are present at the amino-terminus of any one or more heavy or light chains of an antibody. An exemplary amino-terminal leader extension comprises or consists of three amino acid residues, VHS, present on one or both light chains of an antibody variant.

A "deamidated" antibody is one in which one or more asparagine residues thereof has been derivitized, e.g. to an aspartic acid, a succinimide, or an iso-aspartic acid.

The terms "cancer" and "cancerous" refer to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer.

Herein, a "patient" is a human patient. The patient may be a "cancer patient," i.e. one who is suffering or at risk for suffering from one or more symptoms of cancer, or other patient who could benefit from therapy with a HER antibody.

A "biological sample" refers to a sample, generally cells or tissue derived from a biological source.

A "patient sample" refers to a sample obtained from a patient, such as a cancer patient.

A "tumor sample" herein is a sample derived from, or comprising tumor cells from, a patient's tumor. Examples of tumor samples herein include, but are not limited to, tumor biopsies, circulating tumor cells, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

A "fixed" tumor sample is one which has been histologically preserved using a fixative.

A "formalin-fixed" tumor sample is one which has been preserved using formaldehyde as the fixative.

An "embedded" tumor sample is one surrounded by a firm and generally hard medium such as paraffin, wax, celloidin, or a resin. Embedding makes possible the cutting of thin sections for microscopic examination or for generation of tissue microarrays (TMAs).

A "paraffin-embedded" tumor sample is one surrounded by a purified mixture of solid hydrocarbons derived from petroleum.

Herein, a "frozen" tumor sample refers to a tumor sample which is, or has been, frozen.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor. Such activation can be determined directly (e.g. by measuring HER phosphorylation) or indirectly (e.g. by gene expression profiling or by detecting HER heterodimers, as described herein).

A cancer with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR)

techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which "does not overexpress or amplify HER receptor" is one which does not have higher than normal levels of HER receptor protein or gene compared to a noncancerous cell of the same tissue type. Antibodies that inhibit HER dimerization, such as pertuzumab, may be used to treat cancer which does not overexpress or amplify HER2 receptor.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 µg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the HER2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Examples of HER2 antibodies that induce apoptosis are 7C2 and 7F3.

The "epitope 2C4" is the region in the extracellular domain of HER2 to which the antibody 2C4 binds. In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds to the 2C4 epitope of HER2. Epitope 2C4 comprises residues from Domain II in the extracellular domain of HER2. 2C4 and pertuzumab binds to the extracellular domain of HER2 at the junction of domains I, II and III. Franklin et al. *Cancer Cell* 5:317-328 (2004).

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive of the HER2 ECD, residue numbering including signal peptide).

The "epitope 7C2/7F3" is the region at the N terminus, within Domain I, of the extracellular domain of HER2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on HER2 (e.g. any one or more of residues in the region from about residue 22 to about residue 53 of the HER2 ECD, residue numbering including signal peptide).

"Treatment" refers to both therapeutic treatment and prophylactic or preventative measures. Those in need of treatment include those already with the disease as well as those in which the disease is to be prevented. Hence, the patient to be treated herein may have been diagnosed as having the disease or may be predisposed or susceptible to the disease.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete respose, CR), increase overall survival time, and/or improve one or more symptoms of cancer (e.g. as assessed by FOSI).

"Overall survival" refers to the patient remaining alive for a defined period of time, such as 1 year, 5 years, etc, e.g., from the time of diagnosis or treatment.

"Progression free survival" refers to the patient remaining alive, without the cancer getting worse. An "objective response" refers to a measurable response, including complete response (CR) or partial response (PR).

By "complete response" or "complete remission" is intended the disappearance of all signs of cancer in response to treatment. This does not always mean the cancer has been cured.

"Partial response" refers to a decrease in the size of one or more tumors or lesions, or in the extent of cancer in the body, in response to treatment.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S—I and capecitabine, and thymidylate synthase inhibitors and glycinamide ribonucleotide formyltransferase inhibitors such as raltitrexed (TOMUDEX®, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)- imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

An "antimetabolite chemotherapeutic agent" is an agent which is structurally similar to a metabolite, but can not be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOME®), azocytosine, deoxycytosine, pyridmidene, fludarabine (FLUDARA®), cladrabine, 2-deoxy-D-glucose etc. The preferred antimetabolite chemotherapeutic agent is gemcitabine.

"Gemcitabine" or "2'-deoxy-2',2'-difluorocytidine monohydrochloride (b-isomer)" is a nucleoside analogue that exhibits antitumor activity. The empirical formula for gemcitabine HCl is C9H11F2N3O4.HCl. Gemcitabine HCl is sold by Eli Lilly under the trademark GEMZAR®.

A "platinum-based chemotherapeutic agent" comprises an organic compound which contains platinum as an integral part of the molecule. Examples of platinum-based chemotherapeutic agents include carboplatin, cisplatin, and oxaliplatinum.

By "platinum-based chemotherapy" is intended therapy with one or more platinum-based chemotherapeutic agents, optionally in combination with one or more other chemotherapeutic agents.

By "platinum resistant" cancer is meant that the cancer patient has progressed while receiving platinum-based chemotherapy (i.e. the patient is "platinum refractory"), or the patient has progressed within 12 months (for instance, within 6 months) after completing a platinum-based chemotherapy regimen;

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to vascular endothelial growth factor (VEGF), such as bevacizumab (AVASTIN®).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. Eur. J. Cancer 32A:636-640 (1996)); and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH). Examples of small molecules that bind to EGFR include ZD1839 or Gefitinib (IRESSA™; Astra Zeneca); CP-358774 or Erlotinib HCL (TARCEVA™; Genentech/OSI); and AG 1478, AG1571 (SU 5271; Sugen).

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; dual-HER inhibitors such as EKB-569 (available from Wyeth) which preferentially binds EGFR but inhibits both HER2 and EGFR-overexpressing cells; GW572016 (available from Glaxo) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (Gleevac™) available from Glaxo; MAPK extracellular regulated kinase 1 inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804, 396; WO99/09016 (American Cyanimid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions and responses, allergic reaction, eczema including allergic or atopic eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa/periarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex -mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis (LIP), bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, diabetic nephropathy, Dressier's syndrome, alopecia greata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird -fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalniitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antobodies, non-malignant thymoma, vitiligo, SCID and Epstein-Barr virus-associated diseases, acquired immune deficiency syndrome (AIDS), parasitic diseases such as Lesihmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, lyniphadenitis, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

A "benign hyperproliferative disorder" is meant a state in a patient that relates to cell proliferation and which is recognized as abnormal by members of the medical community. An abnormal state is characterized by a level of a property that is statistically different from the level observed in organisms not suffering from the disorder. Cell proliferation refers to growth or extension by multiplication of cells and includes cell division. The rate of cell proliferation may be measured by counting the number of cells produced in a given unit of time. Examples of benign hyperproliferative disorders include psoriasis and polyps.

A "respiratory disease" involves the respiratory system and includes chronic bronchitis, asthma including acute asthma and allergic asthma, cystic fibrosis, bronchiectasis, allergic or other rhinitis or sinusitis, α1-antitrypsin deficiency, coughs, pulmonary emphysema, pulmonary fibrosis or hyper-reactive airways, chronic obstructive pulmonary disease, and chronic obstructive lung disorder.

"Psoriasis" is a condition characterized by the eruption of circumscribed, discrete and confluent, reddish, silvery-scaled maculopapules. Psoriatic lesions generally occur predominantly on the elbows, knees, scalp, and trunk, and microscopically show characteristic parakerotosis and elongation of rete ridges. The term includes the various forms of psoriasis, including erythrodermic, pustular, moderate-severe and recalcitrant forms of the disease.

"Endometriosis" refers to the ectopic occurrence of endometrial tissue, frequently forming cysts containing altered blood.

The term "vascular disease or disorder" herein refers to the various diseases or disorders which impact the vascular system, including the cardiovascular system. Examples of such diseases include arteriosclerosis, vascular reobstruction, atherosclerosis, postsurgical vascular stenosis, restenosis, vascular occlusion or carotid obstructive disease, coronary artery disease, angina, small vessel disease, hypercholesterolemia, hypertension, and conditions involving abnormal proliferation or function of vascular epithelial cells.

The term "stenosis" refers to narrowing or stricture of a hollow passage (e,g, a duct or canal) in the body.

The term "vascular stenosis" refers to occlusion or narrowing of blood vessels. Vascular stenosis often results from fatty deposit (as in the case of atherosclerosis) or excessive migration and proliferation of vascular smooth muscle cells and endothelial cells. Arteries are particularly susceptible to stenosis. The term "stenosis" as used herein specifically includes initial stenosis and restenosis.

The term "restenosis" refers to recurrence of stenosis after treatment of initial stenosis with apparent success. For example, "restenosis" in the context of vascular stenosis, refers to the reoccurrence of vascular stenosis after it has been treated with apparent success, e.g. by removal of fatty deposit by angioplasty (e.g. percutaneous transluminal coronary angioplasty), direction coronary atherectomy or stent etc. One of the contributing factors in restenosis is intimal hyperplasia. The term "intimal hyperplasia", used interchangeably with "neointimal hyperplasia" and "neointima formation", refers to thickening of the inner most layer of blood vessels, intima, as a consequence of excessive proliferation and migration of vascular smooth muscle cells and endothelial cells. The various changes taking place during restenosis are often collectively referred to as "vascular wall remodeling."

The terms "balloon angioplasty" and "percutaneous transluminal coronary angioplasty" (PTCA) are often used interchangeably, and refer to a non-surgical catheter-based treatment for removal of plaque from the coronary artery. Stenosis or restenosis often lead to hypertension as a result of increased resistance to blood flow.

The term "hypertension" refers to abnormally high blood pressure, i.e. beyond the upper value of the normal range.

"Polyps" refers to a mass of tissue that bulges or projects outward or upward from the normal surface level, thereby being macroscopically visible as a hemispheroidal, speroidal, or irregular moundlike structure growing from a relatively broad base or a slender stalk. Examples include colon, rectal and nasal polyps.

"Fibroadenoma" references a benign neoplasm derived from glandular epithelium, in which there is a conspicuous stroma of proliferating fibroblasts and connective tissue elements. This commonly occurs in breast tissue.

"Asthma" is a condition which results in difficulty in breathing. Bronchial asthma refers to a condition of the lungs in which there is widespread narrowing of airways, which may be due to contraction (spasm) of smooth muscle, edema of the mucosa, or mucus in the lumen of the bronchi and bronchioles.

"Bronchitis" refers to inflammation of the mucous membrane of the bronchial tubes.

For the purposes herein, a "vial" refers to a container which holds a therapeutic agent. The vial may be sealed by a stopper pierceable by a syringe. Generally, the vial is formed from glass material. The therapeutic agent in the vial can be in various states including liquid, lyophilized, frozen etc.

A "package insert" refers to instructions customarily included in commercial packages of therapeutic agents, that contain information about the indications, usage, dosage, administration, contraindications and/or warnings concerning the use of such therapeutic products.

II. Production of Antibodies

A description follows as to exemplary techniques for the production of HER antibodies used in accordance with the present invention. The HER antigen to be used for production of antibodies may be, e.g., a soluble form of the extracellular domain of HER or a portion thereof, containing the desired epitope. Alternatively, cells expressing HER at their cell surface (e.g. NIH-3T3 cells transformed to overexpress HER2; or a carcinoma cell line such as SK-BR-3 cells, see Stancovski et al. *PNAS* (USA) 88:8691-8695 (1991)) can be used to generate antibodies. Other forms of HER receptor useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Various methods for making monoclonal antibodies herein are available in the art. For example, the monoclonal antibodies may be made using the hybridoma method first described by Kohler et al., Nature, 256:495 (1975), by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

WO01/00245 describes production of exemplary humanized HER2 antibodies which bind HER2 and block ligand activation of a HER receptor. The humanized antibody of particular interest herein blocks EGF, TGF-α and/or HRG mediated activation of MAPK essentially as effectively as murine monoclonal antibody 2C4 (or a Fab fragment thereof) and/or binds HER2 essentially as effectively as murine monoclonal antibody 2C4 (or a Fab fragment thereof). The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX, where X is preferrably D or S (SEQ ID NO:7); DVNPNSGGSIYNQRFKG (SEQ ID NO:8); and/or NLGPSFYFDY (SEQ ID NO:9), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy domain amino acid sequence in SEQ ID NO:4.

The humanized antibody may comprise variable light domain complementarity determining residues KASQDVSIGVA (SEQ ID NO:10); SASYX$^1$X$^2$X$^3$, where X$^1$ is preferably R or L, X$^2$ is preferably Y or E, and X$^3$ is preferably T or S (SEQ ID NO:11); and/or QQYYIYPYT (SEQ ID NO:12), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light domain amino acid sequence in SEQ ID NO:3.

The present application also contemplates affinity matured antibodies which bind HER2 and block ligand activation of a HER receptor. The parent antibody may be a human antibody or a humanized antibody, e.g., one comprising the variable light and/or heavy sequences of SEQ ID Nos. 3 and 4, respectively (i.e. variant 574). The affinity matured antibody preferably binds to HER2 receptor with an affinity superior to that of murine 2C4 or variant 574 (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody. The preferred intact IgG1 antibody comprises the light chain sequence in SEQ ID NO:13 and the heavy chain sequence in SEQ ID NO:14.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M113 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597-(1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments comprising one or more antigen binding regions. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the HER2 protein. Other such antibodies may combine a HER2 binding site with binding site(s) for EGFR, HER3 and/or HER4. Alternatively, a HER2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the HER2-expressing cell. Bispecific antibodies may also be used to localize cytotoxic agents to cells which express HER2. These antibodies possess a HER2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific HER2/FcγRIII antibody and U.S. Pat. No. 5,837,234 discloses a bispecific HER2/FcγRI antibody IDM1 (Osidem). A bispecific HER2/Fcα antibody is shown in WO98/02463. U.S. Pat. No. 5,821,337 teaches a bispecific HER2/CD3 antibody. MDX-210 is a bispecific HER2-FcγRIII Ab.

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |

TABLE 1-continued

| Original Residue | Exemplary Substitutions | Preferred Substitutions |
|---|---|---|
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry*, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gin (O)

(3) acidic: Asp (D), Glu (E)

(4) basic: Lys (K), Arg (R), His(H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human HER2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-

2922 (1992). Homodimeric antibodies with enhanced antitumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably the altered Fc region is a human IgG1 Fc region comprising or consisting of substitutions at one, two or three of these positions.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies with improved binding to the neonatal Fc receptor (FcRn), and increased half-lives, are described in WO00/42072 (Presta, L.). These antibodies comprise a Fc region with one or more substitutions therein which improve binding of the Fc region to FcRn. For example, the Fc region may have substitutions at one or more of positions 238, 256, 265, 272, 286, 303, 305, 307, 311, 312, 317, 340, 356, 360, 362, 376, 378, 380, 382, 413, 424 or 434. The preferred Fc region-comprising antibody variant with improved FcRn binding comprises amino acid substitutions at one, two or three of positions 307, 380 and 434 of the Fc region thereof.

Engineered antibodies with three or more (preferably four) functional antigen binding sites are also contemplated (US Appln No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

(viii) Screening for Antibodies with the Desired Properties

Techniques for generating antibodies have been described above. One may further select antibodies with certain biological characteristics, as desired.

To identify an antibody which blocks ligand activation of a HER receptor, the ability of the antibody to block HER ligand binding to cells expressing the HER receptor (e.g. in conjugation with another HER receptor with which the HER receptor of interest forms a HER hetero-oligomer) may be determined. For example, cells naturally expressing, or transfected to express, HER receptors of the HER hetero-oligomer may be incubated with the antibody and then exposed to labeled HER ligand. The ability of the antibody to block ligand binding to the HER receptor in the HER hetero-oligomer may then be evaluated.

For example, inhibition of HRG binding to MCF7 breast tumor cell lines by HER2 antibodies may be performed using monolayer MCF7 cultures on ice in a 24-well-plate format essentially as described in WO01/00245. HER2 monoclonal antibodies may be added to each well and incubated for 30 minutes. $^{125}$I-labeled $rHRG\beta1_{177-224}$ (25 pm) may then be added, and the incubation may be continued for 4 to 16 hours. Dose response curves may be prepared and an $IC_{50}$ value may be calculated for the antibody of interest. In one embodiment, the antibody which blocks ligand activation of a HER receptor will have an $IC_{50}$ for inhibiting HRG binding to MCF7 cells in this assay of about 50 nM or less, more preferably 10 nM or less. Where the antibody is an antibody fragment such as a Fab fragment, the $IC_{50}$ for inhibiting HRG binding to MCF7 cells in this assay may, for example, be about 100 nM or less, more preferably 50 nM or less.

Alternatively, or additionally, the ability of an antibody to block HER ligand-stimulated tyrosine phosphorylation of a HER receptor present in a HER hetero-oligomer may be assessed. For example, cells endogenously expressing the HER receptors or transfected to expressed them may be incubated with the antibody and then assayed for HER ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining HER receptor activation and blocking of that activity by an antibody.

In one embodiment, one may screen for an antibody which inhibits HRG stimulation of p180 tyrosine phosphorylation in MCF7 cells essentially as described in WO01/00245. For example, the MCF7 cells may be plated in 24-well plates and monoclonal antibodies to HER2 may be added to each well and incubated for 30 minutes at room temperature; then $rHRG\beta1_{177-244}$ may be added to each well to a final concentration of 0.2 nM, and the incubation may be continued for 8 minutes. Media may be aspirated from each well, and reactions may be stopped by the addition of 100 µl of SDS sample buffer (5% SDS, 25 mM DTT, and 25 mM Tris-HCl, pH 6.8). Each sample (25 µl) may be electrophoresed on a 4-12% gradient gel (Novex) and then electrophoretically transferred to polyvinylidene difluoride membrane. Antiphosphotyrosine (at 1 µg/ml) immunoblots may be developed, and the intensity of the predominant reactive band at $M_r \sim 180,000$ may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an $IC_{50}$ for the antibody of interest may be calculated. In one embodiment, the antibody which blocks ligand activation of a HER receptor will have an $IC_{50}$ for inhibiting HRG stimulation of p180 tyrosine phosphorylation in this assay of about 50 nM or less, more preferably 10 nM or less. Where the antibody is an antibody fragment such as a Fab fragment, the $IC_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. *Oncogene* 15:1385-1394 (1997). According to this assay, MDA-MB-175 cells may treated with a HER2 monoclonal antibody (10 µg/mL) for 4 days and stained with crystal violet. Incubation with a HER2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the HER2 antibody of interest may block heregulin dependent association of HER2 with HER3 in both MCF7 and SK-BR-3 cells as determined in a co-immunoprecipitation experiment such as that described in WO01/00245 substantially more effectively than monoclonal antibody 4D5, and preferably substantially more effectively than monoclonal antibody 7F3.

To identify growth inhibitory HER2 antibodies, one may screen for antibodies which inhibit the growth of cancer cells which overexpress HER2. In one embodiment, the growth inhibitory antibody of choice is able to inhibit growth of SK-BR-3 cells in cell culture by about 20-100% and preferably by about 50-100% at an antibody concentration of about 0.5 to 30 µg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 µg/ml of the HER2 antibody is added per dish. After six days, the number of cells, compared to untreated cells are counted using an electronic COULTER™ cell counter. Those antibodies which inhibit growth of the SK-BR-3 cells by about 20-100% or about 50-100% may be selected as growth inhibitory antibodies. See U.S. Pat. No. 5,677,171 for assays for screening for growth inhibitory antibodies, such as 4D5 and 3E8.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 µg/ml of the monoclonal antibody. Following a three day incubation period, monolayers are washed with PBS and detached by trypsinization. Cells are then centrifuged, resuspended in $Ca^+$ binding buffer and aliquoted into tubes as discussed above for the cell death assay. Tubes then receive labeled annexin (e.g. annexin V-FTIC) (1 µg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies. In addition to the annexin binding assay, a DNA staining assay using BT474 cells is available. In order to perform this assay, BT474 cells which have been treated with the antibody of interest as described in the preceding two paragraphs are incubated with 9 µg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay. See WO98/17797 for assays for screening for antibodies which induce apoptosis, such as 7C2 and 7F3.

To screen for antibodies which bind to an epitope on HER2 bound by an antibody of interest, a routine cross-blocking assay such as that described in Antibodies, A Laboratory Manual, Cold Spring Harbor Laboratory, Ed Harlow and David Lane (1988), can be performed to assess whether the antibody cross-blocks binding of an antibody, such as 2C4 or pertuzumab, to HER2. Alternatively, or additionally, epitope mapping can be performed by methods known in the art and/or one can study the antibody-HER2 structure (Franklin et al. *Cancer Cell* 5:317-328 (2004)) to see what domain(s) of HER2 is/are bound by the antibody.

(ix) Pertuzumab Compositions

In one embodiment of a HER2 antibody composition, the composition comprises a mixture of a main species pertuzumab antibody and one or more variants thereof. The preferred embodiment herein of a pertuzumab main species antibody is one comprising the variable light and variable heavy amino acid sequences in SEQ ID Nos. 3 and 4, and most preferably comprising a light chain amino acid sequence selected from SEQ ID No. 13 and 17, and a heavy chain amino acid sequence selected from SEQ ID No. 14 and 18 (including deamidated and/or oxidized variants of those sequences). In one embodiment, the composition comprises a mixture of the main species pertuzumab antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab')2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS–. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation -exchange column, such as a PROPAC WCX-10™ cation exchange column). Aside from the amino -terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non -glycosylated heavy chains, or antibody comprising a sialidated oligosaccharide attached to one or two heavy chains thereof etc.

The composition may be recovered from a genetically engineered cell line, e.g. a Chinese Hamster Ovary (CHO) cell line expressing the HER2 antibody, or may be prepared by peptide synthesis.

(x) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC 1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises an antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^1$, $\alpha_2^1$, $\alpha_3^1$, N-acetyl-$\gamma_1^1$, PSAG and $\theta^1_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated HER2 antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol)propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antibody and cytotoxic agent may be made, e.g. by recombinant techniques or peptide synthesis.

Other immunoconjugates are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The antibodies disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

III. Selecting Patients for Therapy

The patient herein is optionally subjected to a diagnostic test prior to therapy. For example, the diagnostic test may evaluate HER (e.g. HER2 or EGFR) expression (including overexpression), amplification, and/or activation (including phosphorylation or dimerization).

Generally, if a diagnostic test is performed, a sample may be obtained from a patient in need of therapy. Where the subject has cancer, the sample is generally a tumor sample. In the preferred embodiment, the tumor sample is from an ovarian cancer, peritoneal cancer, fallopian tube cancer, metastatic breast cancer (MBC), non-small cell lung cancer (NSCLC), prostate cancer, or colorectal cancer tumor sample.

It is noted however, that various other non-malignant therapeutic indications for HER antibodies are described herein. Where the patient is to be treated for those non-malignant indications, a suitable sample can be obtained from the patient and subjected to a diagnostic assay as described herein.

The biological sample herein may be a fixed sample, e.g. a formalin fixed, paraffin-embedded (FFPE) sample, or a frozen sample.

According to one embodiment of the invention herein, the patient selected for therapy has a tumor displaying HER (and preferably HER2) activation. In one embodiment, the extent of HER (or HER2) activation in cancer cells significantly exceeds the level of activation of that receptor in non-cancerous cells of the same tissue type. Such excessive activation may result from overexpression of the HER receptor and/or greater than normal levels of a HER ligand available for activating the HER receptor in the cancer cells. Such excessive activation may cause and/or be caused by the malignant state of a cancer cell. In some embodiments, the cancer will be subjected to a diagnostic or prognostic assay to determine whether amplification and/or overexpression of a HER receptor is occurring which results in such excessive activation of the HER receptor. Alternatively, or additionally, the cancer may be subjected to a diagnostic or prognostic assay to determine whether amplification and/or overexpression a HER ligand is occurring in the cancer which attributes to excessive activation of the receptor. In a subset of such cancers, excessive activation of the receptor may result from an autocrine stimulatory pathway. Various assays for determining HER activation will be described in more detail below.

(i) HER Dimers

Tumors samples can be assessed for the presence of HER dimers, as indicating HER or HER2 activation. Any method known in the art may be used to detect HER2 dimers, such as EGFR-HER2, HER2-HER3, in tumors. Several preferred methods are described below. These methods detect noncovalent protein-protein interactions or otherwise indicate proximity between proteins of interest.

Immunoaffinity-based methods, such as immunoprecipitation or ELISA, may be used to detect HER dimers. In one embodiment, HER2 antibodies are used to immunoprecipitate complexes comprising HER2 from tumor cells, and the resulting immunoprecipitant is then probed for the presence of EGFR or HER3 by immunoblotting. In another embodiment, EGFR or HER3 antibodies may be used for the immunoprecipitation step and the immunoprecipitant then probed with HER2 antibodies. In a further embodiment, HER ligands specific to EGFR, HER3, EGFR/HER2 complexes or HER2/HER3 complexes may be used to precipitate complexes, which are then probed for the presence of HER2. For example, ligands may be conjugated to avidin and complexes purified on a biotin column.

In other embodiments, such as ELISA or antibody "sandwich"-type assays, antibodies to HER2 are immobilized on a solid support, contacted with tumor cells or tumor cell lysate, washed, and then exposed to antibody against EGFR or HER3. Binding of the latter antibody, which may be detected directly or by a secondary antibody conjugated to a detectable label, indicates the presence of heterodimers. In certain embodiments, EGFR or HER3 antibody is immobilized, and HER2 antibody is used for the detection step. In other embodiments HER ligands may be used in place of, or in combination with HER antibodies.

Chemical or UV cross-linking may also be used to covalently join dimers on the surface of living cells. Hunter et al., *Biochem. J.*, 320:847-53. Examples of chemical cross-linkers include dithiobis(succinimidyl) propionate (DSP) and 3,3dithiobis(sulphosuccinimidyl)propionate (DTSSP). In one embodiment, cell extracts from chemically cross-linked tumor cells are analyzed by SDS-PAGE and immunoblotted with antibodies to EGFR and/or HER3. A supershifted band of the appropriate molecular weight most likely represents EGFR-HER2 or HER2-HER3 dimers, as HER2 is the preferred dimerization partner for EGFR and HER3. This result may be confirmed by subsequent immunoblotting with HER2 antibodies.

Fluorescence resonance energy transfer (FRET) may also be used to detect EGFR-HER2 or HER2-HER3 dimers. FRET detects protein conformational changes and protein-protein interactions in vivo and in vitro based on the transfer of energy from a donor fluorophore to an acceptor fluorophore. Selvin, *Nat. Struct. Biol.* 7:730-34 (2000). Energy transfer takes place only if the donor fluorophore is in sufficient proximity to the acceptor fluorophore. In a typical FRET experiment, two proteins or two sites on a single protein are labeled with different fluorescent probes. One of the probes, the donor probe, is excited to a higher energy state by incident light of a specified wavelength. The donor probe then transmits its energy to the second probe, the acceptor probe, resulting in a reduction in the donor's fluorescence intensity and an increase in the acceptor's fluorescence emission. To measure the extent of energy transfer, the donor's intensity in a sample labeled with donor and acceptor probes is compared with its intensity in a sample labeled with donor probe only. Optionally, acceptor intensity is compared in donor/acceptor and acceptor only samples. Suitable probes are known in the art and include, for example, membrane permeant dyes, such as fluorescein and rhodamine, organic dyes, such as the cyanine dyes, and lanthanide atoms. Selvin, supra. Methods and instrumentation for detecting and measuring energy transfer are also known in the art. Selvin, supra.

FRET-based techniques suitable for detecting and measuring protein-protein interactions in individual cells are also known in the art. For example, donor photobleaching fluorescence resonance energy transfer (pbFRET) microscopy and fluorescence lifetime imaging microscopy (FLIM) may be used to detect the dimerization of cell surface receptors. Selvin, supra; Gadella & Jovin, *J. Cell Biol.*, 129:1543-58 (1995). In one embodiment, pbFRET is used on cells either "in suspension" or "in situ" to detect and measure the formation of EGFR-HER2 or HER2-HER3 dimers, as described in Nagy et al., *Cytometry*, 32:120-131 (1998). These techniques measure the reduction in a donor's fluorescence lifetime due to energy transfer. In a particular embodiment, a flow cytometric Foerster-type FRET technique (FCET) may be used to investigate EGFR-HER2 and HER2-HER3 dimerization, as described in Nagy et al., supra, and Brockhoff et al., *Cytometry*, 44:338-48 (2001).

FRET is preferably used in conjunction with standard immunohistochemical labeling techniques. Kenworthy, *Methods*, 24:289-96 (2001). For example, antibodies conjugated to suitable fluorescent dyes can be used as probes for labeling two different proteins. If the proteins are within proximity of one another, the fluorescent dyes act as donors and acceptors for FRET. Energy transfer is detected by standard means. Energy transfer may be detected by flow cytometric means or by digital microscopy systems, such as confocal microscopy or wide-field fluorescence microscopy coupled to a charge-coupled device (CCD) camera.

In one embodiment of the present invention, HER2 antibodies and either EGFR or HER3 antibodies are directly labeled with two different fluorophores, for example as described in Nagy et al, supra. Tumor cells or tumor cell lysates are contacted with the differentially labeled antibodies, which act as donors and acceptors for FRET in the presence of EGFR-HER2 or HER2-HER3 dimers. Alternatively, unlabeled antibodies against HER2 and either EGFR or HER3 are used along with differentially labeled secondary antibodies that serve as donors and acceptors. See, for example, Brockhoff et al., supra. Energy transfer is detected and the presence of dimers is determined if the labels are found to be in close proximity.

In other embodiments HER receptor ligands that are specific for HER2 and either HER1 or HER3 are fluorescently labeled and used for FRET studies.

In still other embodiments of the present invention, the presence of dimers on the surface of tumor cells is demonstrated by co-localization of HER2 with either EGFR or HER3 using standard direct or indirect immunofluorescence techniques and confocal laser scanning microscopy. Alternatively, laser scanning imaging (LSI) is used to detect antibody binding and co-localization of HER2 with either EGFR or HER3 in a high-throughput format, such as a microwell plate, as described in Zuck et al, *Proc. Natl. Acad. Sci. USA*, 96:11122-27 (1999).

In further embodiments, the presence of EGFR-HER2 and/or HER2-HER3 dimers is determined by identifying enzymatic activity that is dependent upon the proximity of the dimer components. A HER2 antibody is conjugated with one enzyme and an EGFR or HER3 antibody is conjugated with a second enzyme. A first substrate for the first enzyme is added and the reaction produces a second substrate for the second enzyme. This leads to a reaction with another molecule to produce a detectable compound, such as a dye. The presence of another chemical breaks down the second substrate, so that reaction with the second enzyme is prevented unless the first and second enzymes, and thus the two antibodies, are in close proximity. In a particular embodiment tumor cells or cell lysates are contacted with a HER2 antibody that is conjugated with glucose oxidase and a HER3 or HER1 antibody that is conjugated with horse radish peroxidase. Glucose is added to the reaction, along with a dye precursor, such as DAB, and catalase. The presence of dimers is determined by the development of color upon staining for DAB.

Dimers may also be detected using methods based on the eTag™ assay system (Aclara Bio Sciences, Mountain View, Calif.), as described, for example, in U.S. Patent Application 2001/0049105, published Dec. 6, 2001, both of which are expressly incorporated by reference in their entirety. An eTag™, or "electrophoretic tag," comprises a detectable reporter moiety, such as a fluorescent group. It may also comprise a "mobility modifier," which consists essentially of a moiety having a unique electrophoretic mobility. These moieties allow for separation and detection of the eTag™ from a complex mixture under defined electrophoretic conditions, such as capillary electrophoresis (CE). The portion of the eTag™ containing the reporter moiety and, optionally, the mobility modifier is linked to a first target binding moiety by a cleavable linking group to produce a first binding compound. The first target binding moiety specifically recognizes a particular first target, such as a nucleic acid or protein. The first target binding moiety is not limited in any way, and may be for example, a polynucleotide or a polypeptide. Preferably, the first target binding moiety is an antibody or antibody fragment. Alternatively, the first target binding moiety may be a HER receptor ligand or binding-competent fragment thereof.

The linking group preferably comprises a cleavable moiety, such as an enzyme substrate, or any chemical bond that may be cleaved under defined conditions. When the first target binding moiety binds to its target, the cleaving agent is introduced and/or activated, and the linking group is cleaved, thus releasing the portion of the eTag™ containing the reporter moiety and mobility modifier. Thus, the presence of a "free" eTag™ indicates the binding of the target binding moiety to its target.

Preferably, a second binding compound comprises the cleaving agent and a second target binding moiety that specifically recognizes a second target. The second target binding moiety is also not limited in any way and may be, for example, an antibody or antibody fragment or a HER receptor ligand or binding competent ligand fragment. The cleaving agent is such that it will only cleave the linking group in the first binding compound if the first binding compound and the second binding compound are in close proximity.

In an embodiment of the present invention, a first binding compound comprises an eTag™ in which an antibody to HER2 serves as the first target binding moiety. A second binding compound comprises an antibody to EGFR or HER3 joined to a cleaving agent capable of cleaving the linking group of the eTag™. Preferably the cleaving agent must be activated in order to be able to cleave the linking group. Tumor cells or tumor cell lysates are contacted with the eTag™, which binds to HER2, and with the modified EGFR or HER3 antibody, which binds to EGFR or HER3 on the cell surface. Unbound binding compound is preferable removed, and the cleaving agent is activated, if necessary. If EGFR-HER2 or HER2-HER3 dimers are present, the cleaving agent will cleave the linking group and release the eTag™ due to the proximity of the cleaving agent to the linking group. Free eTag™ may then be detected by any method known in the art, such as capillary electrophoresis.

In one embodiment, the cleaving agent is an activatable chemical species that acts on the linking group. For example, the cleaving agent may be activated by exposing the sample to light.

In another embodiment, the eTag™ is constructed using an antibody to EGFR or HER3 as the first target binding moiety, and the second binding compound is constructed from an antibody to HER2.

In yet another embodiment, the HER dimer is detected using an antibody or other reagent which specifically or preferentially binds to the dimer as compared to binding thereof to either HER receptor in the dimer.

(ii) HER2 Phosphorylation

Immunoprecipitation with EGFR, HER2, or HER3 antibody as discussed in the previous section may optionally be followed by a functional assay for dimers, as an alternative or supplement to immunoblotting. In one embodiment, immunoprecipitation with HER3 antibody is followed by an assay for receptor tyrosine kinase activity in the immunoprecipitant. Because HER3 does not have intrinsic tyrosine kinase activity, the presence of tyrosine kinase activity in the immunoprecipitant indicates that HER3 is most likely associated with HER2. Graus-Porta et al., *EMBO J.*, 16:1647-55 (1997); Klapper et al., *Proc. Natl. Acad. Sci. USA*, 96:4995-5000 (1999). This result may be confirmed by immunoblotting with HER2 antibodies. In another embodiment, immunoprecipitation with HER2 antibody is followed by an assay for EGFR receptor tyrosine kinase activity. In this assay, the immunoprecipitant is contacted with radioactive ATP and a peptide substrate that mimics the in vivo site of transphosphorylation of HER2 by EGFR. Phosphorylation of the peptide indicates co-immunoprecipitation and thus dimerization of EGFR with HER2. Receptor tyrosine kinase activity assays are well known in the art and include assays that detect phosphorylation of target substrates, for example, by phosphotyrosine antibody, and activation of cognate signal transduction pathways, such as the MAPK pathway.

Phosphorylation of HER receptor may be assessed by immunoprecipitation of one or more HER receptors, such as HER2 receptor, and Western blot analysis. For example, positivity is determined by the presence of a phospho-HER2 band on the gel, using an anti-phosphotyrosine antibody to detect phosphorylated tyrosine residue(s) in the immunoprecipitated HER receptor(s). Anti-phosphotyrosine antibodies are commercially available from PanVera (Madison, Wis.), a subsidiary of Invitrogen, Chemicon International Inc. (Temecula, Calif.), or Upstate Biotechnology (Lake Placid, N.Y.). Negativity is determined by the absence of the band.

In another embodiment, phosphorylation of HER2 (HER2) receptor is assessed by immunohistochemistry using a phospho-specific HER2 antibody (clone PN2A; Thor et al., *J. Clin. Oncol,* 18(18):3230-3239 (2000)).

Other methods for detecting phosphorylation of HER receptor(s) include, but are not limited to, KIRA ELISA (U.S. Pat. Nos. 5,766,863; 5,891,650; 5,914,237; 6,025,145; and 6,287,784), mass spectrometry (comparing size of phosphorylated and non-phosphorylated HER2), and e-tag proximity assay with both a HER (e.g. HER2) antibody and phospho-specific or phospho-tyrosine specific antibody (e.g., using the eTag™ assay kit available from Aclara BioSciences (Mountain View, Calif.). Details of the eTag assay are described hereinabove.

One may also use phospho-specific antibodies in cellular array to detect phosphorylation status in a cellular sample of signal transduction protein (US2003/0190689).

(iii) Gene Expression Profile

In one embodiment, a gene expression analyses can serve as a surrogate for measuring HER phosphorylation or activation directly. This is particularly useful where the sample is a fixed sample (e.g. parrafin-embedded, formalin fixed tumor sample) where HER phosphorylation may be difficult to reliably quantify. According to this method, expression of two or more HER receptors and one or more HER ligand in a sample is evaluated, wherein expression of the two or more HER receptors and one or more HER ligand indicates positive HER phosphorylation or activation in the sample. In one embodiment of this method, expression of betacellulin and/or amphiregulin in the sample can be measured, wherein betacellulin and/or amphiregulin expression indicates positive HER phosphorylation or activation in the sample.

According to this method, a sample from the patient is tested for expression of two or more HER receptors (preferably selected from EGFR, HER2, and HER3) and one or more HER ligands (preferably selected from betacellulin, amphiregulin, epiregulin, and TGF-α, most preferably betacellulin or amphiregulin). For example, the two or more HER receptors may be EGFR and HER2, or HER2 and HER3. Preferably, expression of HER2 and EGFR or HER3, as well as betacellulin or amphiregulin is determined. The sample may be tested for expression of betacellulin or amphiregulin alone, or in combination with testing for expression of two or more HER receptors. Positive expression of the identified gene(s) indicates the patient is a candidate for therapy with a HER antibody, such as pertuzumab. Moreover, positive expression of the gene(s) indicates the patient is more likely to respond favorably to therapy with the HER antibody than a patient who does not have such positive expression.

Various methods for determining expression of mRNA or protein include, but are not limited to, gene expression profiling, polymerase chain reaction (PCR) including quantitative real time PCR (qRT-PCR), microarray analysis, serial analysis of gene expression (SAGE), MassARRAY, Gene Expression Analysis by Massively Parallel Signature Sequencing (MPSS), proteomics, immunohistochemistry (IHC), etc. Preferably mRNA is quantified. Such mRNA analysis is preferably performed using the technique of polymerase chain reaction (PCR), or by microarray analysis. Where PCR is employed, a preferred form of PCR is quantitative real time PCR (qRT-PCR). In one embodiment, expression of one or more of the above noted genes is deemed positive expression if it is at the median or above, e.g. compared to other samples of the same tumor-type. The median expression level can be determined essentially contemporaneously with measuring gene expression, or may have been determined previously.

Various exemplary methods for determining gene expression The steps of a representative protocol for profiling gene expression using fixed, paraffin-embedded tissues as the RNA source, including mRNA isolation, purification, primer extension and amplification are given in various published journal articles (for example: Godfrey et al. *J. Molec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by PCR. Finally, the data are analyzed to identify the best treatment option(s) available to the patient on the basis of the characteristic gene expression pattern identified in the tumor sample examined.

(iv) HER Expression and Amplification

To determine HER expression or amplification in the cancer, various diagnostic/prognostic assays are available. In one embodiment, HER overexpression may be analyzed by IHC, e.g. using the HERCEPTEST® (Dako). Parrafin embedded tissue sections from a tumor biopsy may be subjected to the IHC assay and accorded a HER2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as not overexpressing HER2, whereas those tumors with 2+ or 3+ scores may be characterized as overexpressing HER2.

Tumors overexpressing HER2 may be rated by immunohistochemical scores corresponding to the number of copies of HER2 molecules expressed per cell, and can been determined biochemically:

0=0-10,000 copies/cell,

1+=at least about 200,000 copies/cell,

2+=at least about 500,000 copies/cell,

3+=at least about 2,000,000 copies/cell.

Overexpression of HER2 at the 3+level, which leads to ligand-independent activation of the tyrosine kinase (Hudziak et al., *Proc. Natl. Acad. Sci. USA,* 84:7159-7163 (1987)), occurs in approximately 30% of breast cancers, and in these patients, relapse-free survival and overall survival are diminished (Slamon et al., *Science,* 244:707-712 (1989); Slamon et al., *Science,* 235:177-182 (1987)).

Alternatively, or additionally, FISH assays such as the INFORM™ (sold by Ventana, Ariz.) or PATHVISION™ (Vysis, Ill.) may be carried out on formalin-fixed, paraffin-embedded tumor tissue to determine the extent (if any) of HER2 amplification in the tumor.

In one embodiment, the cancer will be one which expresses (and may overexpress) EGFR, such expression may be evaluated as for the methods for evaluating HER2 expression as noted above.

HER receptor or HER ligand overexpression or amplification may also be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

IV. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized antibody formulations are described in WO 97/04801, expressly incorporated herein by reference.

The preferred pertuzumab formulation for therapeutic use comprises 30 mg/mL pertuzumab in 20 mM histidine acetate, 120 mM sucrose, 0.02% polysorbate 20, at pH 6.0. An alternate pertuzumab formulation comprises 25 mg/mL pertuzumab, 10 mM histidine-HCl buffer, 240 mM sucrose, 0.02% polysorbate 20, pH 6.0.

The formulation herein may also contain more than one active compound as necessary for the particular indication being treated, preferably those with complementary activities that do not adversely affect each other. Various drugs which can be combined with the HER antibody are described in the method of treatment section below. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Treatment and Dosing of HER Antibodies

Examples of various cancers that can be treated with a fixed dose of a HER antibody are listed in the definition section above. Preferred cancer indications include ovarian cancer; peritoneal cancer; fallopian tube cancer; breast cancer, including metastatic breast cancer (MBC); lung cancer, including non-small cell lung cancer (NSCLC); prostate cancer; colorectal cancer; and/or cancer which displays HER expression, amplification and/or activation. In one embodiment, the cancer which is treated is chemotherapy-resistant cancer or platinum-resistant cancer. Administration of fixed dose(s) of the antibody will result in an improvement in the signs or symptoms of cancer.

Aside from cancer, fixed dose(s) of the HER antibodies as disclosed herein may be used to treat various non-malignant diseases or disorders. Such non-malignant diseases or disorders include autoimmune disease (e.g. psoriasis; see definition above); endometriosis; scleroderma; restenosis; polyps such as colon polyps, nasal polyps or gastrointestinal polyps; fibroadenoma; respiratory disease (see definition above); cholecystitis; neurofibromatosis; polycystic kidney disease; inflammatory diseases; skin disorders including psoriasis and dermatitis; vascular disease (see definition above); conditions involving abnormal proliferation of vascular epithelial cells; gastrointestinal ulcers; Menetrier's disease, secreting adenomas or protein loss syndrome; renal disorders; angiogenic disorders; ocular disease such as age related macular degeneration, presumed ocular histoplasmosis syndrome, retinal neovascularization from proliferative diabetic retinopathy, retinal vascularization, diabetic retinopathy, or age related macular degeneration; bone associated pathologies such as osteoarthritis, rickets and osteoporosis; damage following a cerebral ischemic event; fibrotic or edemia diseases such as hepatic cirrhosis, lung fibrosis, carcoidosis, throiditis, hyperviscosity syndrome systemic, Osler Weber-Rendu disease, chronic occlusive pulmonary disease, or edema following burns, trauma, radiation, stroke, hypoxia or ischemia; hypersensitivity reaction of the skin; diabetic retinopathy and diabetic nephropathy; Guillain-Barre syndrome; graft versus host disease or transplant rejection; Paget's disease; bone or joint inflammation; photoaging (e.g. caused by UV radiation of human skin); benign prostatic hypertrophy; certain microbial infections including microbial pathogens selected from adenovirus, hantaviruses, *Borrelia burgdorferi*, *Yersinia* spp. and *Bordetella pertussis*; thrombus caused by platelet aggregation; reproductive conditions such as endometriosis, ovarian hyperstimulation syndrome, preeclampsia, dysfunctional uterine bleeding, or menometrorrhagia; synovitis; atheroma; acute and chronic nephropathies (including proliferative glomerulonephritis and diabetes-induced renal disease); eczema; hypertrophic scar formation; endotoxic shock and fungal infection; familial adenomatosis polyposis; neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); myelodysplastic syndromes; aplastic anemia; ischemic injury; fibrosis of the lung, kidney or liver; T-cell mediated hypersensitivity disease; infantile hypertrophic pyloric stenosis; urinary obstructive syndrome; psoriatic arthritis; and Hasimoto's thyroiditis. Preferred non-malignant indications for therapy herein include psoriasis, endometriosis, scleroderma, vascular disease (e.g. restenosis, artherosclerosis, coronary artery disease, or hypertension), colon polyps, fibroadenoma or respiratory disease (e.g. asthma, chronic bronchitis, bronchieactasis or cystic fibrosis).

The HER antibody is administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

For the prevention or treatment of disease, the fixed dose of HER antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The fixed dose is suitably administered to the patient at one time or over a series of treatments. Preferably, the fixed dose is in the range from about 20 mg to about 2000 mg of the HER antibody. For example, the fixed dose may be approximately 420 mg, approximately 525 mg, approximately 840 mg, or approximately 1050 mg of the HER antibody.

Where a series of fixed doses are administered, these may, for example, be administered approximately every week, approximately every 2 weeks, approximately every 3 weeks, or approximately every 4 weeks, but preferably approximately every 3 weeks. The fixed doses may, for example, continue to be administered until disease progression, adverse event, or other time as determined by the physician. For example, from about two, three, or four, up to about 17 or more fixed doses may be administered.

In one embodiment, one or more loading dose(s) of the antibody are administered, followed by one or more maintenance dose(s) of the antibody. In another embodiment, a plurality of the same fixed dose are administered to the patient.

According to one preferred embodiment of the invention, a fixed dose of HER antibody (e.g. pertuzumab) of approximately 840 mg (loading dose) is administered, followed by one or more doses of approximately 420 mg (maintenance dose(s)) of the antibody. The maintenance doses are preferably administered about every 3 weeks, for a total of at least two doses, up to 17 or more doses.

According to another preferred embodiment of the invention, one or more fixed dose(s) of approximately 1050 mg of the HER antibody (e.g. pertzumab) are administered, for example every 3 weeks. According to this embodiment, one, two or more of the fixed doses are administered, e.g. for up to one year (17 cycles), and longer as desired.

In another embodiment, a fixed dose of approximately 1050 mg of HER2 antibody (e.g. pertuzumab) is administered as a loading dose, followed by one or more maintenance dose(s) of approximately 525 mg of the antibody. About one, two or more maintenance doses may be administered to the patient every 3 weeks according to this embodiment.

Thus, the invention provides a method of treating cancer in a human patient comprising administering at least one fixed dose of pertuzumab to the patient, wherein the fixed dose is approximately 420 mg, approximately 525 mg, approximately 840 mg, or approximately 1050 mg of pertuzumab.

Where the disease is cancer, the patient is preferably treated with a combination of the HER antibody, and one or more chemotherapeutic agent(s). Preferably at least one of the chemotherapeutic agents is an antimetabolite chemotherapeutic agent such as gemcitabine. The combined administration includes coadministration or concurrent administration, using separate formulations or a single pharmaceutical formulation, and consecutive administration in either order, wherein preferably there is a time period while both (or all) active agents simultaneously exert their biological activities. Thus, the antimetabolite chemotherapeutic agent may be administered prior to, or following, administration of the HER antibody. In this embodiment, the timing between at least one administration of the antimetabolite chemotherapeutic agent and at least one administration of the HER antibody is preferably approximately 1 month or less, and most preferably approximately 2 weeks or less. Alternatively, the antimetabolite chemotherapeutic agent and the HER antibody are administered concurrently to the patient, in a single formulation or separate formulations. Treatment with the combination of the chemotherapeutic agent (e.g. antimetabolite chemotherapeutic agent such as gemcitabine) and the HER antibody (e.g. pertuzumab) may result in a synergistic, or greater than additive, therapeutic benefit to the patient.

An antimetabolite chemotherapeutic agent, if administered, is usually administered at dosages known therefor, or optionally lowered due to combined action of the drugs or negative side effects attributable to administration of the antimetabolite chemotherapeutic agent. Preparation and dosing schedules for such chemotherapeutic agents may be used according to manufacturers' instructions or as determined empirically by the skilled practitioner. Where the antimetabolite chemotherapeutic agent is gemcitabine, preferably, it is administered at a dose between about 600 mg/m to 1250 mg/m2 (for example approximately 1000 mg/m 2), for instance, on days 1 and 8 of a 3-week cycle.

Aside from the HER antibody and antimetabolite chemotherapeutic agent, other therapeutic regimens may be combined therewith. For example, a second (third, fourth, etc) chemotherapeutic agent(s) may be administered, wherein the second chemotherapeutic agent is either another, different antimetabolite chemotherapeutic agent, or a chemotherapeutic agent that is not an antimetabolite. For example, the second chemotherapeutic agent may be a taxane (such as paclitaxel or docetaxel), capecitabine, or platinum-based chemotherapeutic agent (such as carboplatin, cisplatin, or oxaliplatin), anthracycline (such as doxorubicin, including, liposomal doxorubicin), topotecan, pemetrexed, vinca alkaloid (such as vinorelbine), and TLK 286. "Cocktails" of different chemotherapeutic agents may be administered.

Other therapeutic agents that may be combined with the HER antibody include any one or more of: a second, different HER antibody (for example, a growth inhibitory HER2 antibody such as trastuzumab, or a HER2 antibody which induces apoptosis of a HER2-overexpressing cell, such as 7C2, 7F3 or humanized variants thereof); an antibody directed against a different tumor associated antigen, such as EGFR, HER3, HER4; anti-hormonal compound, e.g., an anti-estrogen compound such as tamoxifen, or an aromatase inhibitor; a cardioprotectant (to prevent or reduce any myocardial dysfunction associated with the therapy); a cytokine; an EGFR-targeted drug (such as TARCEVAO®, IRESSA® or Cetuximab); an anti-angiogenic agent (especially Bevacizumab sold by Genentech under the trademark AVASTIN™); a tyrosine kinase inhibitor; a COX inhibitor (for instance a COX-1 or COX-2 inhibitor); non-steroidal anti-inflammatory drug, Celecoxib (CELEBREX®); farnesyl transferase inhibitor (for example, Tipifarnib/ZARNESTRA® R115777 available from Johnson and Johnson or Lonafarnib SCH66336 available from Schering-Plough); antibody that binds oncofetal protein CA 125 such as Oregovomab (MoAb B43.13); HER2 vaccine (such as HER2 AutoVac vaccine from Pharmexia, or APC8024 protein vaccine from Dendreon, or HER2 peptide vaccine from GSK/Corixa); another HER targeting therapy (e.g. trastuzumab, cetuximab, gefitinib, erlotinib, C11033, GW2016 etc); Raf and/or ras inhibitor (see, for example, WO 2003/86467); doxorubicin HCl liposome injection (DOXIL®); topoisomerase I inhibitor such as topotecan; taxane; HER2 and EGFR dual tyrosine kinase inhibitor such as lapatinib/GW572016; TLK286 (TELCYTA®); EMD-7200; a medicament that treats nausea such as a serotonin antagonist, steroid, or benzodiazepine; a medicament that prevents or treats skin rash or standard acne therapies, including topical or oral antibiotic; a body temperature-reducing medicament such as acetaminophen, diphenhydramine, or meperidine; hematopoietic growth factor, etc.

Suitable dosages for any of the above coadministered agents are those presently used and may be lowered due to the combined action (synergy) of the agent and HER antibody.

In addition to the above therapeutic regimes, the patient may be subjected to surgical removal of cancer cells and/or radiation therapy.

Preferably, the antibody administered is a naked antibody. However, the antibody administered may be conjugated with a cytotoxic agent. Preferably, the immunoconjugate and/or antigen to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

Aside from administration of the antibody protein to the patient, the present application contemplates administration of an antibody or protein inhibitor by gene therapy. See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

VI. Articles of Manufacture

In another embodiment of the invention, an article of manufacture containing materials useful for the treatment of cancer or the other disorders described above is provided. The article of manufacture comprises a vial with a fixed dose of the HER antibody contained therein and, optionally, a package insert. The vial may be formed from a variety of materials such as glass or plastic, and may be sealed by a stopper pierceable by a syringe. For example, the vial may be a formal vitrum type I glass vial (e.g. 20 cc vial for a 420 mg fixed dose or 50 cc vial for a 1050 mg fixed dose), with DAIKYO GREY™ fluro-resin laminated stopper, and 20 mm flip top aluminum cap. The article of manufacture may further include other materials desirable from a commercial and user standpoint, including other buffers, diluents, filters, needles, and syringes, etc.

In the preferred embodiment, the article of manufacture comprises a vial containing a fixed dose of a HER antibody (e.g. pertuzumab), wherein the fixed dose is approximately 420 mg, approximately 525 mg, approximately 840 mg, or approximately 1050 mg of the HER antibody.

The article of manufacture preferably further comprises a package insert. The package insert may provide instructions to administer the fixed dose to a cancer patient, including but not limited to a patient with ovarian cancer, peritoneal cancer, fallopian tube cancer, metastatic breast cancer (MBC), non-small cell lung cancer (NSCLC), prostate cancer, colorectal cancer, and/or to administer the fixed dose to a cancer patient whose cancer displays HER expression, amplification and/or phosphorylation.

In one embodiment, the article of manufacture comprises two vials, wherein a first vial contains a fixed dose of approximately 840 mg of pertuzumab, and a second vial contains a fixed dose of approximately 420 mg of pertuzumab.

In another embodiment, the article of manufacture of comprises two vials, wherein a first vial contains a fixed dose of approximately 1050 mg of pertuzumab, and a second vial contains a fixed dose of approximately 525 mg of pertuzumab.

VII. Deposit of Materials

The following hybridoma cell lines have been deposited with the American Type Culture Collection, 10801 University Boulevard, Manassas, Va. 20110-2209, USA (ATCC):

| Antibody Designation | ATCC No. | Deposit Date |
|---|---|---|
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

Further details of the invention are illustrated by the following non-limiting Examples. The disclosures of all citations in the specification are expressly incorporated herein by reference.

EXAMPLE 1

The present example evaluates the population pharmacokinetic (PK) and predictive covariates for the HER antibody pertuzumab, and examined the variability of steady-state trough serum concentrations after fixed, body weight-based, or BSA-based dosing methods. Pertuzumab was administered by IV infusion (q3 week) either as a weight-based dose (0.5-15 mg/kg) or a fixed dose (420 mg or 1050 mg). Pertuzumab serum concentration data from one phase Ia and two phase II trials (ovarian and breast), comprising 153 patients and 1458 concentration-time points, were pooled for this analysis using NONMEM™ with the first-order conditional estimation with Interaction (FOCE interaction) method. A linear 2-compartment model best described the data. Body weight, serum albumin, and serum alkaline phosphatase were significant covariates affecting clearance (CL), and body-surface area (BSA) was a significant variable affecting distribution volume at central compartment (Vc). In the final model, CL and Vc were 0.214 L/day and 2.74 L, respectively. Weight only explained 8.3% of inter-patient variability for CL. Evaluation of the final population PK model using a posterior predictive check showed good performance. Compared to fixed dosing, weight- and BSA-based dosing only reduced the population variability of steady-state trough concentrations by 6.2% and 5.8%, respectively, in 1000 simulated subjects bootstrapped from the original data set using the final model. Simulations also showed that the percentages of subjects with predicted steady-state trough concentrations below a target of 20 mcg/mL were similar following fixed, weight- or BSA-based dosing. It was concluded that although humanized antibodies are typically dosed by weight, the analyses in this example demonstrate the desirability of administering the HER antibody, pertuzumab, using a fixed dose to treat cancer.

Methods

Studies and Patients

All three studies used in this analysis were approved by the appropriate ethics committees of the participating centers. Written informed consent was obtained from all patients.

Study 1 was a Phase Ia, open-label, multicenter, dose-escalation study to evaluate the safety, tolerability, and pharmacokinetic profiles of pertuzumab administered intravenously as a single agent to subjects with advanced solid malignancies. These patients received a dose of pertuzumab administered by the IV route every 3 weeks as a 90-minute IV infusion on the $1^{st}$ cycle, then as 30-minute infusion in subsequent cycles. Doses were escalated (0.5, 2, 5, 10, and 15 mg/kg) in cohorts of 3 or 6 subjects until the maximum tolerated dose (MTD) was defined or the highest dose level was reached. During the first cycle of treatment, serum samples for determination of pertuzumab concentrations were collected at serial time points: prior to the dose, at the end of the IV infusion, at 1.5, 4, and 9 hours, and on days 2, 5, 8, and 15. During the second treatment cycle, serum samples for determination of pertuzumab concentrations were collected prior to the dose, 29 minutes following the start of the IV infusion, and on day 8.

Study 2 was a phase II, open-label, single-arm, multicenter trial to evaluate the overall efficacy, safety, tolerability and the effect of tumor-based HER2 activation on the efficacy of pertuzumab in patients with advanced ovarian cancer, in which their disease was refractory to or had recurred following prior chemotherapy. These women received IV infusions of pertuzumab administered as a single agent over a 90-minute period during the $1^{st}$ cycle of treatment at a fixed dose of 840 mg, followed by a 420 mg maintenance dose, delivered as a 30-minute infusion every 3 weeks during subsequent treatment cycles. During the first and second treatment cycle, serum samples for determination of pertuzumab concentrations were collected prior to the dose, 15 minutes following the end of the infusion, and at days 8 and 15. Additional serum samples for determination of pertuzumab concentrations were collected prior to the dose and 15 minutes after the end of the IV infusion during subsequent treatment cycles.

Study 3 was a Phase II, open label, single-arm, multicenter randomized study to evaluate the efficacy and safety of two different doses of pertuzumab administered as a single agent in patients with metastatic breast cancer with low expression of HER2. In first dose cohort, patients received pertuzumab as an IV infusion administered over a 90 minute period as a 840 mg loading dose on the $1^{st}$ cycle, followed by a maintenance dose of 420 mg given every 3 weeks as a 30 minute IV infusion during subsequent treatment cycles. In the second dose cohort, the patients received an IV infusion of pertuzumab as a 1050 mg dose over a 90-minute period on the $1^{st}$ cycle, and as a 1050 mg dose as a 30-minute IV infusion every 3 weeks during subsequent treatment cycles. In study 3, serum samples for determination of pertuzumab concentrations were collected prior to the dose, 15 minutes following the end of infusion, and on days 8 and 15 during the first two treatment cycles. Additional serum samples for determination of pertuzumab concentrations were collected prior to the dose and 15 minutes after the end of infusion during subsequent treatment cycles.

Drug Assay

Pertuzumab serum concentrations were determined by a validated receptor-binding, enzyme-linked, immunosorbent assay (ELISA). The assay used p185HER2 extracellular domain to capture pertuzumab from serum samples. Bound pertuzumab was detected with mouse anti-human Fc-horseradish peroxidase (HRP) (Jackson ImmunoResearch Laboratories, Inc.), and tetramethyl benzidine (TMB) (KPL, Inc.) was used as the substrate for color development to quantify serum pertuzumab. The assay has a minimum quantifiable concentration of 0.25 mcg/mL for pertuzumab in human serum.

Population Pharmacokinetic Analysis

Population non-linear mixed-effect modeling was performed using NONMEM™ (Boeckmann and Beal NONMEM™ User Guide. San Francisco: NONMEM™ Project Group, University of California, San Francisco (1994)) software (Version V, Level 1.0) with NM-TRAN and PREDPP and the Compaq Visual Fortran compiler (Version 6.5). Two different basic structural models, a one- and two-compartmental linear PK model with IV infusion, were fit to serum pertuzumab concentration-time data. The first-order conditional estimation (FOCE) method with $\eta$-$\epsilon$ interaction was used throughout the model-building procedure. An exponential error model was used to describe the interindividual variability for the PK parameters:

$$Pi = \hat{P}_i \exp(\eta_{iP}) \qquad (1)$$

A multiplicative covariate regression model was implemented as follows:

$$\hat{P}i = \theta_1 \left(\frac{X_i}{med(X)}\right)^{\theta_X} (1 + \theta_D D) \qquad (2)$$

where $\eta_{ip}$ denotes the proportional difference between the "true" parameters (Pi) of $i^{th}$ individual patients and the typical value ($\hat{P}_i$) in the population, adjusted for values of covariates equal to those of this individual patient. The $\eta_{ip}$ is the random effects with mean zero and variance $\omega^2$. The $\theta_X$ and $\theta_D$ are the regression coefficients to be estimated for continuous (e.g. WT) or dichotomous (e.g. SEX and RACE) covariates, respectively. Continuous variables were centered on their median (med (X)) values, thus allowing $\theta_1$ to represent the clearance estimate for the typical patient with median covariates. Dichotomous covariates were coded 0 or 1 (e.g., SEX=0 for female, SEX=1 for male; RACE=0 for Caucasian, and RACE=1 for others). The residual variability was modeled as proportional-additive error model:

$C_{pij} = \hat{C}_{pij}(1 + \epsilon_{ij,prop}) + \epsilon_{ij,add}$, where $C_{pij}$ and $\hat{C}_{pij}$ are the $j^{th}$ measured and model-predicted concentration, respectively, for $i^{th}$ individual, and $\epsilon_{ij,prop}$ and $\epsilon_{ij,add}$ denote the proportional and additive residual intra-individual random errors distributed with zero means and variances $\sigma_{prop}^2$ and $\sigma_{add}^2$.

The relationships between structural model-based Bayesian estimates of the PK parameters and individual covariates were explored graphically. Based on preliminary exploratory analyses, the effect of each covariate on PK parameters was tested. Initially, the influence of covariates on individual PK parameters (i.e., clearance and volume of the central compartment) was examined. Then, a full covariate model for the individual PK parameters was constructed by incorporating the significant covariates into the model. A backward elimination process was used to determine the final covariate model for each individual PK parameter by retaining only the significant covariates in the model. When highly correlated covariates had a similar pharmacological meaning (such as weight and BSA), only the most significant factor was retained in the model. This final covariate model obtained for each PK parameter was then combined to form a new full model and the final population PK model was elaborated using a backward elimination process.

Comparison of alternative structural models and construction of the covariate model was based on the typical goodness-of-fit diagnostic plots and likelihood ratio test. When comparing alternative hierarchical models, the differences in the value of the objective function is approximately chi-square distributed with n degree of freedom (n is the difference in the number or parameters between the full and the reduced model). This approximation has been shown to be reliable for the FOCE-INTERACTION estimation method (Wahlby et al. *J Pharmacokinet Pharmacodyn* 28:231-52 (2001)). To discriminate two hierarchical models, a difference in an objective function of greater than 7.9 (I degree of freedom), which corresponds to a significance level of p<0.005, was used.

The fraction of inter-individual variance (% variance) explained by the covariates in the regression model for a given PK parameters (e.g., CL) was computed as follows:

$$\% \text{ variance} = \left(\frac{\omega_{CL,BASED}^2 - \omega_{CL,FINAL}^2}{\omega_{CL,BASE}^2}\right) \times 100 \qquad (3)$$

Where $\omega^2_{CL,BASED}$ and $\omega^2_{CL,FINAL}$ represented inter-individual variance of clearance in based and final PK model, respectively.

Population Pharmacokinetic Model Evaluation

The model evaluation in this study utilized a bootstrap resampling technique to evaluate the stability of the final model and estimate the confidence interval of parameters. This model evaluation technique consists of first creating data sets using the bootstrap option in the software package Wings for NONMEM™ (N Holford, Version 404, June 2003, Auckland, New Zealand) then obtaining parameter estimates for each of the replicate data sets. The results from 1000 successful runs were obtained, and the mean and $2.5^{th}$ and $97.5^{th}$ percentiles (denoting the 95% confidence interval) for the population parameters were determined and compared with the estimates of the original data.

In addition, a posterior predictive model checks were used to evaluate the ability of the final model to describe the observed data (Yano et al. *J Pharmacokinet Pharmacodyn* 28:171-92 (2001); Gelman and Meng, Model checking and model improvement. In: Gilks W R, Richardson S, Spiegelhalter D J, eds. *Markov Chain Monte Carlo in Practice*. Boca Raton: Chapman & HalVCRC, 189-202 (1996); Gelman et al. *Bayesian Data Analysis*. Boca Raton: Chapman & Hall/CRC (2004). In these analyses, the $2.5^{th}$, $5^{th}$, $10^{th}$, $25^{th}$, $50^{th}$ (median), $75^{th}$, $90^{th}$, and $95^{th}$ percentiles of the observed data were computed and selected as the test statistics for the posterior predictive model check. The final population PK model, including final fixed and random-effect parameters, was used to simulate 1000 replicates of the observed data set and test statistics were computed from each of those simulated dataset. The posterior predictive distribution of test statistics from the simulated dataset was then compared with the observed test statistics, and the p-value ($p^{PPC}$) can be estimated by calculating the proportion of cases in which test statistics from the simulated data set exceed the realized value of observed test statistics according to the following equation (Gelman and Meng, (1996) supra).

$$p^{PPC} = \frac{1}{N} \sum_{i=1}^{1000} I(T(y_i^{rep}, \theta) \geq T(y, \theta_i)) \qquad (1)$$

Where I(.) is the indicator function which takes the value 1 when its argument is true and 0 otherwise. T(y,$\theta$) is a 'realized value' of the observed test statistics because it is realized by the observed data y. T($y_i^{rep}$, $\theta$) is the test statistics from a simulated data set i (range from 1 to 1000) (Gelman and Meng, (1996) supra).

In addition, the $2.5^{th}$, $5^{th}$, $95^{th}$, and $97.5^{th}$ quantiles of the simulated data were calculated for each time points for individual patients. The numbers of observed data that fell within the boundaries of the $2.5^{th}$ and $95.5^{th}$ quantiles (95% interval), $5^{th}$ and $95^{th}$ quantiles (90% interval) of the pooled simulated data were determined.

Pertuzumab Exposures after Fixed, BSA-, and Weight-Based Dosing

The final population PK model was used to determine the steady state trough concentrations and exposure after fixed, BSA-, and weight-based dosing. Serum concentration-time profiles and clearance of pertuzumab for 1000 subjects were simulated for a fixed, BSA-based, or weight-based dosing regimen using the final model with a dataset obtained by bootstrapping (with replacement) the original PK dataset. All simulated subjects received a 840 mg, 12.2 mg/kg, or 485 mg/m2 iv infusion over 90 min on Day 0, then a 420 mg, 6.1 mg/kg, or 242.5 mg/m iv infusion over 30 min on Days 21, 42 and 63. Steady state trough concentrations obtained on Day 84 ($Css_{trough}$) after different dosing regimens were then assessed. In addition, the percent of subjects with steady state trough concentrations below a target concentration (20 mcg/ml) after a fixed, BSA-based or weight-based dose were calculated. Simulated clearance values were used to determine the steady state average exposure ($AUCss_{0-\tau}$) according to the following equation:

$$AUC_{SS0-\tau} = \frac{Dose}{CL} \quad (4)$$

Demographic data. The demographic characteristics of the patients included in this PK analysis are listed in Table 2.

TABLE 2

Demographic characteristics of the patients included in the analysis

| | Median | Range |
|---|---|---|
| Age (years) | 56.0 | 32.0-78.0 |
| BSA* (m$^2$) | 1.73 | 1.40-2.53 |
| Weight (kg) | 69.0 | 45.0-150.6 |
| Albumin (g/L) | 39.2 | 21.0-52.0 |
| Alkaline phosphatase (ALK) (IU/L) | 107.0 | 39.0-367.0 |

| | Number of Patients | % |
|---|---|---|
| Gender | | |
| Male | 8 | 5.2 |
| Female | 145 | 94.8 |
| Race | | |
| Caucasian | 141 | 92.2 |
| African American | 3 | 2.0 |
| Hispanic | 4 | 2.6 |
| Asian | 3 | 2.0 |
| Native Indian | 0 | 0 |
| Others | 2 | 1.3 |

*BSA, body surface area.

A total of 1458 pertuzumab serum concentration time points were collected from 153 patients in the three studies. Of the total, 18 patients were from the phase Ia trial, 60 from the phase II ovarian cancer trial, and 75 from the phase II breast cancer trial. Thus, the majority (94.8%) of the patients in this analysis were female and accounted for 1110 (76%) of the serum pertuzumab concentration data. All subjects had low HER2 expression tumor confirmed by FISH (fluorescence in situ hybridization) analysis and had good physical functional status as indicated by an ECOG (Eastern Cooperative Oncology Group) performance status of either 0 or 1. The number of patients with missing covariates was very low (4.6% for both height and BSA) and the missing covariates were imputed with the median values. In 384 (20.8%) serum pertuzumab concentration samples with only a documented sampling date, the sampling time was imputed to occur at 12 noon. A sensitivity analysis conducted to assess the effects of these imputed times on the population parameters estimates in the model revealed no significant influence.

Population PK analysis. A two-compartment model described the data better than one-compartment model based on the change of objective function ($\delta$=−736.2) and diagnostic plots. A representative pertuzumab serum concentration-time profile fit to a one- and two-compartment model are illustrated in FIGS. 9A-B. The inter-individual variability term ($\eta$) of K12 was removed from two-compartmental models since the removal of this $\eta$ term did not result in a statistically significant increase ($\delta$<7.88) in the objective function. Therefore, only $\eta_{CL}$, $\eta_{Vc}$ and $\eta_{k21}$ were retained in the final base model.

The effect of the presence of a covariance term among $\eta_{CL}$, $\eta_{Vc}$ and $\eta_{k21}$ was next assessed. Incorporation of a covariance terms among $\eta_{CL}$, $\eta_{Vc}$ and $\eta_{k21}$ improved the fit ($\delta$=−23.2, df=3). However, the covariance terms were found to be poorly estimated (% CV>100), have a small estimated correlation ($r_{CL-Vc}$=0.37; $r_{CL-K21}$=0.27; $r_{Vc-K21}$=0.42), and have little influence on parameter estimations (data not shown). Therefore, the covariance terms were not retained for covariate effect model building. In an exploratory analysis using the final base model, no apparent relationships between potential covariates and $\eta_{k21}$ were identified. Therefore, covariate effect on $\eta_{k21}$ was not examined during the development of the final model with covariates.

For the final model with covariates, predicted versus observed pertuzumab serum concentrations and weighted residuals versus predicted serum concentration plots are shown in FIGS. 10A-B. In the final model, serum albumin (ALB), body weight (BW) and serum alkaline phosphatase (ALKP) were the most significant covariates explaining inter-individual variability for pertuzumab clearance (CL). BSA was the most significant covariate explaining interindividual variability of pertuzumab central compartment volume of distribution (Vc). Incorporation of covariance terms among $\eta_{CL}$, $\eta_{Vc}$ and $\eta_{k21}$ improved the fit ($\delta$=−14.0,df=3). However, the estimated correlation was not large ($r_{CL-Vc}$=0.45; $r_{CL-K21}$=0.28; $r_{Vc-K21}$=0.39) and the parameter estimates were not influenced (data not shown). Hence, the covariance terms were not included in the final model. The final model was illustrated as follows:

$$CL = \theta_{CL} \times \left(\frac{WT}{69}\right)^{\theta_{WT\_CL}} \times \left(\frac{ALB}{39.2}\right)^{\theta_{ALB\_CL}} \times \left(\frac{ALKP}{107}\right)^{\theta_{ALKP\_CL}} \quad (4)$$

$$Vc = \theta_{Vc} \times \left(\frac{BSA}{1.72}\right)^{\theta_{BSA\_Vc}} \quad (5)$$

The parameter estimates of the final model are summarized in Table 3.

TABLE 3

Parameter Estimates of the Final Population Pharmacokinetic Model and the Stability of the Parameters Using a Bootstrap Validation Procedure

| | Original Data Set Estimate (% RSE)[a] | 1000 bootstrap Replicates Mean (95% CI) |
|---|---|---|
| Structural Model | | |
| CL (L/day) | 0.214 (3.1) | 0.214 (0.201, 0.228) |
| Vc (L) | 2.740 (1.9) | 2.739 (2.640, 2.840) |
| K12 (day$^{-1}$) | 0.203 (16.6) | 0.220 (0.159, 0.416) |
| K21 (day$^{-1}$) | 0.258 (15.6) | 0.275 (0.203, 0.480) |

TABLE 3-continued

Parameter Estimates of the Final Population Pharmacokinetic
Model and the Stability of the Parameters Using
a Bootstrap Validation Procedure

| | Original Data Set Estimate (% RSE)[a] | 1000 bootstrap Replicates Mean (95% CI) |
|---|---|---|
| Inter-individual Variability | | |
| CL % CV | 31.1 (11.0) | 30.6 (27.0, 34.1) |
| Vc % CV | 16.2 (20.3) | 16.0 (12.7, 19.2) |
| $K_{21}$ % CV | 25.2 (37.6) | 24.1 (11.4, 33.6) |
| Covariate Model | | |
| ALB on CL ($\theta_{ALB\_CL}$) | −1.010 (18.4) | −1.019 (−1.420, −0.632) |
| WT on CL ($\theta_{WT\_CL}$) | 0.587 (19.3) | 0.589 (0.372, 0.826) |
| ALKP on CL ($\theta_{ALKP\_Vc}$) | 0.169 (29.5) | 0.170 (0.067, 0.258) |
| BSA on Vc ($\theta_{BSA\_Vc}$) | 1.160 (12.2) | 1.151 (0.890, 1.451) |
| Residual Variability | | |
| Proportional error $\sigma^2_{prop}$ | 0.037 (19.4) | 0.037 (0.030, 0.045) |
| Additive error, $\sigma_{prop}$, mcg/mL | 2.265 (77.8) | 2.24 (0.002, 4.160) |

[a]% RSE: percent relative standard error of the estimate = SE/parameter estimate × 100

The CL of serum pertuzumab in the analysis population was estimated to be 0.214 L/day and the Vc was 2.74 L. The $K_{12}$ and $K_{21}$ were 0.203 and 0.258 days$^{-1}$, respectively. Inter-individual variability for CL and Vc in the final model, calculated as the square root of interindividual variance ($\omega^2$) and expressed as % CV, are 31.1% and 16.2%, respectively, compared to 38.0% and 20.8% for the base model without covariates. The covariate effect of ALB, WT, and ALKP in the final model therefore explained about 33% of the interindividual variance for CL. However, weight alone explained only 8.3% of inter-patient variability for CL. The covariate effect of BSA explained about 39% of interindividual variance for Vc in the final model. The dependency of CL on WT and Vc on BSA with the base model is accounted for in the final model as shown in FIGS. 11A-B. The estimated $t_{1/2\alpha}$ and $t_{1/2\beta}$ were 1.4 and 17.2 days, respectively.

Model Evaluation. From the original dataset, 1000 successful bootstrap runs were obtained and compared to the original observed data. Mean population PK estimates obtained from the bootstrap procedure were similar to the parameter estimates of the original dataset (Table 3), indicating that the developed model was stable. The 95% confidence intervals for the fixed-effect parameters were narrow, which indicated good precision.

A posterior predictive model check was used to evaluate the ability of the final model to describe the observed data. The final population pharmacokinetic model, including final fixed and random -effect parameters, was used to simulate 1000 replicates. The test statistics were then computed for each of those 1000 simulated dataset. FIGS. 12A-F display histograms of the 1000 simulated values of selected test statistics, with the "realized value" of the observed test statistics indicated by vertical line. The posterior predictive distributions were close to the observed values with the estimated p-values greater than 0.05 for each test statistics. In addition, the percents of observed pertuzumab concentrations within 90% and 95% quantile range of the pooled simulated data were 89.3 and 94.7%, respectively. These results suggested that the model was able to describe and predict the data reasonably well.

Pertuzumab Exposures after Fixed, BSA-, and Weight-Based Dosing.

Predicted pertuzumab steady-state trough serum concentrations on day 84 ($C_{ss,trough}$) were estimated for 1000 simulated subjects bootstrapped from the original PK dataset and the final model using a fixed, weight-based, or BSA-based dose according to the dose schedules outlined in the methods section. These data showed that with weight-based and BSA-based dosing, population variability of $C_{ss,trough}$ decreased by 6.17 and 5.76%, respectively, when compared to fixed dosing (FIG. 13 and Table 4).

TABLE 4

Predicted Pertuzumab Steady State Trough Concentration (Day 84)
After a Fixed, Weight or BSA-based Dose for 1000 Simulated
Subjects Bootstrapped from Original PK Dataset
According to the Final Model

| | Css trough (mcg/ml) Fixed Dose | Css trough (mcg/ml) Weight-based Dose | Css trough (mcg/ml) BSA-based Dose |
|---|---|---|---|
| Minimum | 2.68 | 2.39 | 2.54 |
| 5$^{th}$ Percentile | 16.56 | 16.32 | 16.86 |
| Median | 51.87 | 51.81 | 52.48 |
| Mean | 56.37 | 56.08 | 56.44 |
| 95$^{th}$ Percentile | 115.38 | 110.46 | 112.14 |
| Maximum | 209.67 | 179.06 | 192.00 |
| % CV | 54.05 | 52.62 | 52.40 |
| Variance | 928.21 | 870.93 | 874.71 |
| % Variance Changed from Fixed Dose[a] | — | −6.17 | −5.76 |
| Percent of Subjects with $C_{ss,trough} \leq 20$ mcg/ml | 8.3 | 8.7 | 8.3 |

[a]Percent variance changed from fixed dose was calculated using the following equation:

$$\text{Percent variance change} = \frac{\text{Variance WT or BSA-based dose} - \text{Variance fixed dose}}{\text{Variance fixed dose}} \times 100$$

The percentage of subjects with $C_{ss,trough}$ below a target serum concentration of 20 mcg/ml were similar, with values of 8.3%, 8.7%, and 8.3% for fixed, weight-based, or BSA-based dosing, respectively (Table 4). Similar results were obtained from the analysis of pertuzumab serum steady state $AUC_{ss,0-\tau}$ for 1000 simulated subjects, and weight- and BSA-based dosing only reduced the population variability by 2.2 and 4.2%, respectively, when compared to fixed dosing. The same simulated dataset was used to determine $C_{ss,trough}$ after a fixed dose, weight-, and BSA-based dose for populations with extreme weight (i.e., WT≦10$^{th}$ and ≧90$^{th}$ percentile) (FIGS. 14A-B). Median pertuzumab $C_{ss,trough}$ for population with WT less than or equal to 10$^{th}$ percentile were 72.3 (range: 8.7 to 166.5), 52.8 (range: 6.8 to 125.7) and 63.2 (range: 7.8 to 150.1) mcg/ml for a fixed dose, weight-, and BSA-based dose, respectively. The percentage of subjects in population with $C_{ss,trough}$ below a target serum concentration of 20 mcg/ml were 5.4%, 12.6%, and 9.0% for fixed, weight-based, and BSA-based dosing, respectively. Median pertuzumab $C_{ss,trough}$ for population with WT greater than or equal to 90$^{th}$ percentile were 42.1 (range: 7.0 to 119.8), 62.8 (range: 14.4 to 167.3) and 52.9 (range: 10.2 to 133.3) mcg/ml for a fixed dose, weight-, and BSA-based dose, respectively. The percentages of subjects in this population with $C_{ss,trough}$ below a target serum concentration of 20 mcg/ml were similar, with values of 7.4%, 2.8%, and 5.6% for fixed, weight-based, or BSA-based dosing, respectively. Similar results were obtained for the analysis of pertuzumab serum steady state $AUC_{ss_{0-\tau}}$ of these subgroups from 1000 simulated subjects.

DISCUSSION

Typically, humanized IgG monoclonal antibodies and cytotoxic small molecule drugs in oncology have been administered on a weight-based (mg/kg) or BSA-based dose basis. Pertuzumab has undergone testing in the clinic with a phase Ia trial in patients with advanced cancers and in phase II trials in patients with ovarian, breast, lung, and prostate cancer. Pertuzumab was dosed on a weight-basis (mg/kg) in a Phase I trial, and then initiated using a fixed dose in a phase II trials. Using demographic and serum pertuzumab concentration-time data collected in these three trials, a population PK model with predictive covariates for pertuzumab PK was built herein. This model was then used to examine the steady-state concentrations after fixed dosing, weight- and BSA-based dosing methods.

Pertuzumab PK obtained from this analysis was very similar to those reported for other humanized monoclonal IgG1 drugs used in oncology (Harris et al. *Proc Am Soc Clin Oncol* 21:488a (2002); Leyland-Jones et al. *J Clin Oncol* 21:3965-71 (2003); and Lu et al. *Clin Pharmacol Ther* 75:91 (2004)).

A linear 2-compartment linear PK model best describe the data and in the final model pertuzumab CL was 0.214 L/day. Typical Vc of pertuzumab was 2.74 L or approximately 40 ml/kg, which is equal to human plasma volume and was consistent with values reported for other monoclonal IgG1 drugs (Harris et al. (2002), supra; and Lu et al. (2004), supra). Pertuzumab CL was significantly affected by body weight and serum concentrations of albumin and alkaline phosphatase, while Vc was significantly influenced by BSA. The effect of gender on the pertuzumab PK cannot be assessed because of the small number of male subjects (5.2%) included in the analysis. The results from a bootstrap procedure and posterior model checking suggested that the final model was stable and able to describe and predict the data reasonably well.

The effect of weight on CL and BSA on Vc suggested that pertuzumab might be dosed based on either body weight or BSA. However, the covariate effect of weight alone and BSA alone in the model only explained about 8.3% and 40% of the inter-individual effect of CL and Vc, respectively. This suggested that while weight is a predictor of CL and BSA is a predictor for Vc, the effect of weight and BSA on pertuzumab exposures after dosing might be measurable but not highly contributory.

Therefore, the next step assessed the impact of the various dosing methods on the pertuzumab exposures using simulations. In 1000 subjects bootstrapped from the original data set, weight-based or BSA-based dosing were found to decrease population variability of simulated steady state trough serum concentrations on day 84 by only 6.2 and 5.8%, respectively, when compared to fixed dosing. In addition, the percentages of subjects with predicted steady-state trough serum concentrations below a selected target of 20 mcg/mL were similar with all three dosing methods. Similar results were obtained from the subgroup analysis in population with extreme body weight (i.e., $WT \leq 10^{th}$ and $\geq 90^{th}$ percentile).

Hence, it is concluded that pertuzumab PK is related to WT and BSA. However, the WT and BSA explained only a small percent of the inter-individual variability of CL and Vc, and WT- and BSA-based dosing do not seem to improve the predictability of pertuzumab steady state exposures. It is recommended to apply fixed-dosing regimens for pertuzumab in cancer patients.

The present invention is believed to represent the first disclosure of a critical assessment of the impact of weight- or BSA-based dosing of a humanized IgG1 monoclonal antibody on steady state drug concentrations in cancer patients. Implementation of flat-fixed dosing has several significant patient care and economic implications: i) lower costs due to greater efficiency in manufacturing, storing and shipping of single unit dose, ii) efficient preparation of a single dose in pharmacies and hospitals without the need for patient individualization, iii) greater efficiency in physician prescribing of single unit dose, and iv) lower likelihood of patient receiving wrong dose due to dose calculation errors. Although humanized antibodies are typically dosed by weight or BSA, the analyses herein demonstrate the feasibility of administrating the HER antibody pertuzumab using a fixed dose in cancer patients.

What is claimed is:

1. A method for treating HER2 expressing cancer comprising administering one or more fixed dose(s) of HER2 antibody to a human patient in an amount effective to treat the cancer, wherein the fixed dose is selected from the group consisting of approximately 420 mg, approximately 525 mg, approximately 840 mg, and approximately 1050 mg of the HER2 antibody, wherein the HER2 antibody comprises the variable light and variable heavy amino acid sequences in SEQ ID Nos. 3 and 4, respectively.

2. The method of claim 1 wherein the HER2 antibody is pertuzumab.

3. The method of claim 1 wherein the fixed dose is 420 mg of the HER2 antibody.

4. The method of claim 1 wherein the fixed dose is 840 mg of the HER2 antibody.

5. The method of claim 1 wherein the fixed dose is 1050 mg of the HER2 antibody.

6. The method of claim 1 wherein the fixed dose is 525 mg of the HER2 antibody.

7. The method of claim 1 wherein a fixed dose of the HER2 antibody is administered to the patient approximately every week, approximately every 2 weeks, approximately every 3 weeks, or approximately every 4 weeks.

8. The method of claim 7 wherein a fixed dose of the HER2 antibody is administered to the patient approximately every 3 weeks.

9. The method of claim 1 comprising administering a loading dose of approximately 840 mg of the HER2 antibody followed by one or more maintenance doses of approximately 420 mg of the HER2 antibody.

10. The method of claim 9 wherein the maintenance doses are administered approximately every 3 weeks.

11. The method of claim 1 comprising administering a loading dose of approximately 1050 mg of the HER2 antibody followed by one or more maintenance doses of approximately 525 mg of the HER2 antibody.

12. The method of claim 11 wherein the maintenance doses are administered approximately every 3 weeks.

13. The method of claim 1 wherein the HER2 antibody is a naked antibody.

14. The method of claim 1 wherein the HER2 antibody is an intact antibody.

15. The method of claim 1 wherein the HER2 antibody is an antibody fragment comprising an antigen binding region.

16. The method of claim 1 wherein the HER2 antibody is a humanized or human IgG1 antibody.

17. The method of claim 1 wherein the cancer displays HER2 expression, amplification, or activation.

18. The method of claim 1 wherein the cancer is ovarian, peritoneal, or fallopian tube cancer.

19. The method of claim 1 wherein the cancer is metastatic breast cancer (MBC).

20. The method of claim 1 wherein the cancer is non-small cell lung cancer (NSCLC).

21. The method of claim 1 wherein the cancer is prostate cancer.

22. The method of claim 1 wherein the cancer is colorectal cancer.

23. The method of claim 1 comprising administering a second therapeutic agent to the patient.

24. The method of claim 23 wherein the second therapeutic agent is selected from the group consisting of chemotherapeutic agent, different HER2 antibody, antibody directed against a different tumor associated antigen, anti-hormonal compound, cardioprotectant, cytokine, EGFR-targeted drug, anti-angiogenic agent, tyrosine kinase inhibitor, COX inhibitor, non-steroidal anti-inflammatory drug, farnesyl transferase inhibitor, antibody that binds oncofetal protein CA 125, HER2 vaccine, another HER targeting therapy, Raf or ras inhibitor, doxorubicin HCL liposome injection, topotecan, taxane, dual tyrosine kinase inhibitor, TLK286, EMD-7200, a medicament that treats nausea, a medicament that prevents or treats skin rash or standard acne therapy, a body temperature-reducing medicament, and a hematopoietic growth factor.

25. The method of claim 24 wherein the second therapeutic agent is a chemotherapeutic agent.

26. The method of claim 25 wherein the chemotherapeutic agent is an antimetabolite chemotherapeutic agent.

27. The method of claim 26 wherein the antimetabolite chemotherapeutic agent is gemcitabine.

28. The method of claim 23 wherein the second therapeutic agent is trastuzumab, erlotinib HCL, or bevacizumab.

29. A method of treating HER2 expressing cancer in a human patient comprising administering at least one fixed dose of pertuzumab to the patient, wherein the fixed dose is selected from the group consisting of approximately 420 mg, approximately 525 mg, approximately 840 mg, and approximately 1050 mg of pertuzumab.

30. The method of claim 29 wherein a fixed dose of pertuzumab is administered to the patient approximately every 3 weeks.

31. The method of claim 29 wherein the cancer is selected from the group consisting of ovarian cancer, peritoneal cancer, fallopian tube cancer, metastatic breast cancer (MBC), non-small cell lung cancer (NSCLC), prostate cancer, and colorectal cancer.

32. The method of claim 29 wherein the fixed dose is selected from the group consisting of 420 mg, 525 mg, 840 mg, and 1050 mg of pertuzumab.

* * * * *

UNITED STATES PATENT AND TRADEMARK OFFICE
CERTIFICATE OF CORRECTION

| | | |
|---|---|---|
| PATENT NO. | : 7,449,184 B2 | Page 1 of 1 |
| APPLICATION NO. | : 11/154091 | |
| DATED | : November 11, 2008 | |
| INVENTOR(S) | : Allison et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 191 days Delete the phrase "by 191 days" and insert -- by 648 days --

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,449,184 B2 | Page 1 of 1 |
| APPLICATION NO. | : 11/154091 | |
| DATED | : November 11, 2008 | |
| INVENTOR(S) | : Allison et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

This certificate supersedes the Certificate of Correction issued May 11, 2010.

Signed and Sealed this
Fifth Day of May, 2015

Michelle K. Lee
*Director of the United States Patent and Trademark Office*

SEQUENCE LISTING

<160> NUMBER OF SEQ ID NOS: 22

<210> SEQ ID NO 1
<211> LENGTH: 107
<212> TYPE: PRT
<213> ORGANISM: Mus musculus

<400> SEQUENCE: 1

Asp Thr Val Met Thr Gln Ser His Lys Ile Met Ser Thr Ser Val
1               5                   10                  15

Gly Asp Arg Val Ser Ile Thr Cys Lys Ala Ser Gln Asp Val Ser
                20                  25                  30

Ile Gly Val Ala Trp Tyr Gln Gln Arg Pro Gly Gln Ser Pro Lys
                35                  40                  45

Leu Leu Ile Tyr Ser Ala Ser Tyr Arg Tyr Thr Gly Val Pro Asp
                50                  55                  60

```
Arg Phe Thr Gly Ser Gly Ser Gly Thr Asp Phe Thr Phe Thr Ile
            65                  70                  75

Ser Ser Val Gln Ala Glu Asp Leu Ala Val Tyr Tyr Cys Gln Gln
            80                  85                  90

Tyr Tyr Ile Tyr Pro Tyr Thr Phe Gly Gly Gly Thr Lys Leu Glu
            95                 100                 105

Ile Lys

<210> SEQ ID NO 2
<211> LENGTH: 119
<212> TYPE: PRT
<213> ORGANISM: Mus musculus

<400> SEQUENCE: 2

Glu Val Gln Leu Gln Gln Ser Gly Pro Glu Leu Val Lys Pro Gly
 1               5                  10                  15

Thr Ser Val Lys Ile Ser Cys Lys Ala Ser Gly Phe Thr Phe Thr
                20                  25                  30

Asp Tyr Thr Met Asp Trp Val Lys Gln Ser His Gly Lys Ser Leu
            35                  40                  45

Glu Trp Ile Gly Asp Val Asn Pro Asn Ser Gly Gly Ser Ile Tyr
            50                  55                  60

Asn Gln Arg Phe Lys Gly Lys Ala Ser Leu Thr Val Asp Arg Ser
            65                  70                  75

Ser Arg Ile Val Tyr Met Glu Leu Arg Ser Leu Thr Phe Glu Asp
            80                  85                  90

Thr Ala Val Tyr Tyr Cys Ala Arg Asn Leu Gly Pro Ser Phe Tyr
            95                 100                 105

Phe Asp Tyr Trp Gly Gln Gly Thr Thr Leu Thr Val Ser Ser
           110                 115

<210> SEQ ID NO 3
<211> LENGTH: 107
<212> TYPE: PRT
<213> ORGANISM: Artificial Sequence
<220> FEATURE:
<223> OTHER INFORMATION: sequence is synthesized

<400> SEQUENCE: 3

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
                20                  25                  30

Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Tyr Ile Tyr Pro Tyr Thr Phe Gly Gln Gly Thr Lys Val Glu
            95                 100                 105

Ile Lys

<210> SEQ ID NO 4
```

```
<211> LENGTH: 119
<212> TYPE: PRT
<213> ORGANISM: Artificial Sequence
<220> FEATURE:
<223> OTHER INFORMATION: sequence is synthesized

<400> SEQUENCE: 4

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
                20                  25                  30

Asp Tyr Thr Met Asp Trp Val Arg Gln Ala Pro Gly Lys Gly Leu
            35                  40                  45

Glu Trp Val Ala Asp Val Asn Pro Asn Ser Gly Gly Ser Ile Tyr
        50                  55                  60

Asn Gln Arg Phe Lys Gly Arg Phe Thr Leu Ser Val Asp Arg Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                 100                 105

Phe Asp Tyr Trp Gly Gln Gly Thr Leu Val Thr Val Ser Ser
            110                 115

<210> SEQ ID NO 5
<211> LENGTH: 107
<212> TYPE: PRT
<213> ORGANISM: Artificial Sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                 100                 105

Ile Lys

<210> SEQ ID NO 6
<211> LENGTH: 119
<212> TYPE: PRT
<213> ORGANISM: Artificial Sequence
<220> FEATURE:
<223> OTHER INFORMATION: sequence is synthesized

<400> SEQUENCE: 6

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
```

```
                    20                  25                  30

Ser Tyr Ala Met Ser Trp Val Arg Gln Ala Pro Gly Lys Gly Leu
                35                  40                  45

Glu Trp Val Ala Val Ile Ser Gly Asp Gly Gly Ser Thr Tyr Tyr
            50                  55                  60

Ala Asp Ser Val Lys Gly Arg Phe Thr Ile Ser Arg Asp Asn Ser
        65                  70                  75

Lys Asn Thr Leu Tyr Leu Gln Met Asn Ser Leu Arg Ala Glu Asp
    80                  85                  90

Thr Ala Val Tyr Tyr Cys Ala Arg Gly Arg Val Gly Tyr Ser Leu
                95                  100                 105

Tyr Asp Tyr Trp Gly Gln Gly Thr Leu Val Thr Val Ser Ser
                110                 115

<210> SEQ ID NO 7
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 10
<223> OTHER INFORMATION: Xaa is preferrably D or S

<400> SEQUENCE: 7

Gly Phe Thr Phe Thr Asp Tyr Thr Met Xaa
1               5                   10

<210> SEQ ID NO 8
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 8

Asp Val Asn Pro Asn Ser Gly Gly Ser Ile Tyr Asn Gln Arg Phe
1               5                   10                  15

Lys Gly

<210> SEQ ID NO 9
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 9

Asn Leu Gly Pro Ser Phe Tyr Phe Asp Tyr
1               5                   10

<210> SEQ ID NO 10
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 10

Lys Ala Ser Gln Asp Val Ser Ile Gly Val Ala
1               5                   10
```

```
<210> SEQ ID NO 11
<211> LENGTH: 7
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 5
<223> OTHER INFORMATION: Xaa is preferably R or L
<220> FEATURE:
<221> NAME/KEY: Xaa
<222> LOCATION: 6
<223> OTHER INFORMATION: Xaa is preferably Y or E
<220> FEATURE:
<221> NAME/KEY: Xaa
<222> LOCATION: 7
<223> OTHER INFORMATION: Xaa is preferably T or S

<400> SEQUENCE: 11

Ser Ala Ser Tyr Xaa Xaa Xaa
 1               5

<210> SEQ ID NO 12
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 12

Gln Gln Tyr Tyr Ile Tyr Pro Tyr Thr
 1               5

<210> SEQ ID NO 13
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 13

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
                20                  25                  30

Ile Gly Val Ala Trp Tyr Gln Gln Lys Pro Gly Lys Ala Pro Lys
                35                  40                  45

Leu Leu Ile Tyr Ser Ala Ser Tyr Arg Tyr Thr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Tyr Ile Tyr Pro Tyr Thr Phe Gly Gln Gly Thr Lys Val Glu
                95                  100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165
```

```
Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
        185                 190                 195

Val Thr His Gln Gly Leu Ser Ser Pro Val Thr Lys Ser Phe Asn
        200                 205                 210

Arg Gly Glu Cys

<210> SEQ ID NO 14
<211> LENGTH: 448
<212> TYPE: PRT
<213> ORGANISM: Artificial sequence
<220> FEATURE:
<223> OTHER INFORMATION: Sequence is synthesized.

<400> SEQUENCE: 14

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Thr
             20                  25                  30

Asp Tyr Thr Met Asp Trp Val Arg Gln Ala Pro Gly Lys Gly Leu
             35                  40                  45

Glu Trp Val Ala Asp Val Asn Pro Asn Ser Gly Gly Ser Ile Tyr
         50                  55                  60

Asn Gln Arg Phe Lys Gly Arg Phe Thr Leu Ser Val Asp Arg Ser
 65                  70                  75

Lys Asn Thr Leu Tyr Leu Gln Met Asn Ser Leu Arg Ala Glu Asp
             80                  85                  90

Thr Ala Val Tyr Tyr Cys Ala Arg Asn Leu Gly Pro Ser Phe Tyr
             95                 100                 105

Phe Asp Tyr Trp Gly Gln Gly Thr Leu Val Thr Val Ser Ser Ala
            110                 115                 120

Ser Thr Lys Gly Pro Ser Val Phe Pro Leu Ala Pro Ser Ser Lys
            125                 130                 135

Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210

Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu
            275                 280                 285
```

-continued

```
Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu
            320                 325                 330

Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Glu Glu Met
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390

Asn Asn Tyr Lys Thr Thr Pro Pro Val Leu Asp Ser Asp Gly Ser
            395                 400                 405

Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly
            440                 445
```

<210> SEQ ID NO 15
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 15

```
Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Asn
             20                  25                  30

Thr Ala Val Ala Trp Tyr Gln Gln Lys Pro Gly Lys Ala Pro Lys
             35                  40                  45

Leu Leu Ile Tyr Ser Ala Ser Phe Leu Tyr Ser Gly Val Pro Ser
             50                  55                  60

Arg Phe Ser Gly Ser Arg Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90

His Tyr Thr Thr Pro Pro Thr Phe Gly Gln Gly Thr Lys Val Glu
             95                  100                 105

Ile Lys Arg Thr Val Ala Ala Pro Ser Val Phe Ile Phe Pro Pro
             110                 115                 120

Ser Asp Glu Gln Leu Lys Ser Gly Thr Ala Ser Val Val Cys Leu
             125                 130                 135

Leu Asn Asn Phe Tyr Pro Arg Glu Ala Lys Val Gln Trp Lys Val
             140                 145                 150

Asp Asn Ala Leu Gln Ser Gly Asn Ser Gln Glu Ser Val Thr Glu
             155                 160                 165

Gln Asp Ser Lys Asp Ser Thr Tyr Ser Leu Ser Ser Thr Leu Thr
             170                 175                 180
```

```
Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 16
<211> LENGTH: 449
<212> TYPE: PRT
<213> ORGANISM: Artificial sequence
<220> FEATURE:
<223> OTHER INFORMATION: sequence is synthesized

<400> SEQUENCE: 16

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
                35                  40                  45

Glu Trp Val Ala Arg Ile Tyr Pro Thr Asn Gly Tyr Thr Arg Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
                80                  85                  90

Thr Ala Val Tyr Tyr Cys Ser Arg Trp Gly Gly Asp Gly Phe Tyr
                95                  100                 105

Ala Met Asp Tyr Trp Gly Gln Gly Thr Leu Val Thr Val Ser Ser
            110                 115                 120

Ala Ser Thr Lys Gly Pro Ser Val Phe Pro Leu Ala Pro Ser Ser
                125                 130                 135

Lys Ser Thr Ser Gly Gly Thr Ala Ala Leu Gly Cys Leu Val Lys
                140                 145                 150

Asp Tyr Phe Pro Glu Pro Val Thr Val Ser Trp Asn Ser Gly Ala
            155                 160                 165

Leu Thr Ser Gly Val His Thr Phe Pro Ala Val Leu Gln Ser Ser
            170                 175                 180

Gly Leu Tyr Ser Leu Ser Ser Val Val Thr Val Pro Ser Ser Ser
            185                 190                 195

Leu Gly Thr Gln Thr Tyr Ile Cys Asn Val Asn His Lys Pro Ser
                200                 205                 210

Asn Thr Lys Val Asp Lys Lys Val Glu Pro Lys Ser Cys Asp Lys
                215                 220                 225

Thr His Thr Cys Pro Pro Cys Pro Ala Pro Glu Leu Leu Gly Gly
            230                 235                 240

Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp
```

-continued

```
                305                 310                 315
Trp Leu Asn Gly Lys Glu Tyr Lys Cys Lys Val Ser Asn Lys Ala
            320                 325                 330

Leu Pro Ala Pro Ile Glu Lys Thr Ile Ser Lys Ala Lys Gly Gln
            335                 340                 345

Pro Arg Glu Pro Gln Val Tyr Thr Leu Pro Pro Ser Arg Glu Glu
            350                 355                 360

Met Thr Lys Asn Gln Val Ser Leu Thr Cys Leu Val Lys Gly Phe
            365                 370                 375

Tyr Pro Ser Asp Ile Ala Val Glu Trp Glu Ser Asn Gly Gln Pro
            380                 385                 390

Glu Asn Asn Tyr Lys Thr Thr Pro Pro Val Leu Asp Ser Asp Gly
            395                 400                 405

Ser Phe Phe Leu Tyr Ser Lys Leu Thr Val Asp Lys Ser Arg Trp
            410                 415                 420

Gln Gln Gly Asn Val Phe Ser Cys Ser Val Met His Glu Ala Leu
            425                 430                 435

His Asn His Tyr Thr Gln Lys Ser Leu Ser Leu Ser Pro Gly
            440                 445
```

<210> SEQ ID NO 17
<211> LENGTH: 217
<212> TYPE: PRT
<213> ORGANISM: Artificial sequence
<220> FEATURE:
<223> OTHER INFORMATION: Sequence is synthesized.

<400> SEQUENCE: 17

```
Val His Ser Asp Ile Gln Met Thr Gln Ser Pro Ser Ser Leu Ser
  1               5                  10                  15

Ala Ser Val Gly Asp Arg Val Thr Ile Thr Cys Lys Ala Ser Gln
             20                  25                  30

Asp Val Ser Ile Gly Val Ala Trp Tyr Gln Gln Lys Pro Gly Lys
             35                  40                  45

Ala Pro Lys Leu Leu Ile Tyr Ser Ala Ser Tyr Arg Tyr Thr Gly
             50                  55                  60

Val Pro Ser Arg Phe Ser Gly Ser Gly Ser Gly Thr Asp Phe Thr
             65                  70                  75

Leu Thr Ile Ser Ser Leu Gln Pro Glu Asp Phe Ala Thr Tyr Tyr
             80                  85                  90

Cys Gln Gln Tyr Tyr Ile Tyr Pro Tyr Thr Phe Gly Gln Gly Thr
             95                 100                 105

Lys Val Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val
            125                 130                 135

Val Cys Leu Leu Asn Asn Phe Tyr Pro Arg Glu Ala Lys Val Gln
            140                 145                 150

Trp Lys Val Asp Asn Ala Leu Gln Ser Gly Asn Ser Gln Glu Ser
            155                 160                 165

Val Thr Glu Gln Asp Ser Lys Asp Ser Thr Tyr Ser Leu Ser Ser
            170                 175                 180

Thr Leu Thr Leu Ser Lys Ala Asp Tyr Glu Lys His Lys Val Tyr
            185                 190                 195

Ala Cys Glu Val Thr His Gln Gly Leu Ser Ser Pro Val Thr Lys
```

Ser Phe Asn Arg Gly Glu Cys
            215

<210> SEQ ID NO 18
<211> LENGTH: 449
<212> TYPE: PRT
<213> ORGANISM: Artificial sequence
<220> FEATURE:
<223> OTHER INFORMATION: Sequence is synthesized.

<400> SEQUENCE: 18

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
                20                  25                  30

Asp Tyr Thr Met Asp Trp Val Arg Gln Ala Pro Gly Lys Gly Leu
                35                  40                  45

Glu Trp Val Ala Asp Val Asn Pro Asn Ser Gly Gly Ser Ile Tyr
                50                  55                  60

Asn Gln Arg Phe Lys Gly Arg Phe Thr Leu Ser Val Asp Arg Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                 100                 105

Phe Asp Tyr Trp Gly Gln Gly Thr Leu Val Thr Val Ser Ser Ala
               110                 115                 120

Ser Thr Lys Gly Pro Ser Val Phe Pro Leu Ala Pro Ser Ser Lys
               125                 130                 135

Ser Thr Ser Gly Gly Thr Ala Ala Leu Gly Cys Leu Val Lys Asp
               140                 145                 150

Tyr Phe Pro Glu Pro Val Thr Val Ser Trp Asn Ser Gly Ala Leu
               155                 160                 165

Thr Ser Gly Val His Thr Phe Pro Ala Val Leu Gln Ser Ser Gly
               170                 175                 180

Leu Tyr Ser Leu Ser Ser Val Val Thr Val Pro Ser Ser Ser Leu
               185                 190                 195

Gly Thr Gln Thr Tyr Ile Cys Asn Val Asn His Lys Pro Ser Asn
               200                 205                 210

Thr Lys Val Asp Lys Lys Val Glu Pro Lys Ser Cys Asp Lys Thr
               215                 220                 225

His Thr Cys Pro Pro Cys Pro Ala Pro Glu Leu Leu Gly Gly Pro
               230                 235                 240

Ser Val Phe Leu Phe Pro Pro Lys Pro Lys Asp Thr Leu Met Ile
               245                 250                 255

Ser Arg Thr Pro Glu Val Thr Cys Val Val Val Asp Val Ser His
               260                 265                 270

Glu Asp Pro Glu Val Lys Phe Asn Trp Tyr Val Asp Gly Val Glu
               275                 280                 285

Val His Asn Ala Lys Thr Lys Pro Arg Glu Glu Gln Tyr Asn Ser
               290                 295                 300

Thr Tyr Arg Val Val Ser Val Leu Thr Val Leu His Gln Asp Trp
               305                 310                 315

Leu Asn Gly Lys Glu Tyr Lys Cys Lys Val Ser Asn Lys Ala Leu

-continued

```
                320                 325                 330
Pro Ala Pro Ile Glu Lys Thr Ile Ser Lys Ala Lys Gly Gln Pro
            335                 340                 345
Arg Glu Pro Gln Val Tyr Thr Leu Pro Pro Ser Arg Glu Glu Met
        350                 355                 360
Thr Lys Asn Gln Val Ser Leu Thr Cys Leu Val Lys Gly Phe Tyr
    365                 370                 375
Pro Ser Asp Ile Ala Val Glu Trp Glu Ser Asn Gly Gln Pro Glu
380                 385                 390
Asn Asn Tyr Lys Thr Thr Pro Pro Val Leu Asp Ser Asp Gly Ser
            395                 400                 405
Phe Phe Leu Tyr Ser Lys Leu Thr Val Asp Lys Ser Arg Trp Gln
        410                 415                 420
Gln Gly Asn Val Phe Ser Cys Ser Val Met His Glu Ala Leu His
    425                 430                 435
Asn His Tyr Thr Gln Lys Ser Leu Ser Leu Ser Pro Gly Lys
440                 445

<210> SEQ ID NO 19
<211> LENGTH: 195
<212> TYPE: PRT
<213> ORGANISM: Homo sapiens

<400> SEQUENCE: 19

Thr Gln Val Cys Thr Gly Thr Asp Met Lys Leu Arg Leu Pro Ala
1               5                   10                  15
Ser Pro Glu Thr His Leu Asp Met Leu Arg His Leu Tyr Gln Gly
            20                  25                  30
Cys Gln Val Val Gln Gly Asn Leu Glu Leu Thr Tyr Leu Pro Thr
        35                  40                  45
Asn Ala Ser Leu Ser Phe Leu Gln Asp Ile Gln Glu Val Gln Gly
    50                  55                  60
Tyr Val Leu Ile Ala His Asn Gln Val Arg Gln Val Pro Leu Gln
65                  70                  75
Arg Leu Arg Ile Val Arg Gly Thr Gln Leu Phe Glu Asp Asn Tyr
            80                  85                  90
Ala Leu Ala Val Leu Asp Asn Gly Asp Pro Leu Asn Asn Thr Thr
        95                  100                 105
Pro Val Thr Gly Ala Ser Pro Gly Gly Leu Arg Glu Leu Gln Leu
    110                 115                 120
Arg Ser Leu Thr Glu Ile Leu Lys Gly Gly Val Leu Ile Gln Arg
125                 130                 135
Asn Pro Gln Leu Cys Tyr Gln Asp Thr Ile Leu Trp Lys Asp Ile
            140                 145                 150
Phe His Lys Asn Asn Gln Leu Ala Leu Thr Leu Ile Asp Thr Asn
        155                 160                 165
Arg Ser Arg Ala Cys His Pro Cys Ser Pro Met Cys Lys Gly Ser
    170                 175                 180
Arg Cys Trp Gly Glu Ser Ser Glu Asp Cys Gln Ser Leu Thr Arg
185                 190                 195

<210> SEQ ID NO 20
<211> LENGTH: 124
<212> TYPE: PRT
<213> ORGANISM: Homo sapiens
```

<400> SEQUENCE: 20

```
Thr Val Cys Ala Gly Gly Cys Ala Arg Cys Lys Gly Pro Leu Pro
  1               5                  10                  15

Thr Asp Cys Cys His Glu Gln Cys Ala Ala Gly Cys Thr Gly Pro
                 20                  25                  30

Lys His Ser Asp Cys Leu Ala Cys Leu His Phe Asn His Ser Gly
                 35                  40                  45

Ile Cys Glu Leu His Cys Pro Ala Leu Val Thr Tyr Asn Thr Asp
                 50                  55                  60

Thr Phe Glu Ser Met Pro Asn Pro Glu Gly Arg Tyr Thr Phe Gly
                 65                  70                  75

Ala Ser Cys Val Thr Ala Cys Pro Tyr Asn Tyr Leu Ser Thr Asp
                 80                  85                  90

Val Gly Ser Cys Thr Leu Val Cys Pro Leu His Asn Gln Glu Val
                 95                 100                 105

Thr Ala Glu Asp Gly Thr Gln Arg Cys Glu Lys Cys Ser Lys Pro
                110                 115                 120

Cys Ala Arg Val
```

<210> SEQ ID NO 21
<211> LENGTH: 169
<212> TYPE: PRT
<213> ORGANISM: Homo sapiens

<400> SEQUENCE: 21

```
Cys Tyr Gly Leu Gly Met Glu His Leu Arg Glu Val Arg Ala Val
  1               5                  10                  15

Thr Ser Ala Asn Ile Gln Glu Phe Ala Gly Cys Lys Lys Ile Phe
                 20                  25                  30

Gly Ser Leu Ala Phe Leu Pro Glu Ser Phe Asp Gly Asp Pro Ala
                 35                  40                  45

Ser Asn Thr Ala Pro Leu Gln Pro Glu Gln Leu Gln Val Phe Glu
                 50                  55                  60

Thr Leu Glu Glu Ile Thr Gly Tyr Leu Tyr Ile Ser Ala Trp Pro
                 65                  70                  75

Asp Ser Leu Pro Asp Leu Ser Val Phe Gln Asn Leu Gln Val Ile
                 80                  85                  90

Arg Gly Arg Ile Leu His Asn Gly Ala Tyr Ser Leu Thr Leu Gln
                 95                 100                 105

Gly Leu Gly Ile Ser Trp Leu Gly Leu Arg Ser Leu Arg Glu Leu
                110                 115                 120

Gly Ser Gly Leu Ala Leu Ile His His Asn Thr His Leu Cys Phe
                125                 130                 135

Val His Thr Val Pro Trp Asp Gln Leu Phe Arg Asn Pro His Gln
                140                 145                 150

Ala Leu Leu His Thr Ala Asn Arg Pro Glu Asp Glu Cys Val Gly
                155                 160                 165

Glu Gly Leu Ala
```

<210> SEQ ID NO 22
<211> LENGTH: 142
<212> TYPE: PRT
<213> ORGANISM: Homo sapiens

<400> SEQUENCE: 22

-continued

```
Cys His Gln Leu Cys Ala Arg Gly His Cys Trp Gly Pro Gly Pro
1               5                  10                 15

Thr Gln Cys Val Asn Cys Ser Gln Phe Leu Arg Gly Gln Glu Cys
                20              25                  30

Val Glu Glu Cys Arg Val Leu Gln Gly Leu Pro Arg Glu Tyr Val
                35              40                  45

Asn Ala Arg His Cys Leu Pro Cys His Pro Glu Cys Gln Pro Gln
                50              55                  60

Asn Gly Ser Val Thr Cys Phe Gly Pro Glu Ala Asp Gln Cys Val
                65              70                  75

Ala Cys Ala His Tyr Lys Asp Pro Pro Phe Cys Val Ala Arg Cys
                80              85                  90

Pro Ser Gly Val Lys Pro Asp Leu Ser Tyr Met Pro Ile Trp Lys
                95              100                 105

Phe Pro Asp Glu Glu Gly Ala Cys Gln Pro Cys Pro Ile Asn Cys
                110             115                 120

Thr His Ser Cys Val Asp Leu Asp Asp Lys Gly Cys Pro Ala Glu
                125             130                 135

Gln Arg Ala Ser Pro Leu Thr
                140
```